(12) United States Patent
Yang et al.

(10) Patent No.: US 10,849,993 B2
(45) Date of Patent: Dec. 1, 2020

(54) CONTRAST AGENTS, METHODS FOR PREPARING CONTRAST AGENTS, AND METHODS OF IMAGING

(71) Applicant: Georgia State University Research Foundation, Atlanta, GA (US)

(72) Inventors: Jenny Jie Yang, Atlanta, GA (US); Zhiren Liu, Atlanta, GA (US); Jie Jiang, Atlanta, GA (US); Shenghui Xue, Atlanta, GA (US); Jinjuan Qiao, Atlanta, GA (US); Mani Salarian, Decatur, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 17 days.

(21) Appl. No.: 15/910,893

(22) Filed: Mar. 2, 2018

(65) Prior Publication Data
US 2018/0250426 A1 Sep. 6, 2018

Related U.S. Application Data

(63) Continuation of application No. 12/935,413, filed as application No. PCT/US2009/039276 on Apr. 2, 2009, now abandoned.

(60) Provisional application No. 61/041,693, filed on Apr. 2, 2008.

(51) Int. Cl.
*A61K 49/14* (2006.01)
*A61K 49/12* (2006.01)

(52) U.S. Cl.
CPC ............ *A61K 49/14* (2013.01); *A61K 49/126* (2013.01); *A61K 49/143* (2013.01)

(58) Field of Classification Search
CPC ..... A61K 49/126; A61K 49/143; A61K 49/14
See application file for complete search history.

(56) References Cited

U.S. PATENT DOCUMENTS

| | | | |
|---|---|---|---|
| 4,508,625 | A | 4/1985 | Graham |
| 5,679,548 | A | 10/1997 | Barbas et al. |
| 5,690,903 | A | 11/1997 | Hainfeld |
| 5,922,302 | A | 7/1999 | Goldenberg et al. |
| 6,197,258 | B1 | 3/2001 | Thompson et al. |
| 7,405,320 | B2 | 7/2008 | McBride et al. |
| 8,173,105 | B2 | 5/2012 | Yang et al. |
| 2002/0015038 | A1 | 2/2002 | Patel et al. |
| 2002/0136692 | A1 | 9/2002 | Harron et al. |
| 2003/0149254 | A1 | 8/2003 | Anderson et al. |
| 2003/0180222 | A1 | 9/2003 | Zhang et al. |
| 2004/0208827 | A1 | 10/2004 | McMurry et al. |
| 2006/0029942 | A1 | 2/2006 | Yang |
| 2006/0030029 | A1 | 2/2006 | Yang |
| 2006/0031020 | A1 | 2/2006 | Yang |
| 2009/0104123 | A1 | 4/2009 | Yang et al. |

FOREIGN PATENT DOCUMENTS

| | | | |
|---|---|---|---|
| EP | 1238982 A | 9/2002 | |
| WO | 2001030398 A2 | 5/2001 | |
| WO | 2003014157 A2 | 2/2003 | |
| WO | WO-03014157 A2 * | 2/2003 | ........... A61K 49/085 |
| WO | 2003057829 A2 | 7/2003 | |
| WO | 2005097208 | 10/2005 | |
| WO | 2006080022 A2 | 8/2006 | |
| WO | 2006107794 A2 | 10/2006 | |
| WO | 2007009058 | 1/2007 | |

OTHER PUBLICATIONS

MacKenzie et al. Bifunctional fusion proteins consisting of single-chain antibody and an engineered lanthanide-binding protein. Immunotechnology 1995, pp. 139-150. (Year: 1995).*
Clainche et al. Engineering new metal specificity in EF-hand peptides. J.Biol Inorg. Chem. 2003, vol. 8, pp. 334-340. (Year: 2003).*
Henzel, et al. "15N nuclear magnetic resonance relaxation studies on rat β-parvalbumin and the pentacarboxylate variants, S55D and G98D." Protein Science, 2002, vol. 11, pp. 158-173.
Henzel, et al. "Estimation of parvalbumin Ca2+- and Mg2+-binding constants by global least-squares analysis of isothermal titration calorimetry data." Analytical Biochemistry, 2003, vol. 319, pp. 216-233.
Lee, et al. "Crystal Structure of a High-Affinity Variant of Rat α-Parvalbumin." Biochemistry, 2004, vol. 43, pp. 10008-10017.
Bertini, et al. "Tuning the Affinity for Lanthanides of Calcium Binding Proteins." Biochemistry, 2003, vol. 42, pp. 8011-8021.
Haiech, et al. "Restoration of the Calcium Binding Activity of Mutant Calmodulins toward Normal by the Presence of a Calmodulin Binding Structure." J. Biological Chemistry, 1991, vol. 266, No. 6, pp. 3427-3431.
Chattopadhyaya, et al. "Calmodulin Structure Refined at 1·7 Å Resolution." J. Molecular Biology, 1992, vol. 228, pp. 1177-1192.
Caravan et al. Gadolinium-binding helix-turn-helix peptides: DNA-dependent MRI contrast agents. Chem. Commun 2003, pp. 2574-2575.
Roberts M J et al: "Chemistry for peptide and protein PEGylation", Advanced Drug Delivery Reviews, Elsevier, Amsterdam, NL, val. 54, No. 4, Jun. 17, 2002 (Jun. 17, 2002), pp. 459-476.
Veron Ese F Metal: "PEGylation, successful approach to drug delivery", Drug Discovery Today, Elsevier, Rahway, NJ, US, va 1.10, No. 21, Nov. 1, 2005 (Nov. 1, 2005), pp. 1451-1458.
Bogdanov A A et al: "Long-Cirulcating Blood Pool Imaging Agents", Advanced Drug Delivery Reviews, Elsevier, Amsterdam, NL, vol. 16, No. 2/03, Jan. 1, 1995 (Jan. 1, 1995), pp. 335-348.
Strijkers G J et al: "Relaxivity of liposomal paramagnetic MRI contrast agents", Magnetic Resonance Materials in Physics, Biology and Medicine, Chapman and Hall, London, GB, val. 18, No. 4, Sep. 1, 2005 (Sep. 1, 2005), pp. 186-192.

(Continued)

*Primary Examiner* — Shafiqul Haq
(74) *Attorney, Agent, or Firm* — Thomas | Horstemeyer, LLP

(57) ABSTRACT

Embodiments of the present disclosure provide for contrast agents, methods of making contrast agents, and methods of using contrast agents, and the like.

16 Claims, 34 Drawing Sheets

Specification includes a Sequence Listing.

(56) References Cited

OTHER PUBLICATIONS

Dan M. J. Doble et al: "Optimization of the Relaxivity of MRI Contrast Agents: Effect of Poly( ethylene glycol) Chains on the Water-Exchange Rates of Gd III Complexes", Journal of the American Chemical Society, va I. 123, No. 43, Oct. 1, 2001 (Oct. 1, 2001 ), pp. 10758-10759.
Aaron M. Mohs et al: "-cystine): Effect of PEG Chain Length on in Vivo Contrast Enhancement in MRI", Biomacromolecules, val. 6, No. 4, Jul. 1, 2005 (Jul. 1, 2005 ), pp. 2305-2311.
Shi Ke et al: "Imaging taxane-induced tumor apoptosis using PEGylated, 1111 n-labeled annexin V.", The Journal of Nuclear Medicine, val. 45, No. 1, Jan. 1, 2004 (Jan. 1, 2004 ), pp. 108-115.
Jenny J Yang et al: "Rational design of protein-based MRI contrast agents", Journal of the American Chemical Society, ACS Publications, US, val. 130, No. 29, Jul. 23, 2008 (Jul. 23, 2008), pp. 9260-9267.
Shunyi Li et al: "PEGylation of protein-based MRI contrast agents improves relaxivities and biocompatibilities", Journal of Inorganic Biochemistry, Elsevier Inc, US, val. 107, No. 1, Nov. 8, 2011 (Nov. 8, 2011), pp. 111-118.
Jingjuan Qiao et al: "HER2 Targeted Molecular MR Imaging Using a De Novo Designed Protein Contrast Agent". PLOS ONE, val. 6, No. 3, Mar. 24, 2011 (Mar. 24, 2011), p. e18103.
Shenghui Xue et al: "Design of a novel class of protein-based magnetic resonance imaging contrast agents for the molecular imaging of cancer biomarkers", Wiley Interdisciplinary Reviews: Nanomedicine and Nanobiotechnology, vol. 5, No. 2, Mar. 17, 2013 (Mar. 17, 2013), pp. 163-179.
Lixia Wei et al: "Protein-Based MRI Contrast Agents for Molecular Imaging of Prostate Cancer", Molecular Imaging and Biology, Springer-Verlag, NE, vol. 13, No. 3, Jun. 24, 2010 (Jun. 24, 2010), pp. 416-423.
European Search Report; dated Sep. 16, 2014 for application EP09755461; 14 pages, Munich.
Patonay et al. Near-infrared fluorogenic labels: new approach to an old problem. Analytical chemistry 1991, vol. 63, No. 6, pp. 321-327.
Mesecar, et al., "Orbital Steering in the Catalytic Power of Enzymes: Small Structural Changes with Large Catalytic Consequences," Science Jul. 11, 1997 :277(5323):202-6.
Smith, et al., "Entry for Quaternary Structure," Oxford Dictionary of Biochemistry and Molecular Biology, Oxford University Press, New Yair 1997, p. 551.
Richmond, et al., "Engineered Metal Binding Sites on Green Fluorescence Protein," Biochemical and Biophysical Research Communications, vol. 268, No. 2, Feb. 16, 2000, pp. 462-465.
Romoser, et al., "Detection in Living Cells of Ca-2+-dependent Changes in the Fluroescence Emission of an Indicator Composed of Two Green Fluorescent Protein Variants Linked by a Calmodulin-binding Sequence: A New Class of Fluorescent Indicators," Journal of Biological Chemistry, col. 272, No. 20, 1997, pp. 13270-13274.
Nagai, et al., "Circularly Permuted Green Fluorescent Proteins Engineered to Sense Ca2+" Proceedings of the National Academy of Sciences of USA, National Academy of Science, Washington, DC, vol. 98, No. 6, Mar. 13, 2001, pp. 3197-3202.
Wilkins, et al., "Metal-Binding Studies for a De Novo Designed Calcium-Binding Protein," Protein Engineering, val. 15, No. 7, Jul. 2002, pp. 571-574.
Hellinga, et al., "Protein Engineering and the Development of Generic Biosensors," Trends in Biotechnology. val 16, No. 4, 1998, p. 183.

Supplemental European Search Report dated Aug. 25, 2009.
Elbanowski, et al., "Fluorescence of Lanthanide (III) Complexes in Aqueous Solutions: The Influence of pH and Solution Composition," Monatshfte fur Chemie, 1985, val. 116, pp. 901-911.
Johnson, et al., "Structural Changes Required for Activation of Protein Care Induced by CA2+ Binding to a High Affinity Site that Does Not Contain g-Carboxyglutamic Acid," The Journal of Biological Chemistry, 1983, vol. 268, pp. 5554-5560.
Lewis, et al., "Fiuroescence Binding Assay for a Small Peptide Based on a GFP Fusion Protein," Analytica Chimica Acta., val. 397. 1999, pp. 279-286.
Schlyer et al., "Time-Resolved Room Temperature Protein Phosphorescence: Nonexponential Decay from Single Emitting Tryptophans," Biophysical Journal, val. 67, 1994, pp. 1192-1202.
Yang, et al., "The Molecular Structure of Green Fluorescent Protein," Nature Biotechnology, vol. 14, 1996, pp. 1246-151.
Shelling, et al., "Protein Nuclear Magnetic Resonance Studies of the Interaction of the Lanthanide Yetterbium and Lutetium with Apo—and Calcium Saturated Porcine Intestinal Calcium Binding Protein," Biochemistry, 1985, val. 24, pp. 2332-2338.
Yang, et al., "Rational Design of a Calcium-Binding Protein," Journal of the American Chemical Society, Apr. 2003, vol. 125, pp. 6165-6171.
Ye, et al., "A Grafting Approach to Obtain Site-Specific Metal-Binding Properties of EF-Hand Proteins," Protein Engineering, vol. 16, No. 6; pp. 429-434, 2003.
Ye, et al., "Metal Binding Affinity and Structural Properties of an Isolated EF-Loop in a Scaffold Protein," Protein Engineering, vol. 14, No. 12, pp. 1001-1013; 2001.
MacKenzie, et al., "Bifunctional Fusion Proteins Consisting of a Single-Chain Antibody and an Engineered Lanthanide=Binding Protein," Immunotechnology 1 (1995), pp. 139-150.
Lee, et al., "Isolated EF-Loop III of Calmodulin in a Scaffold Protein Remains Unpaired in Solution Using Pulsed-Field-Gradient NMR Spectroscopy," Biochimica et Biophysica Acta; 1598 (2002), pp. 80-87.
Miyawaki, et al., Fluorescent Indicators for CA2+ Based on Green Fluorescent Proteins and Calmodulin; Nature, vol. 388, Aug. 28, 1997, pp. 882887.
Prasher, et al., "Primary Structure of the Aequorea Victoria Green-Fluorescent Protein," Gene, 1992, vol. 111, 99. 229-233.
Yang et al., "Obtaining Site-Specific Calcium-Binding Affinities of Calmodulin," Protein and Peptide Letters, vol. 10, No. 1 4, pp. 331-345, 2003.
Kawasaki, et al., "Classification and Evolution of EF-Hand Proteins," BioMetals; 1998, vol. 11, pp. 275-295.
International Search Report and Written Opinion, dated Jul. 14, 2008.
Anton, et al., "Biotinylation of a Bombesin" 1991, Peptides, 12, pp. 375-381.
International Search Report and Written Opinion dated Nov. 28, 2007.
Cohen, et al., "Ferritin as an Endogenous MRI Reporter for Non-invasive Imaging of Gene Expression in C6 Glioma Tumors," Neoplasia, Feb. 2005, val. 7, No. 2, pp. 109-111.
Pessl, et al., "A Designed Metal-Binding Protein with a Novel Fold," Nature, Mar. 25, 1993, 362, 367, 369 (online).
International Search Report and Written Opinion dated Feb. 1, 2007.
International Preliminary Report on Patentability dated Oct. 14, 2010.

* cited by examiner

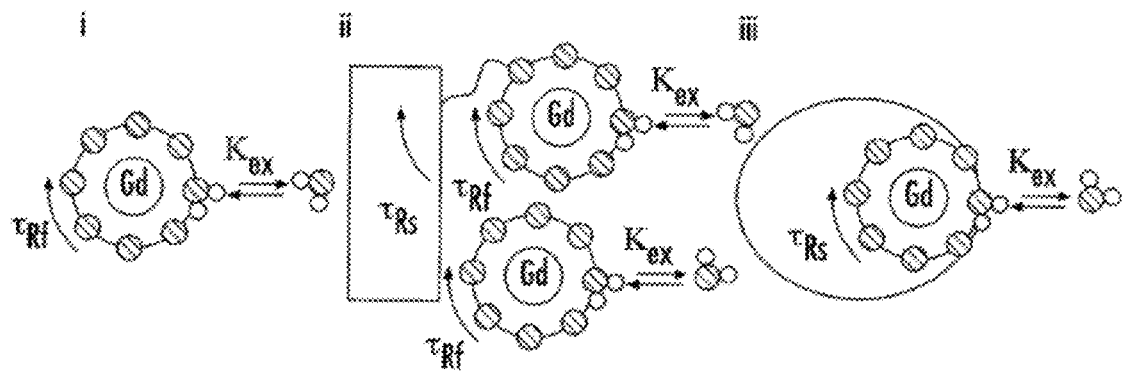
Fig. 1.1A
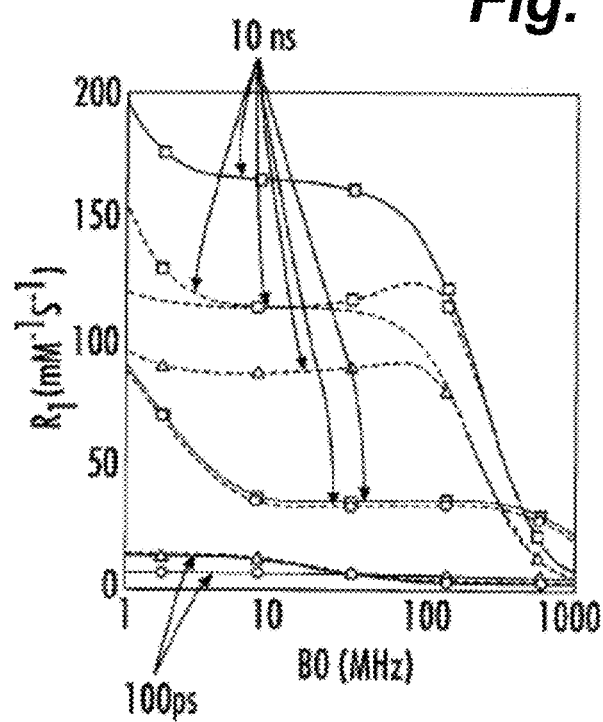
Fig. 1.1B
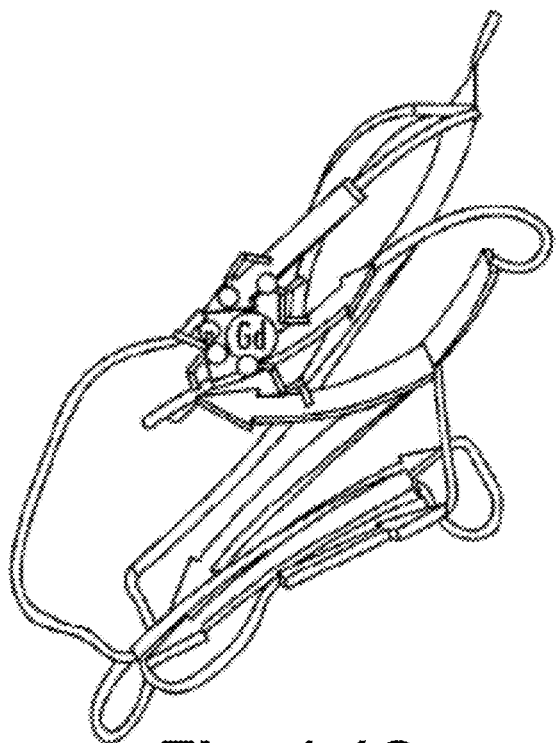
Fig. 1.1C

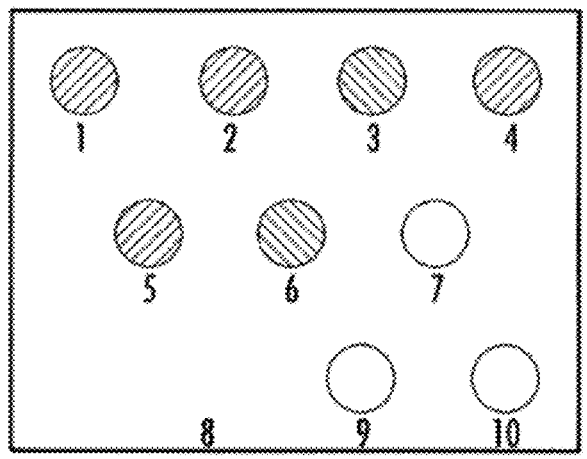
Fig. 1.2A
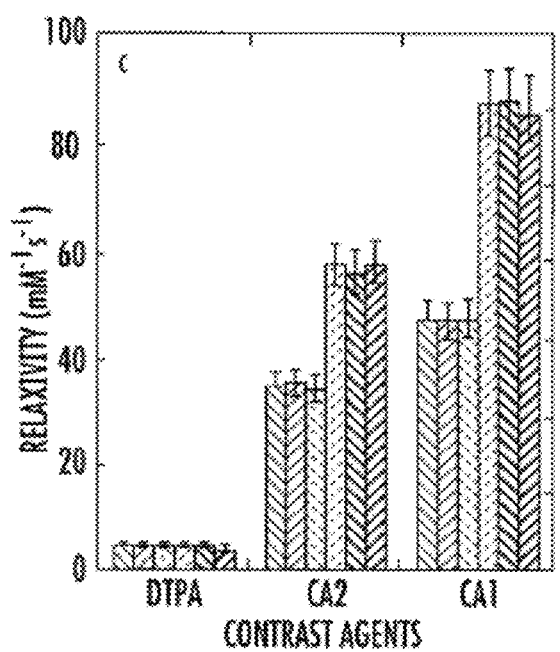
Fig. 1.2C
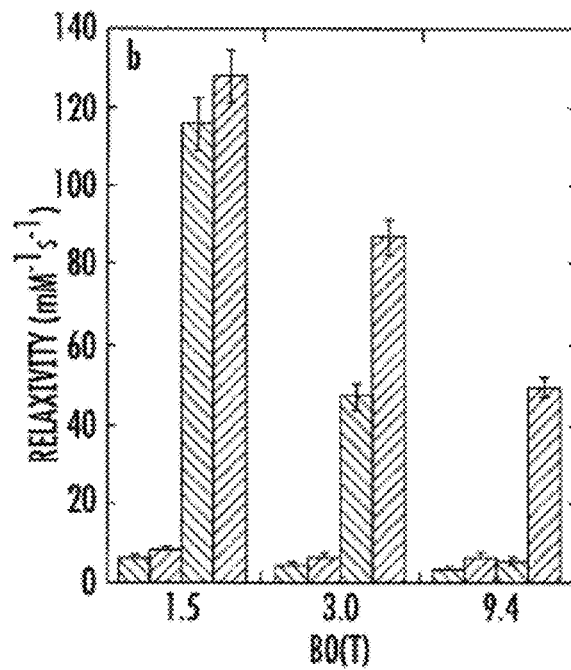
Fig. 1.2B

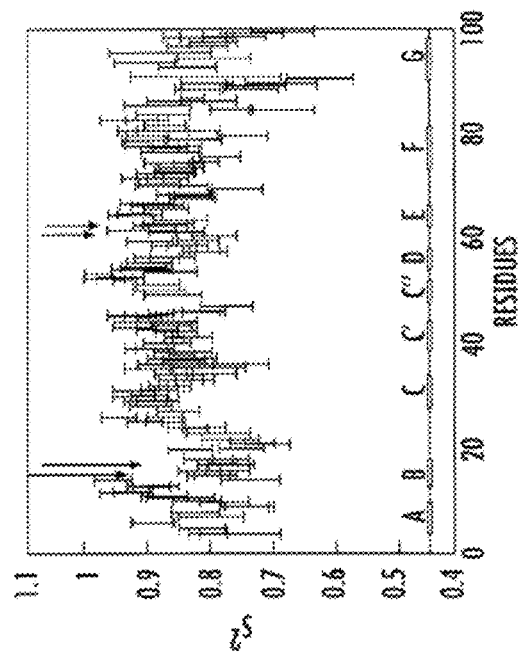
*Fig. 1.3A*
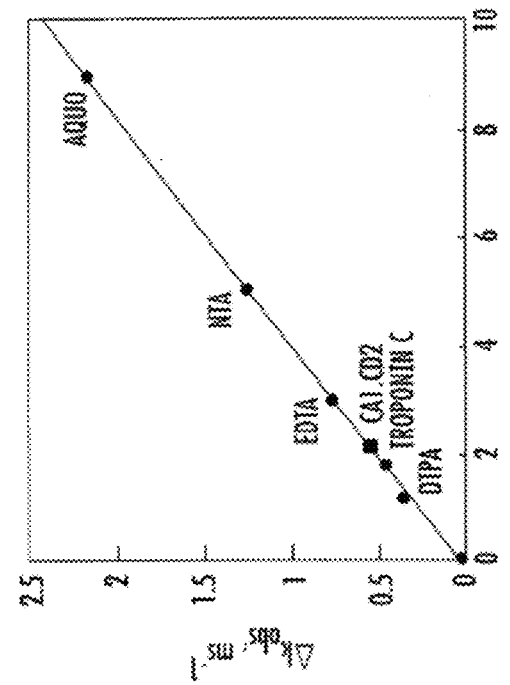
*Fig. 1.3B*
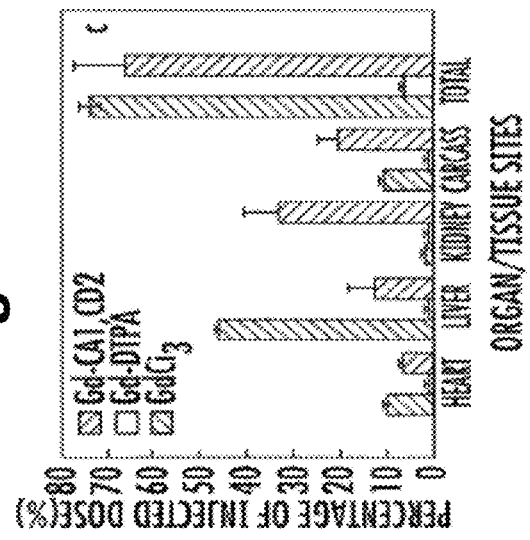
*Fig. 1.4C*
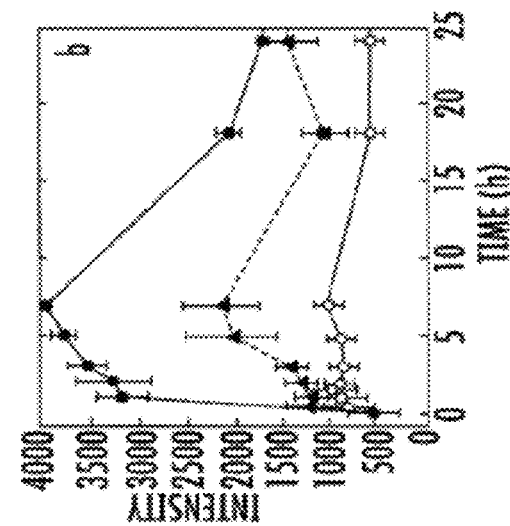
*Fig. 1.4B*
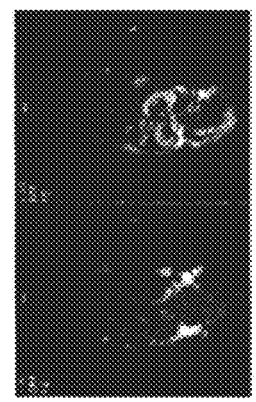
*Fig. 1.4A*

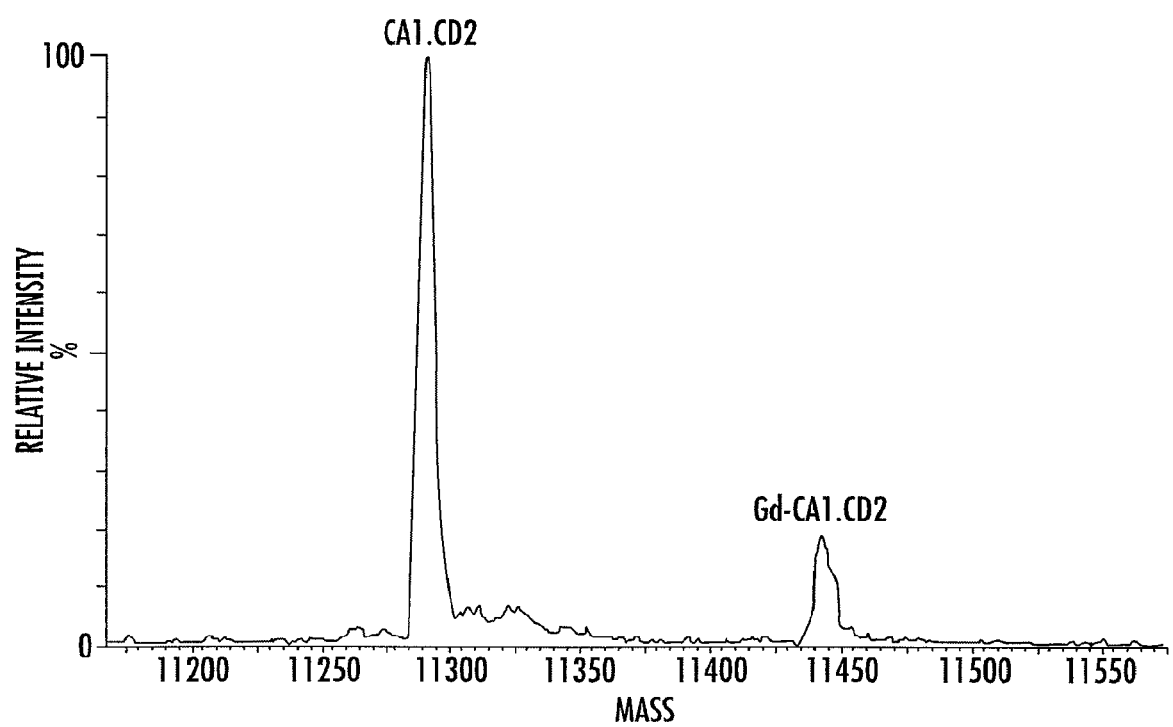
FIG. 1.5

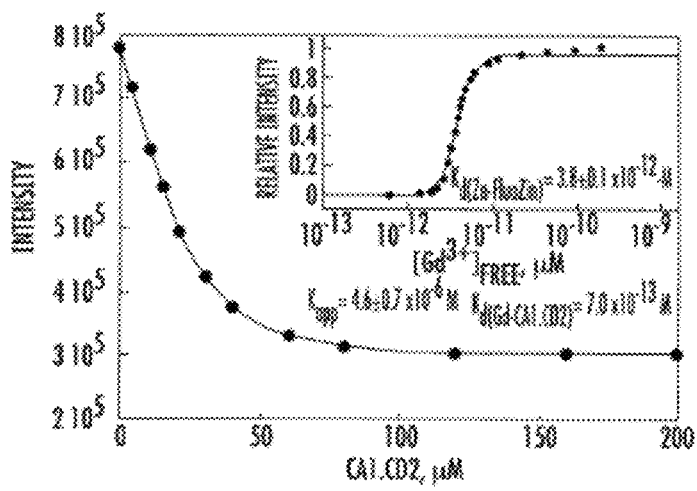
*Fig. 1.6A*
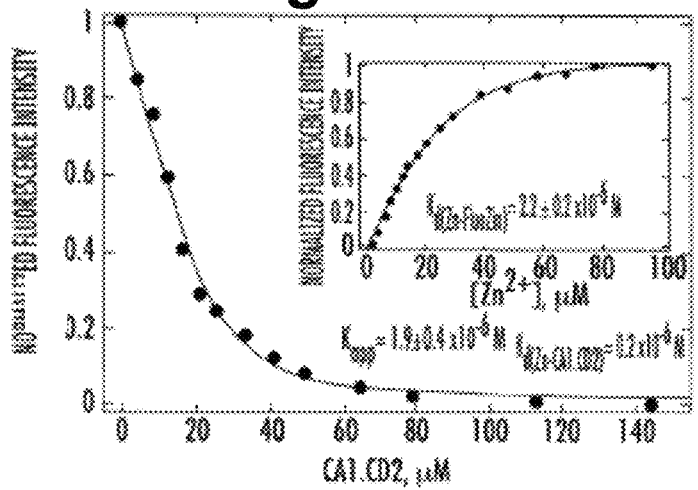
*Fig. 1.6B*
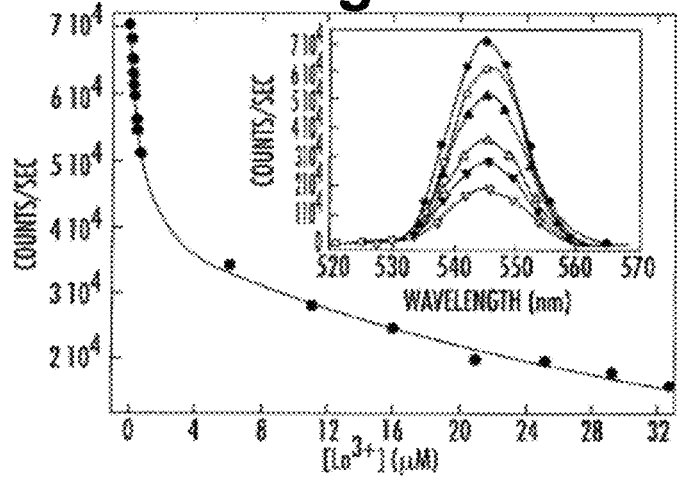
*Fig. 1.6C*

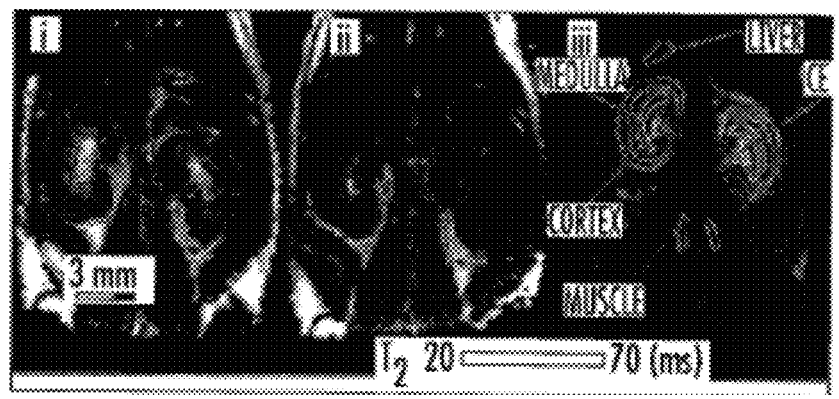
*Fig. 1.7A*
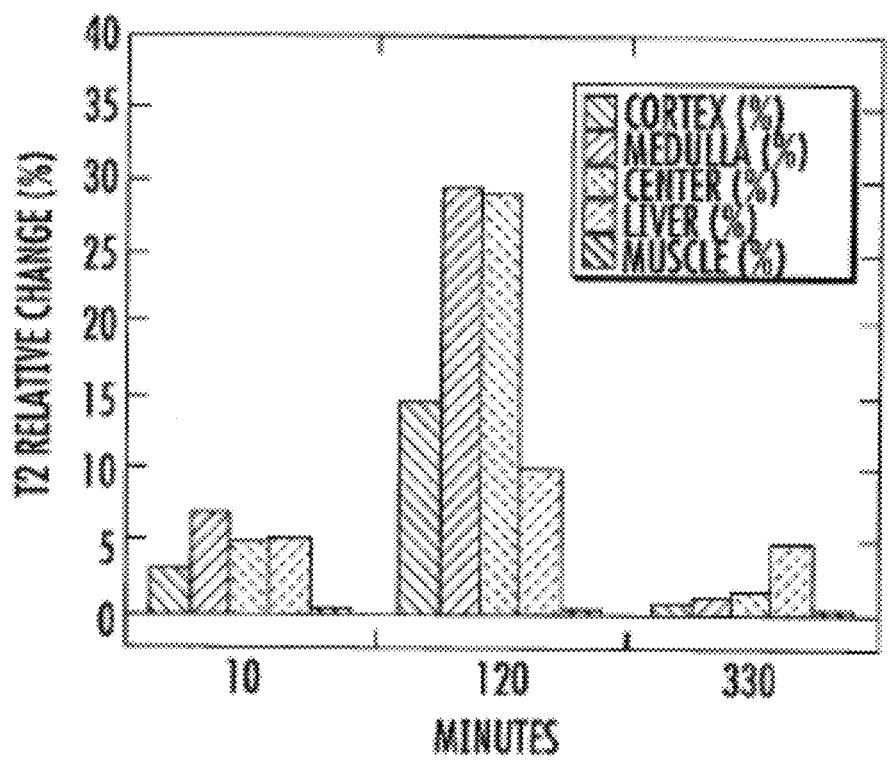
*Fig. 1.7B*

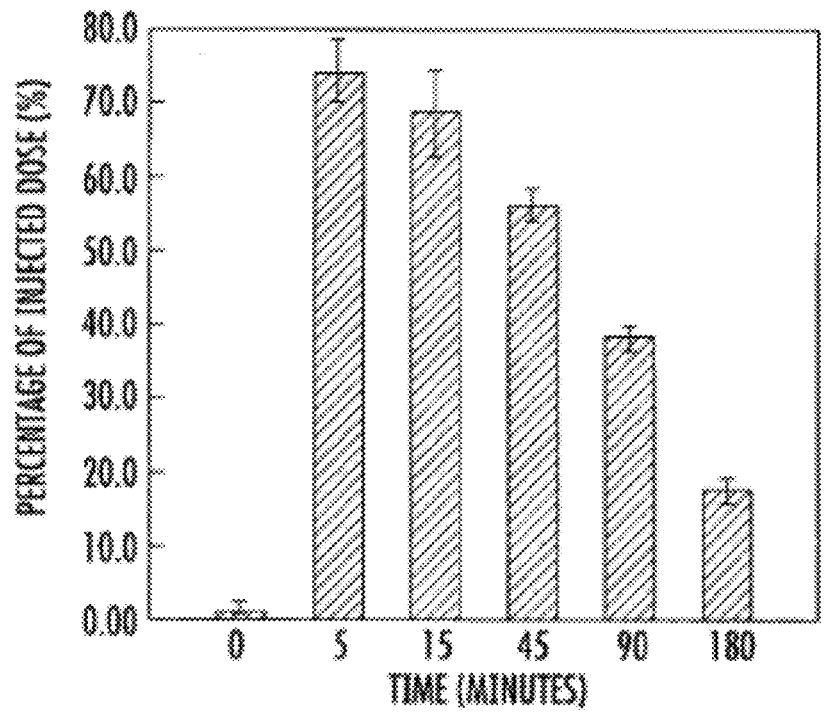
Fig. 1.8A
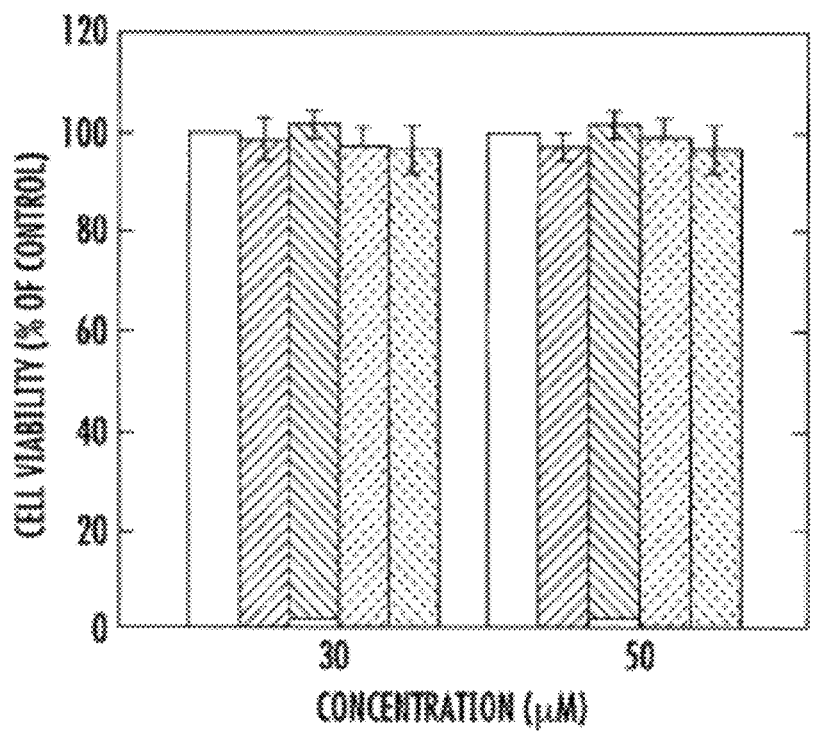
Fig. 1.8B

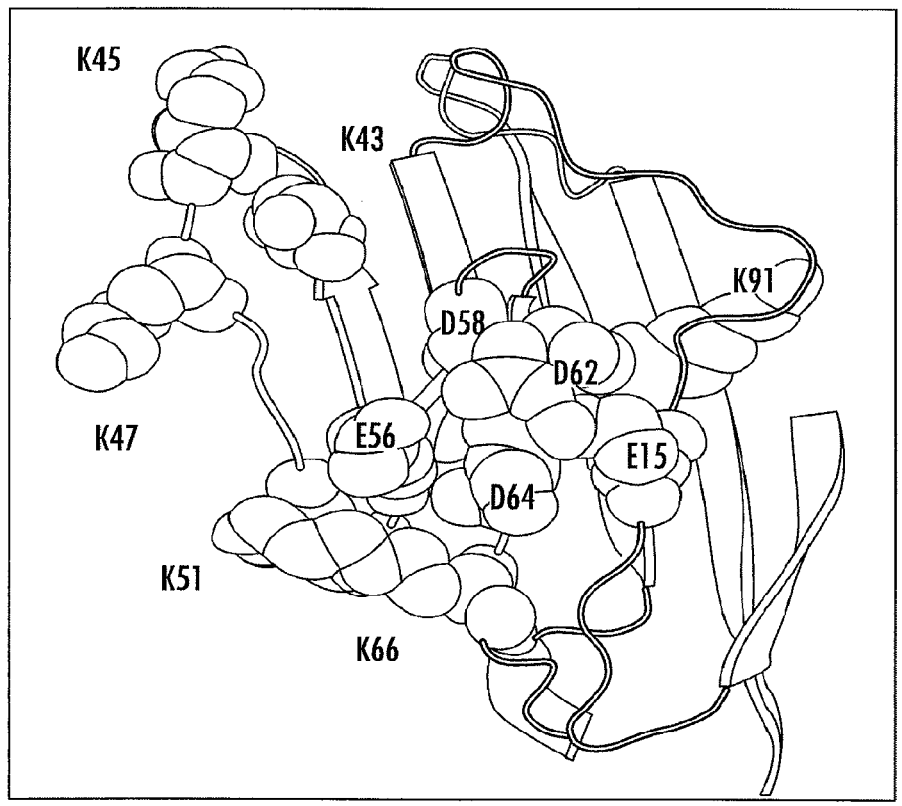
SOLVENT ACCESSIBLE SURFACE AREA
1. K45 - 100.0
2. K47 - 99.9
3. D1 - 78.3
4. K66 - 56.2
5. K51 - 54.8
6. K43 - 41.6
7. K91 - 22.2
FIG. 2.1A

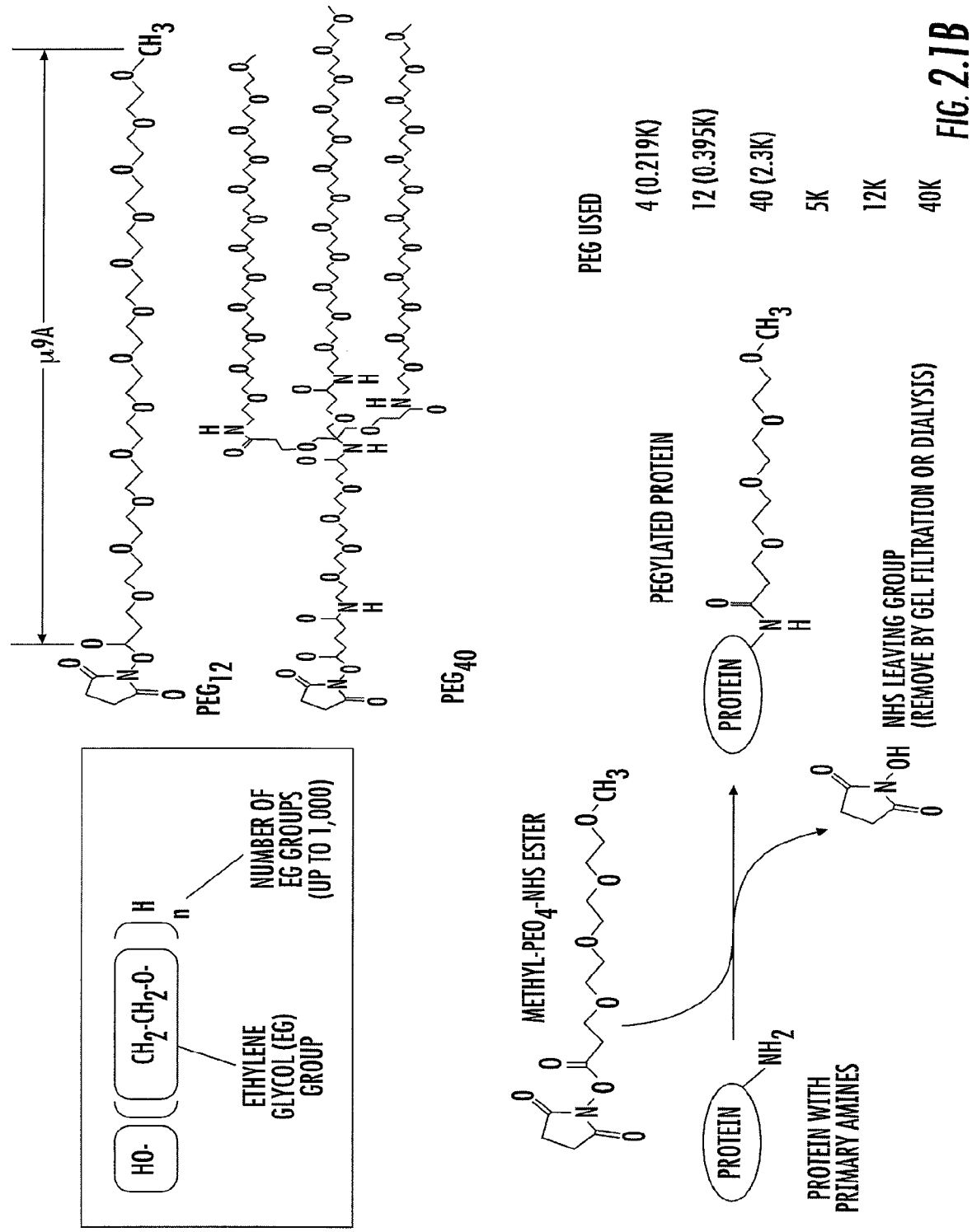
FIG. 2.1B

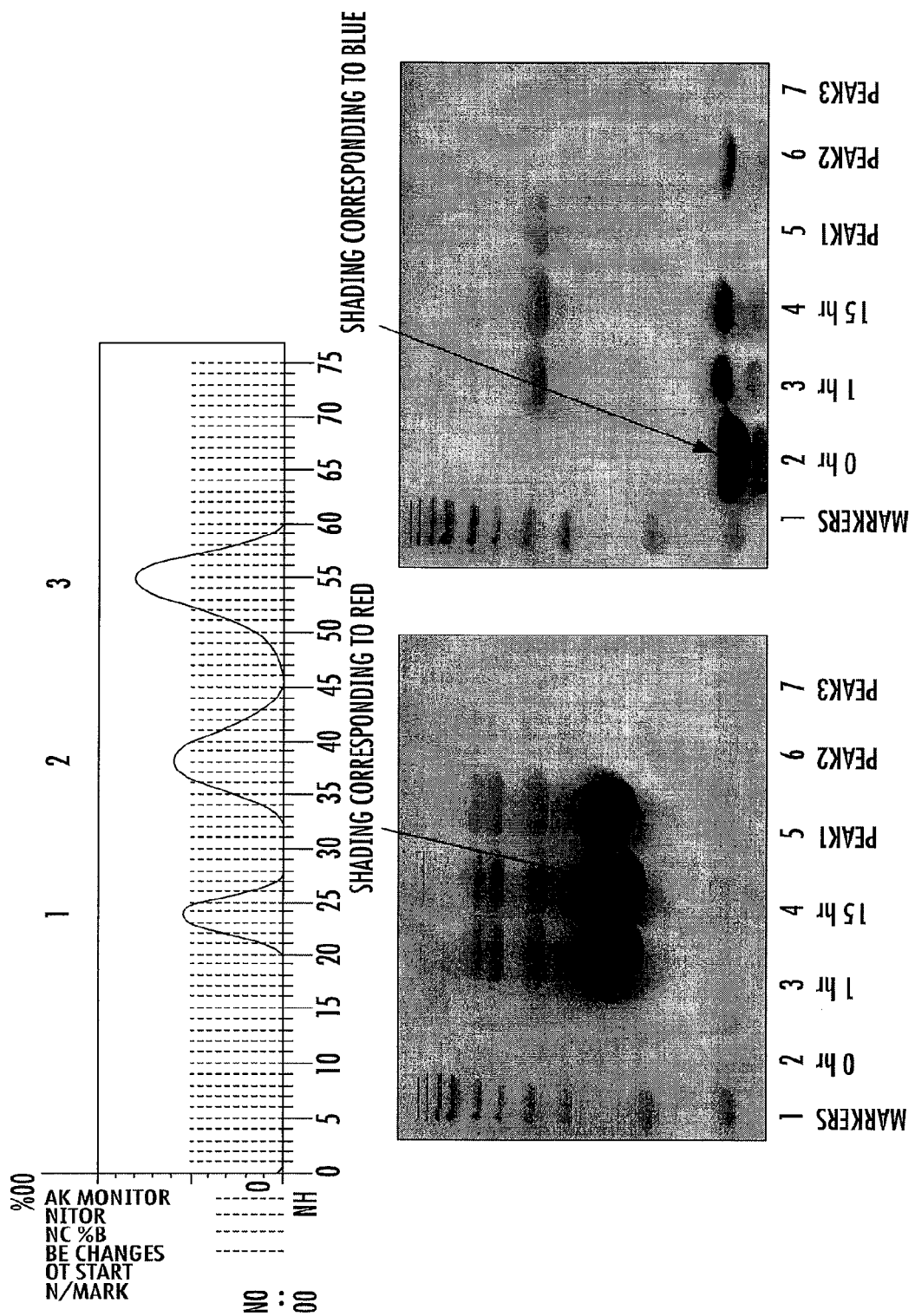
FIG. 2.2

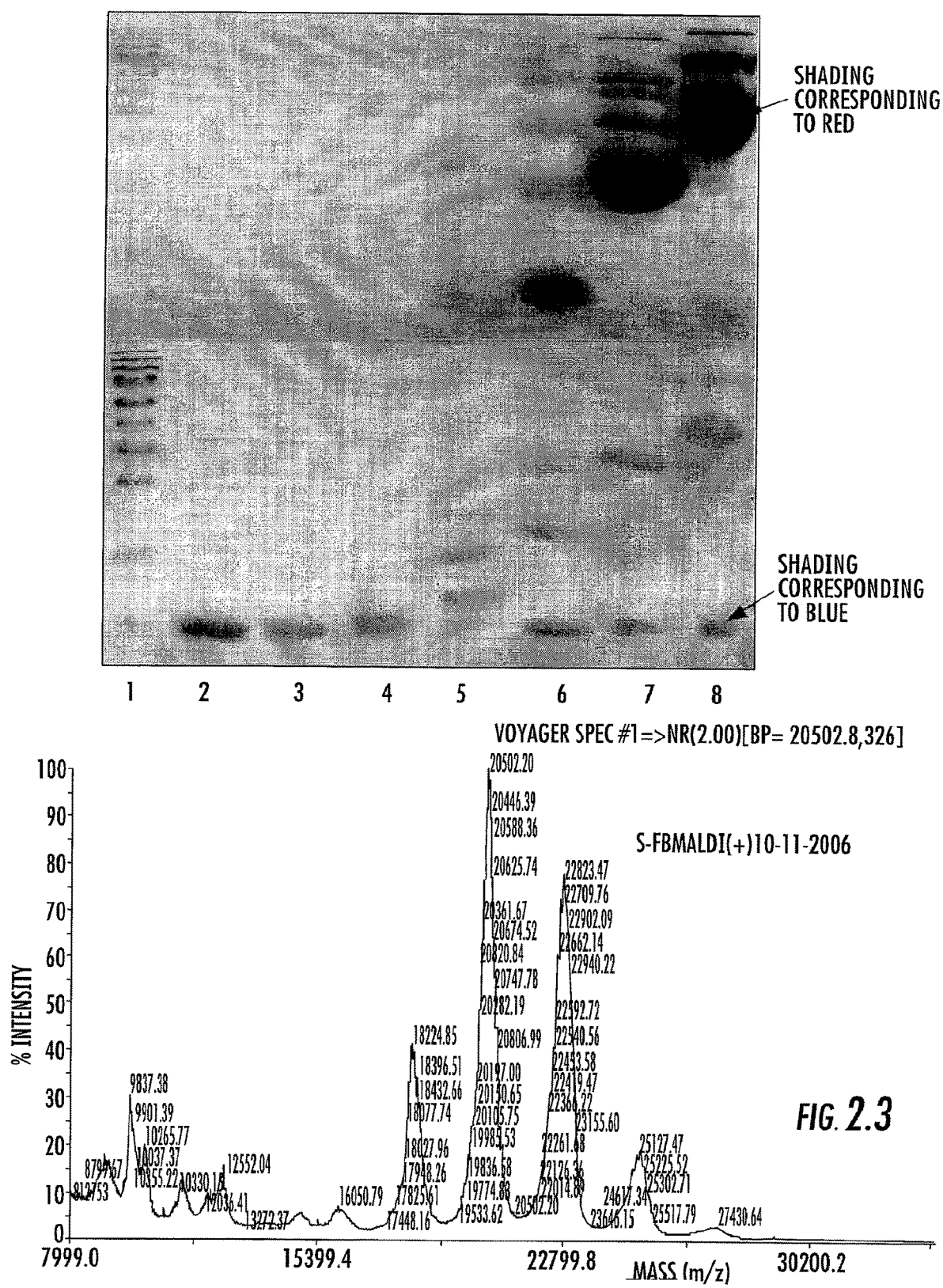
FIG. 2.3

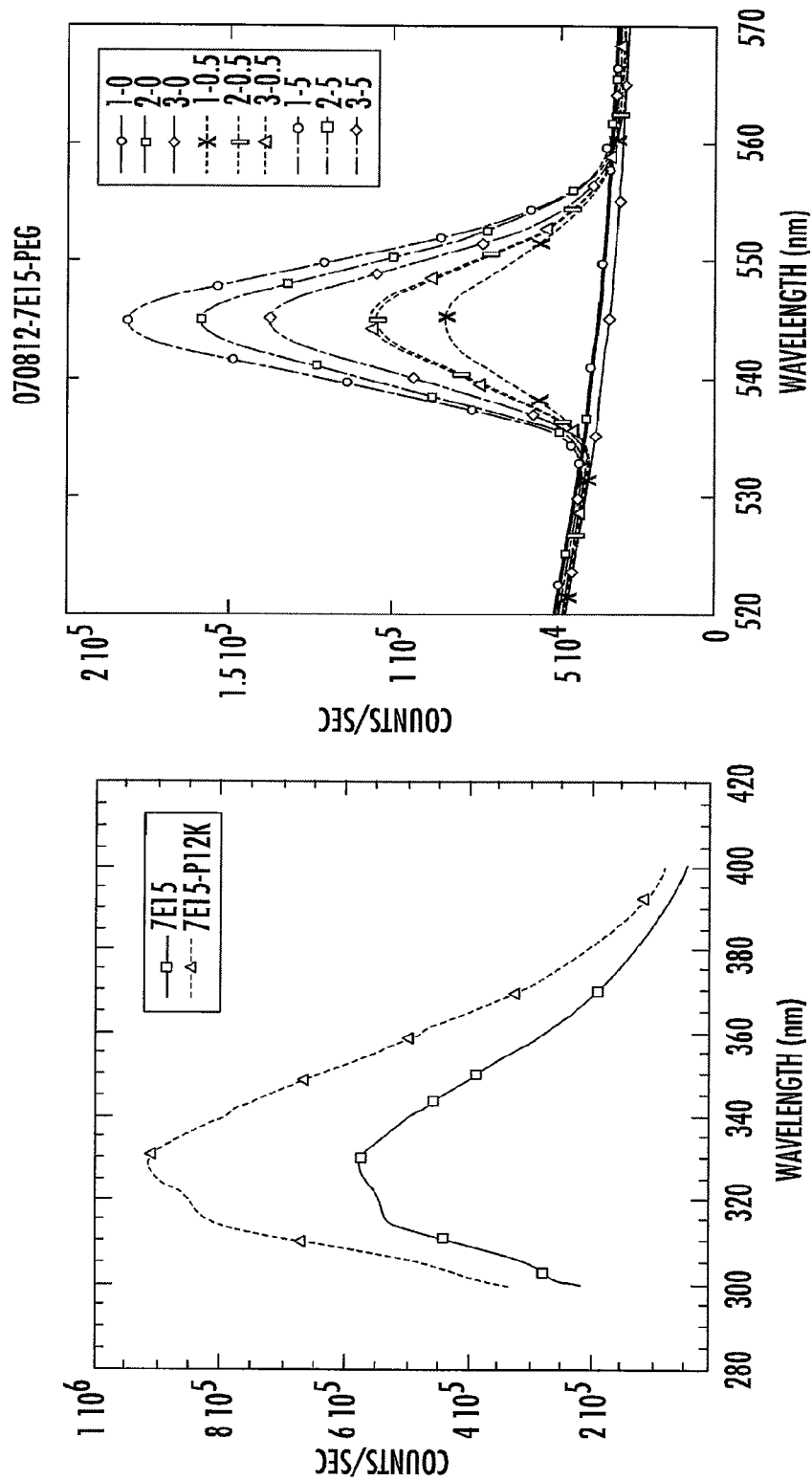
FIG. 2.4

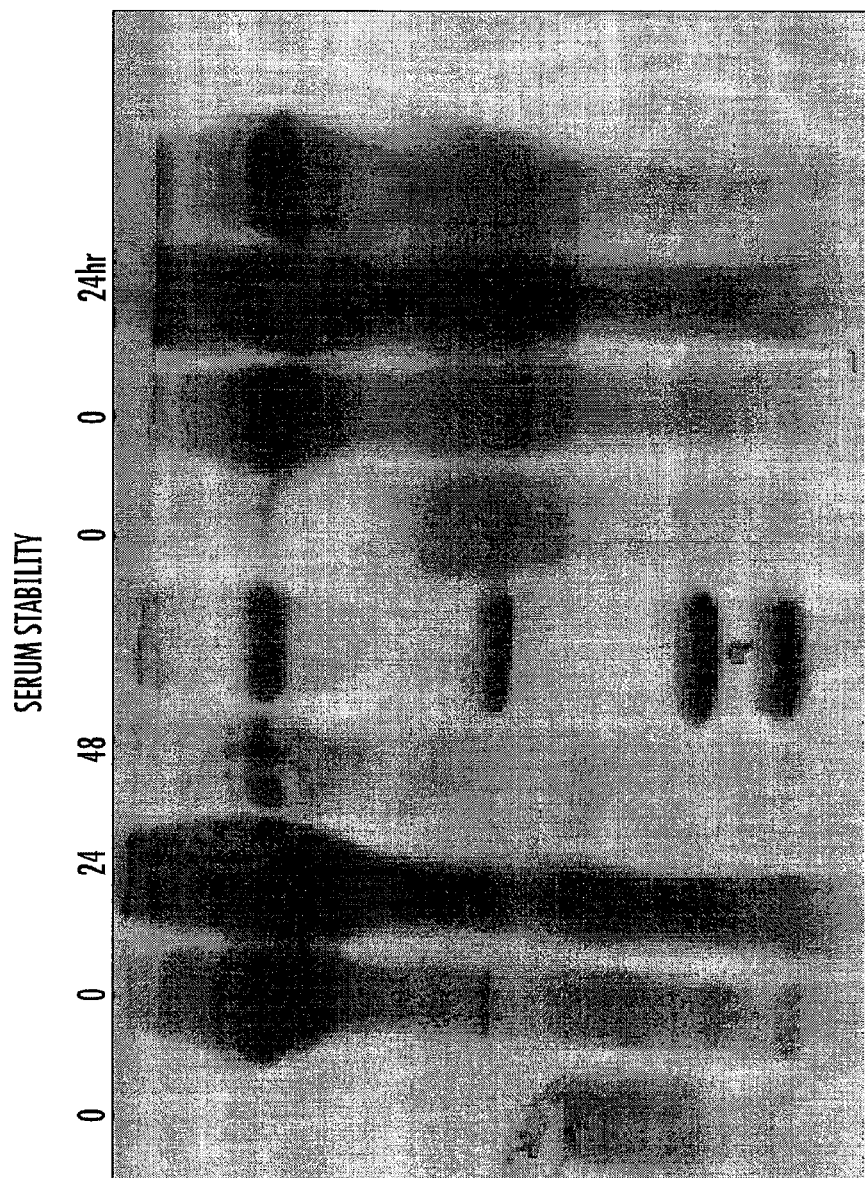
FIG. 2.5

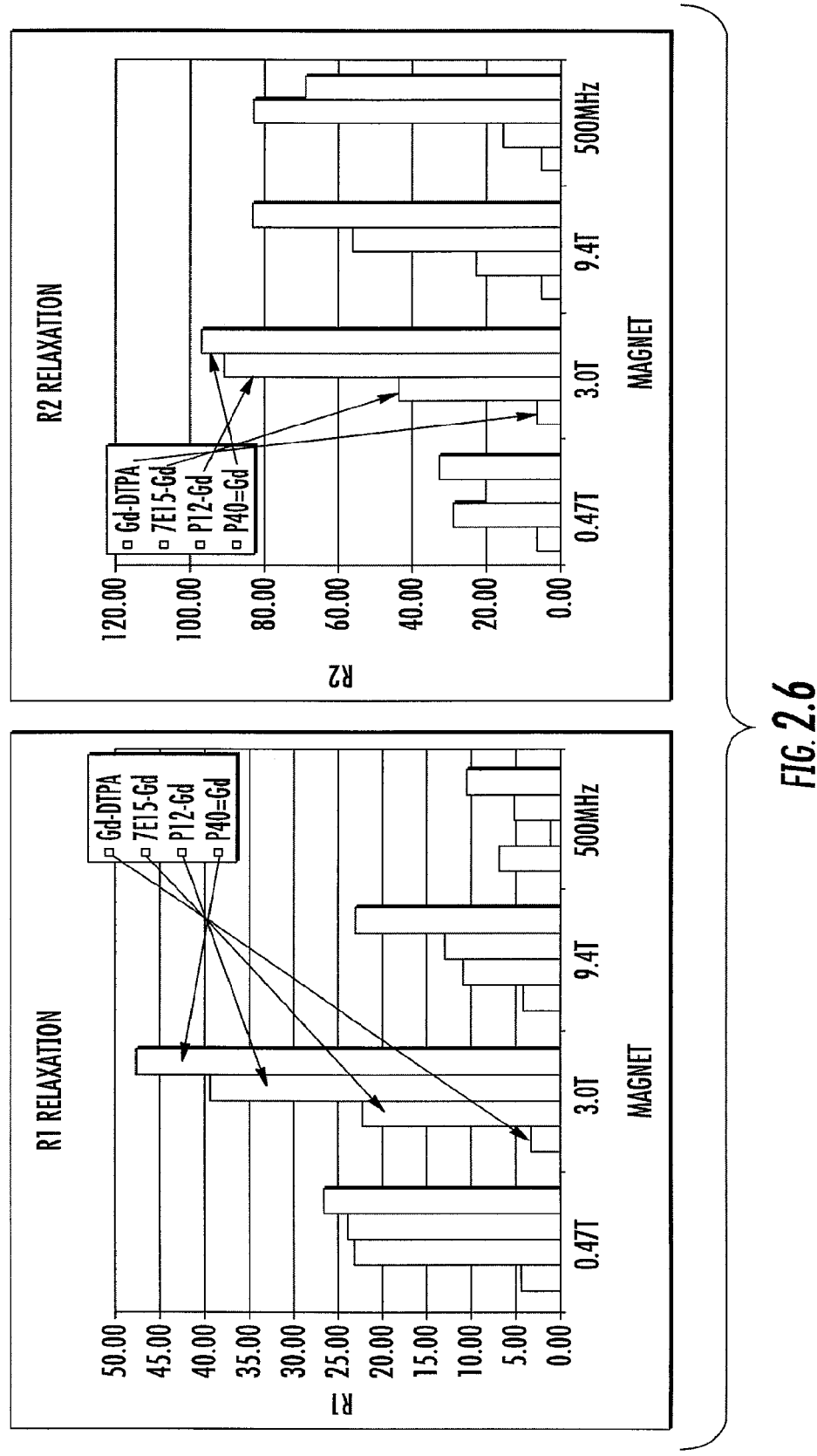
FIG. 2.6

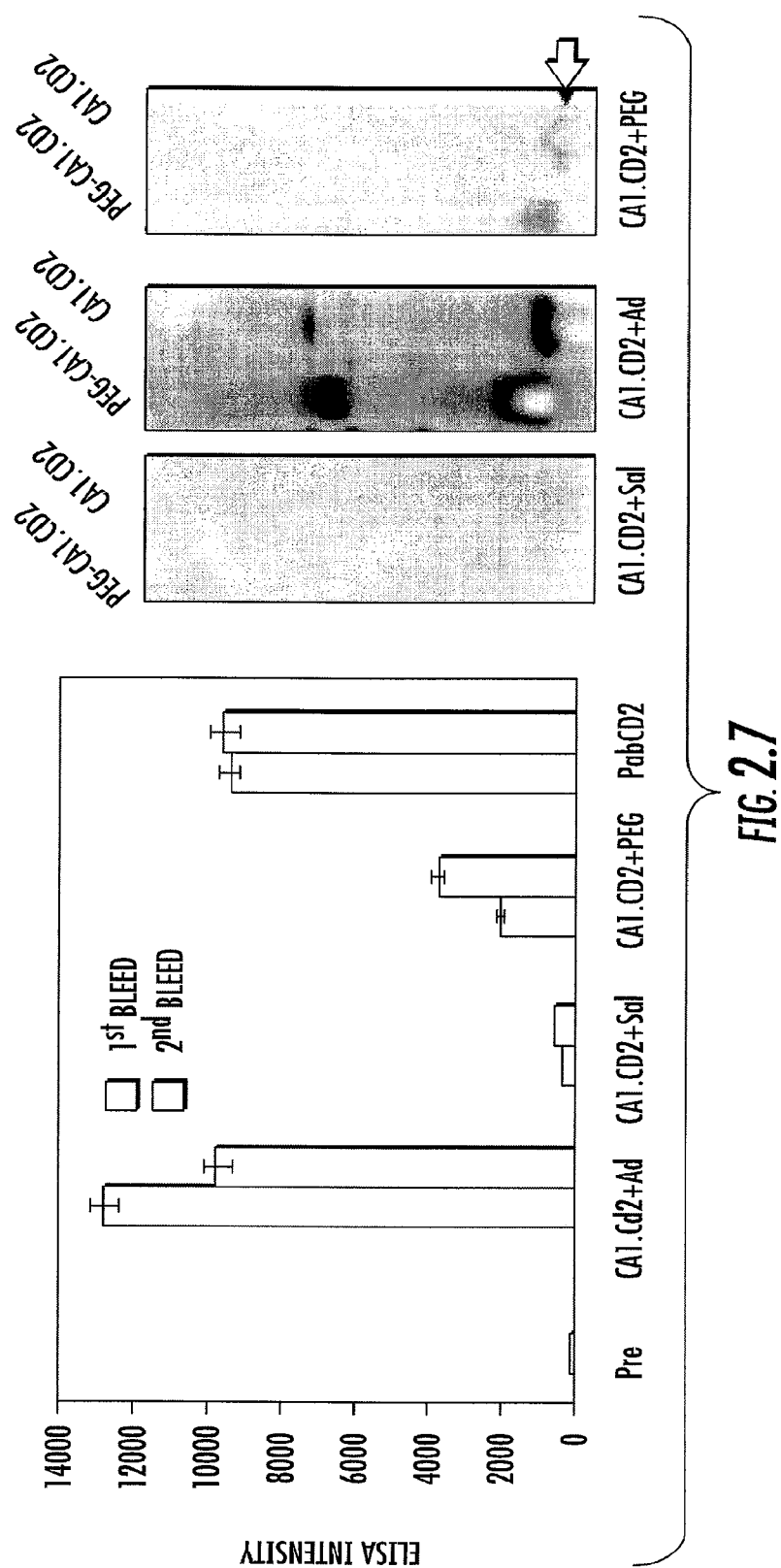
FIG. 2.7

| PROTEIN | kobs(H$_2$O), us$^{-1}$ | kobs(D$_2$O), us$^{-1}$ | WATER NUMBER |
|---|---|---|---|
| CA1.CD2 | 0.0009192 | 0.000354 | 2.38 |
| CA1.CD2 P12 | 0.001116 | 0.000354 | 3.21 |
| CA1.CD2 P40 | 0.001073 | 0.0003556 | 3.02 |
| CA1.CD2 P12k | 0.0009759 | 0.0003484 | 2.65 |
| FREE-Tb | 0.002172 | 0.0002223 | 8.21 |
$$n_{H2O} = 1000 \times 4.216 \times (k_{obs(H2O)} - k_{obs(D2O)})$$
FIG. 2.8
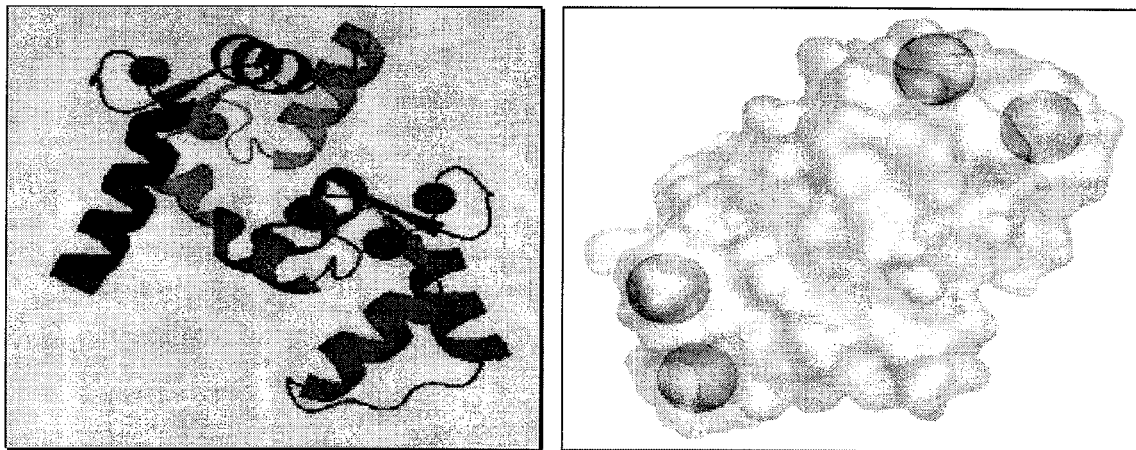
FIG. 3.1

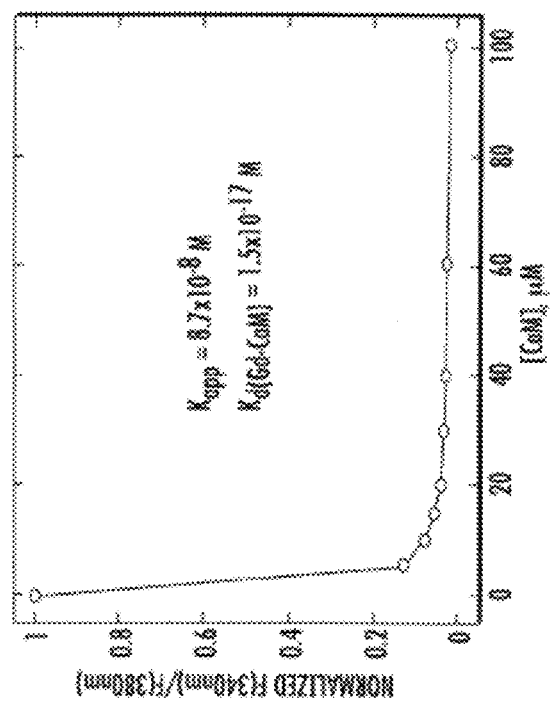
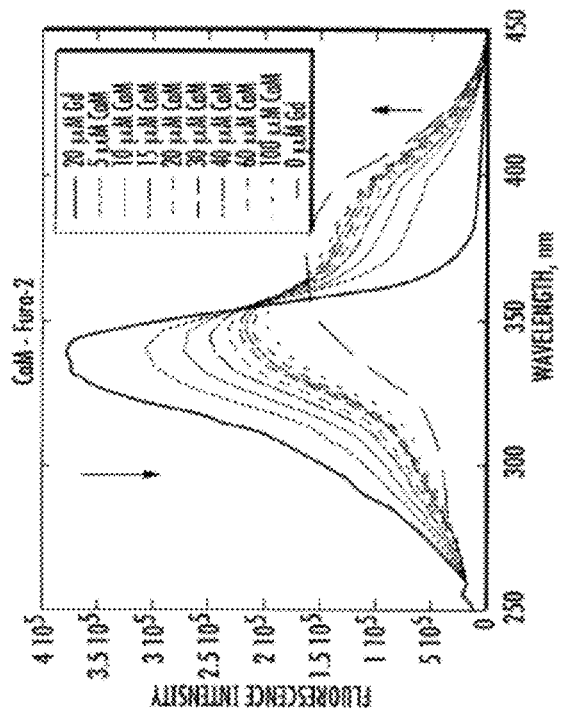
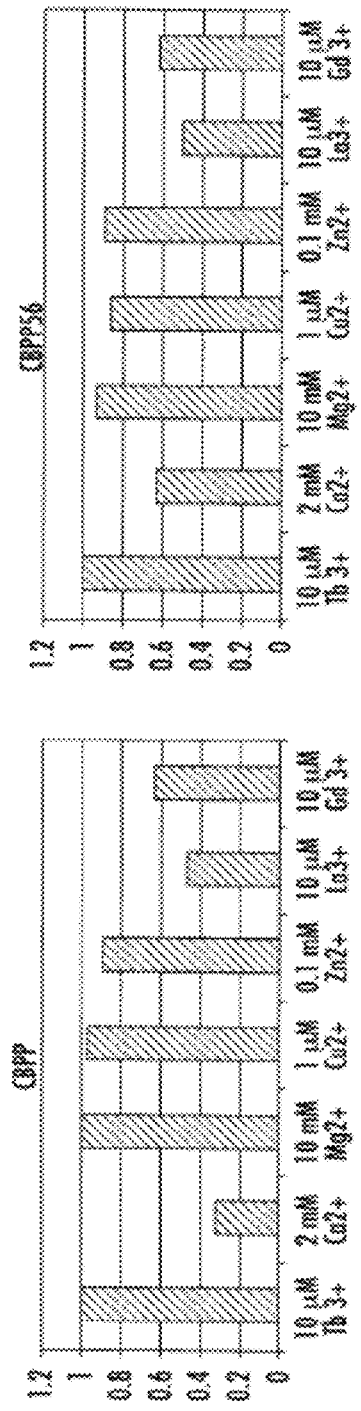
Fig. 3.2A
Fig. 3.2B
Fig. 3.2C

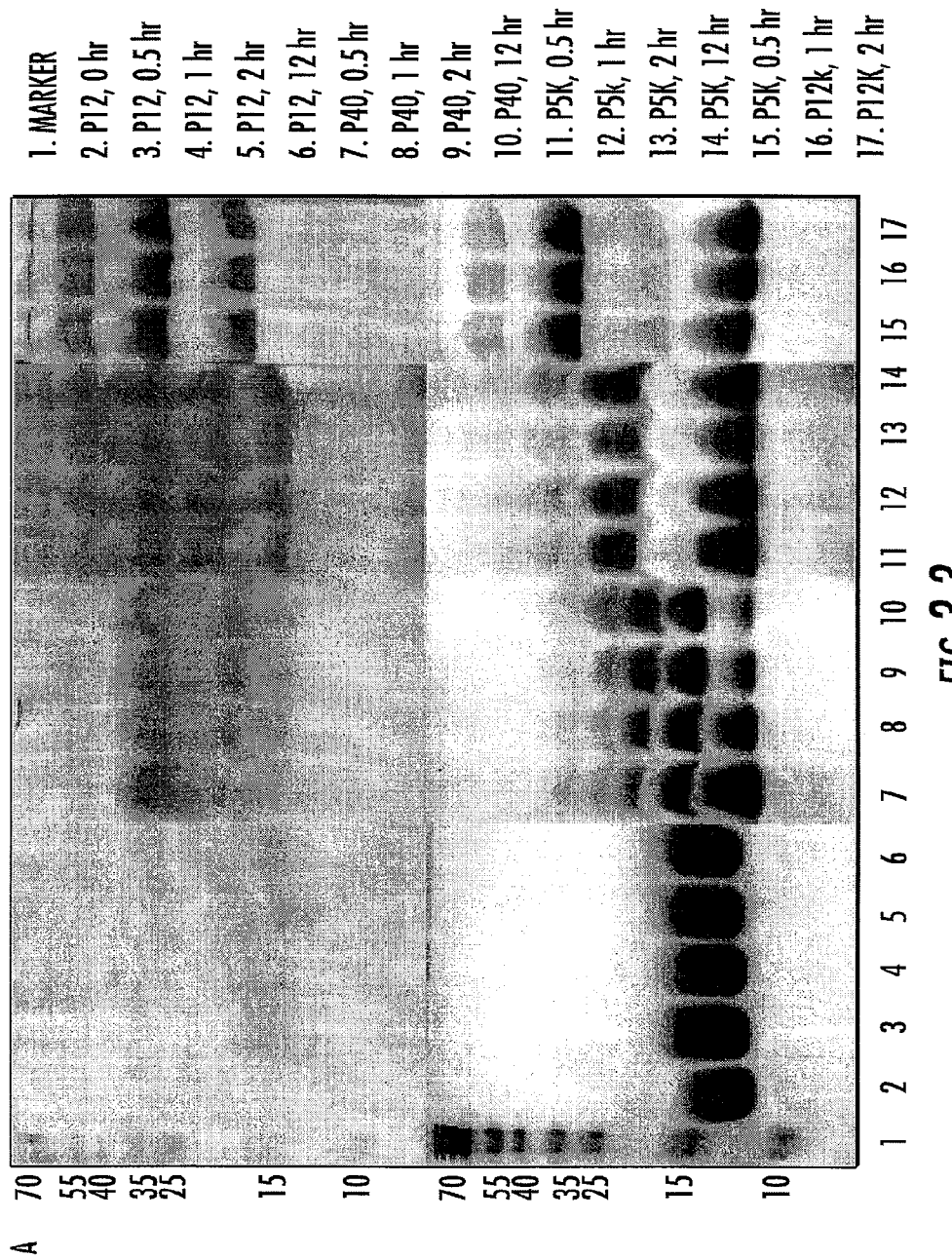
FIG. 3.3

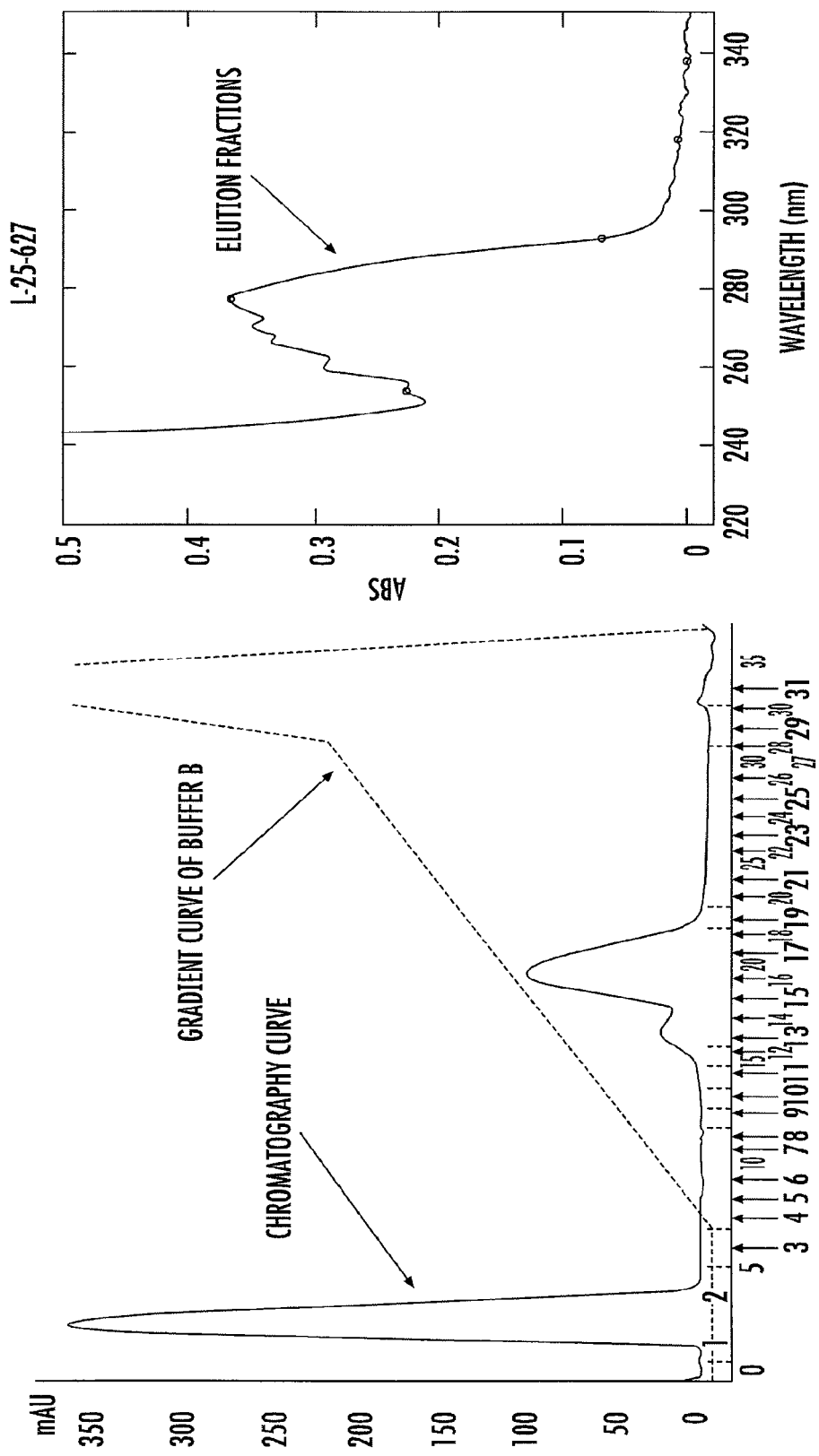
FIG. 3.4

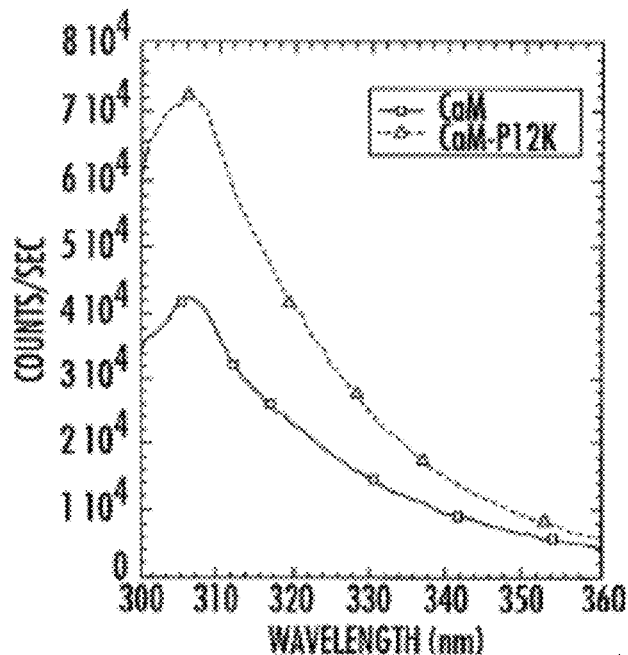
Fig. 3.5A
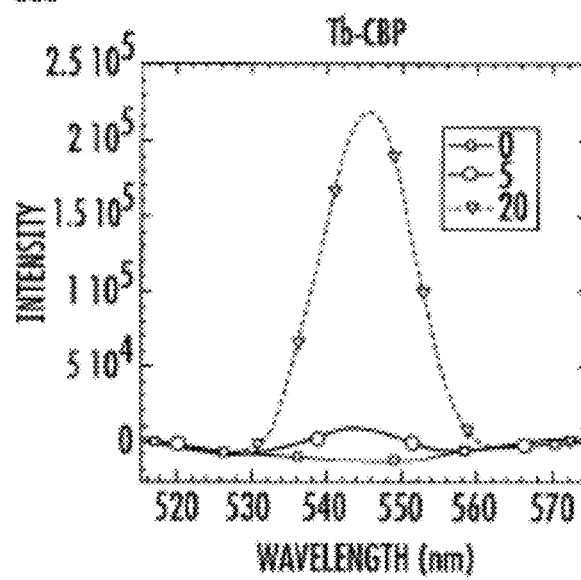
Fig. 3.5B
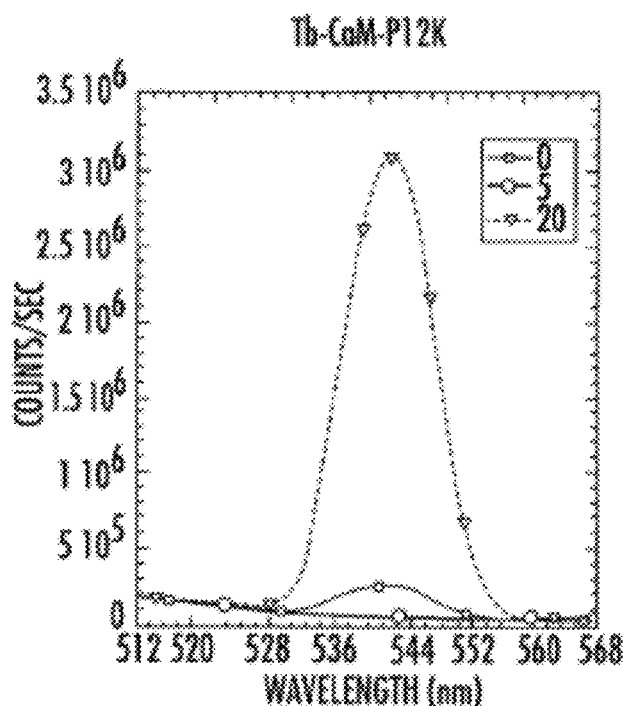
Fig. 3.5C

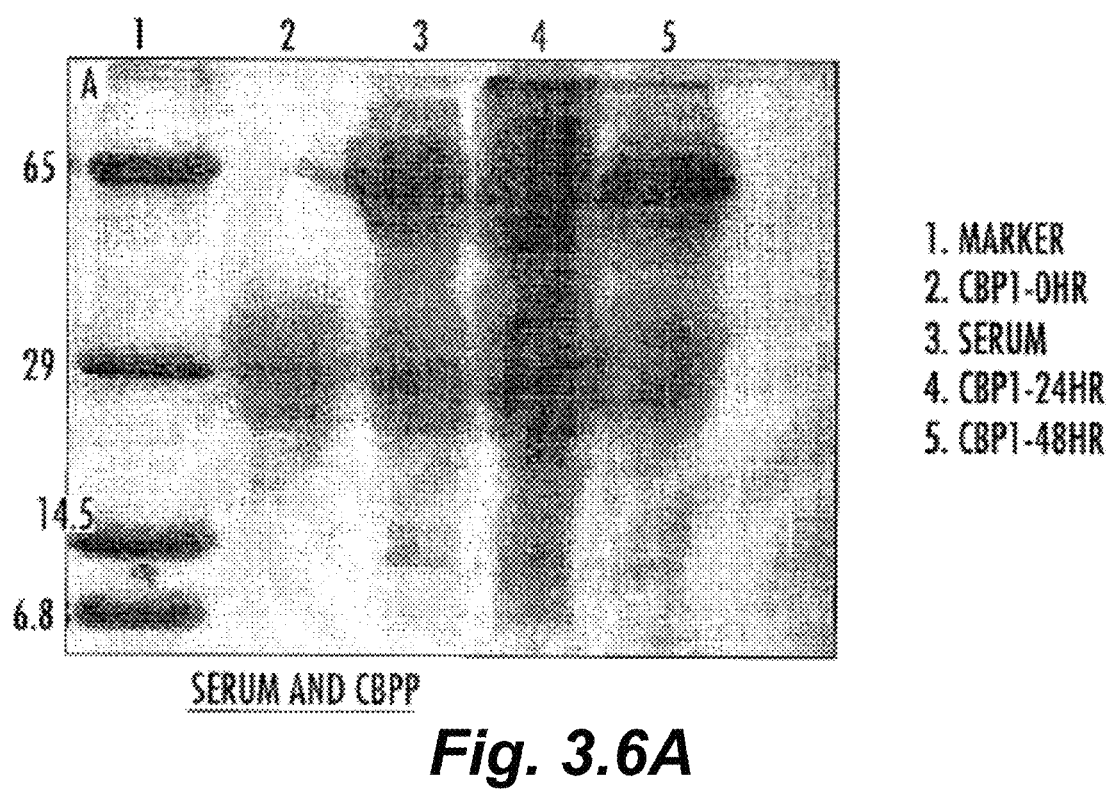
1. MARKER
2. CBP1-0HR
3. SERUM
4. CBP1-24HR
5. CBP1-48HR
SERUM AND CBPP
*Fig. 3.6A*
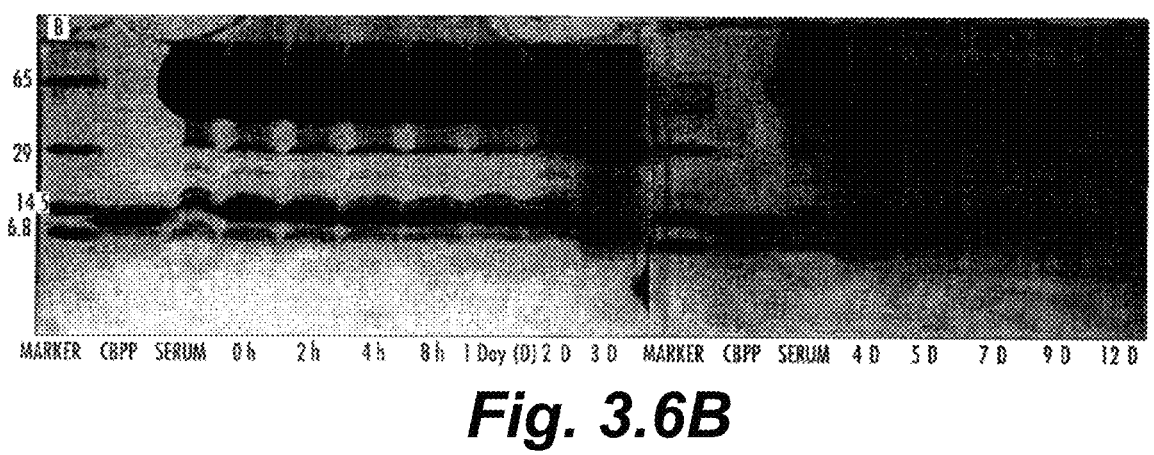
*Fig. 3.6B*

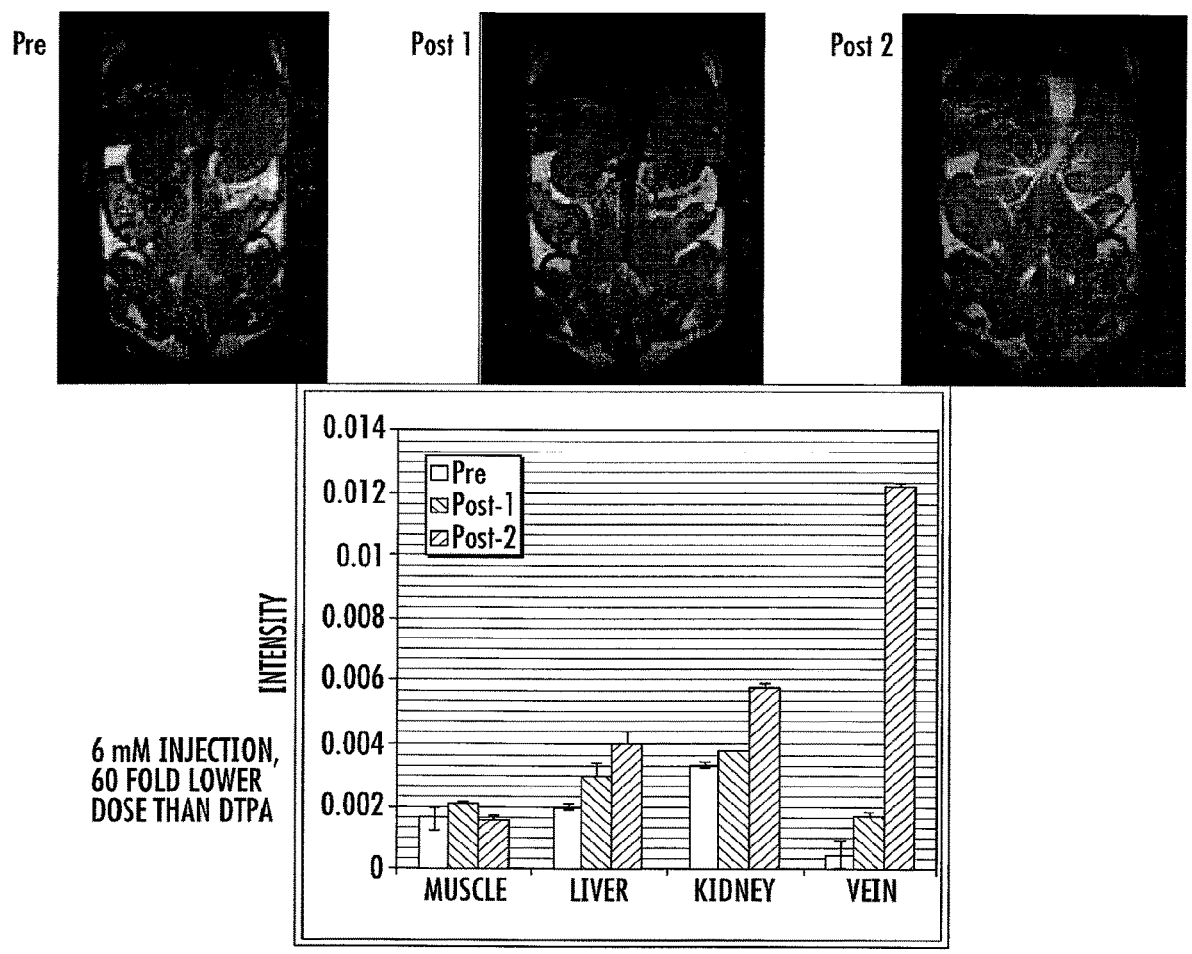
FIG. 3.7

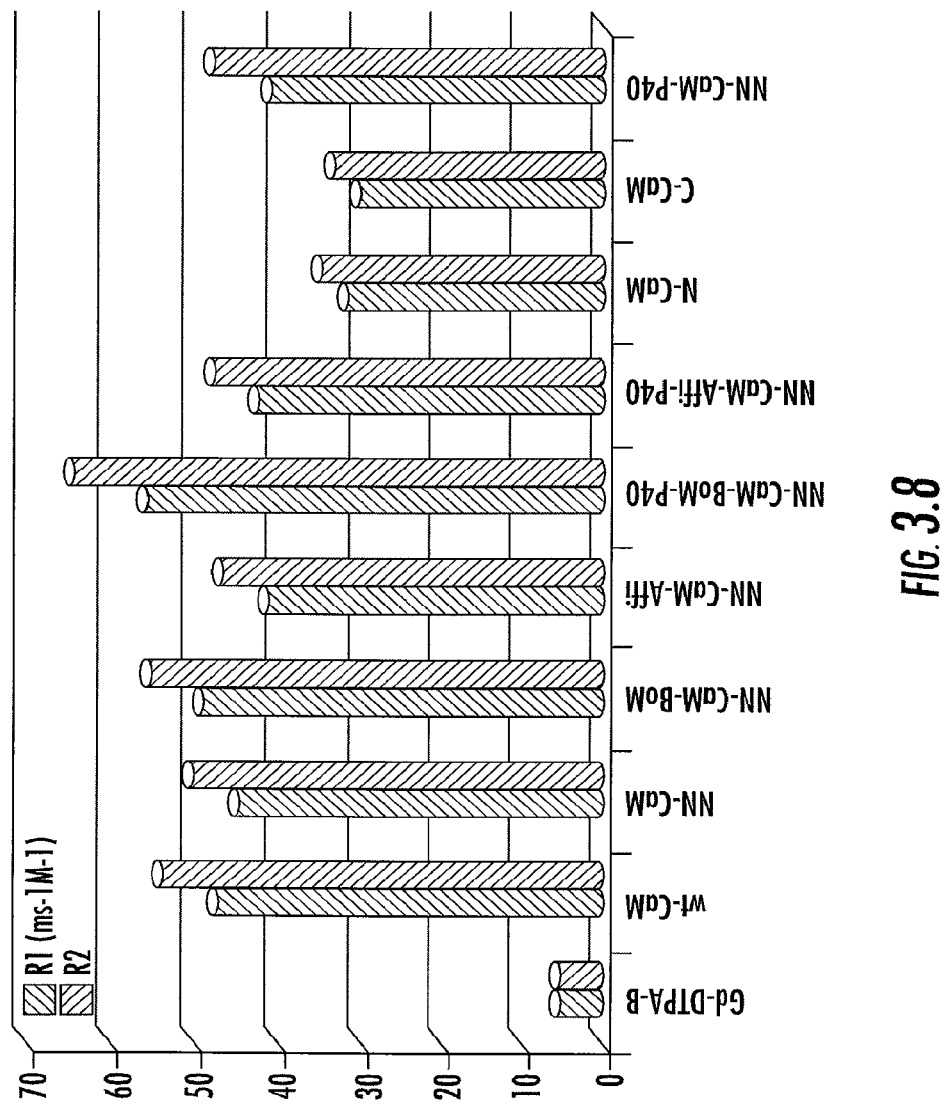
FIG. 3.8

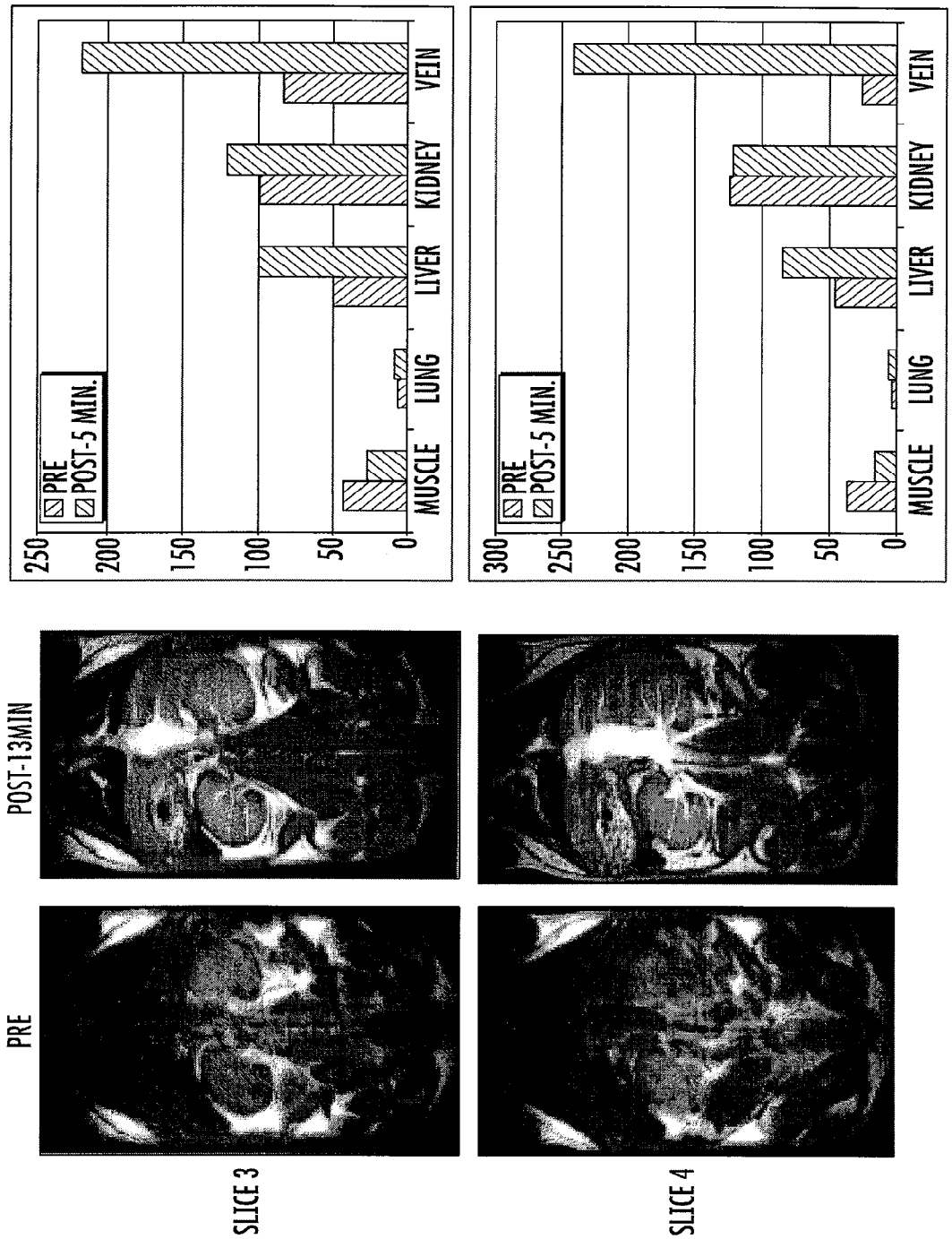
FIG. 3.9

| $K_d$ | $Ca^{2+}$ (M) | $Tb^{3+}$ (M) | $Gd^{3+}$ (M) |
|---|---|---|---|
| CBP1 | 3.64 ± 0.03 E-06 | 7.0 ± 0.01 E-12 | 1.1 ± 0.03 E-11 |
| CBP1-DD | 1.64 ± 0.02 E-06 | 6.9 ± 0.04 E-12 | 8.7 ± 0.06 E-12 |
| ΔCaM-DD | 1.47 ± 0.03 E-06 | 4.5 ± 0.06 E-12 | 3.4 ± 0.12 E-12 |
| CBPP | 3.91 ± 0.96 E-09 | 4.50 ± 0.28 E-12 | – |
| CBPP55 | 3.57 ± 0.01 E-09 | 1.55 ± 0.29 E-18 | 1.66 E-18 |
| CBPP59 | 1.05 ± 0.09 E-08 | 5.34 ± 0.34 E-12 | – |

The dissociation constant of $Ca^{2+}$, $Tb^{3+}$ and $Gd^{3+}$ to CBPP were measured by Fluorescence spectroscopy. To determine the $Ca^{2+}$ and $Gd^{3+}$ dissociation constant, the intrinsic tryptophan fluorescence change were used to monitor the binding process between CBP1/CBPP and metal. The free metal concentration were controlled by the metal-EGTA buffer system and calculated by $[Metal]_{free} = kd*[EGTA\text{-}metal]/[EGTA]_{free}$. The aromatic residue-sensitized $Tb^{3+}$ fluorescence at 545 nm were applied to monitor the process of $Tb^{3+}$ binding to CBP1/CBPP and the variants.

FIG. 3.10

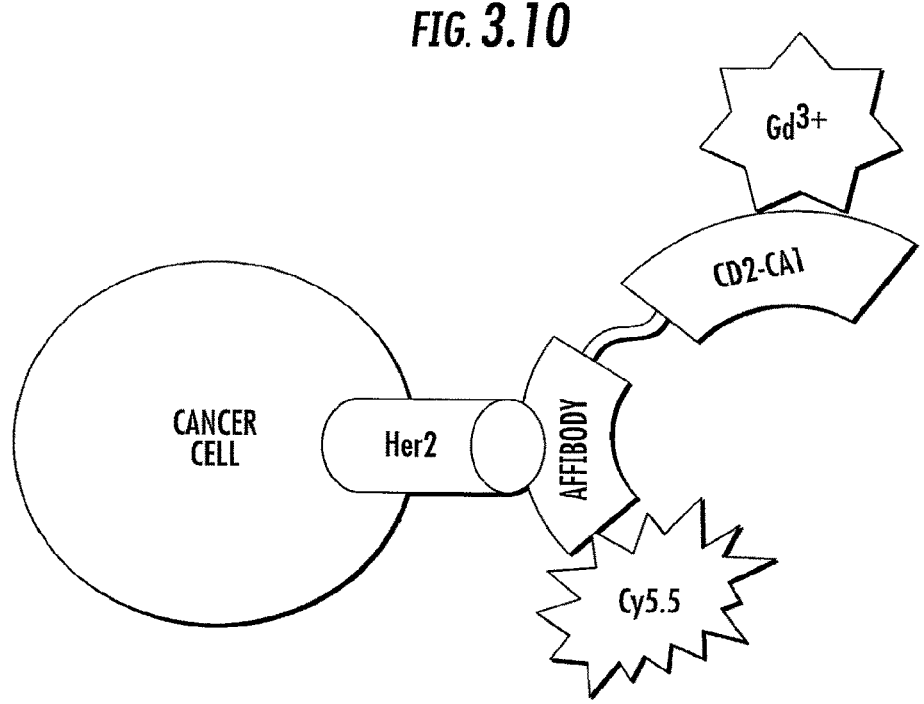

FIG. 4.1

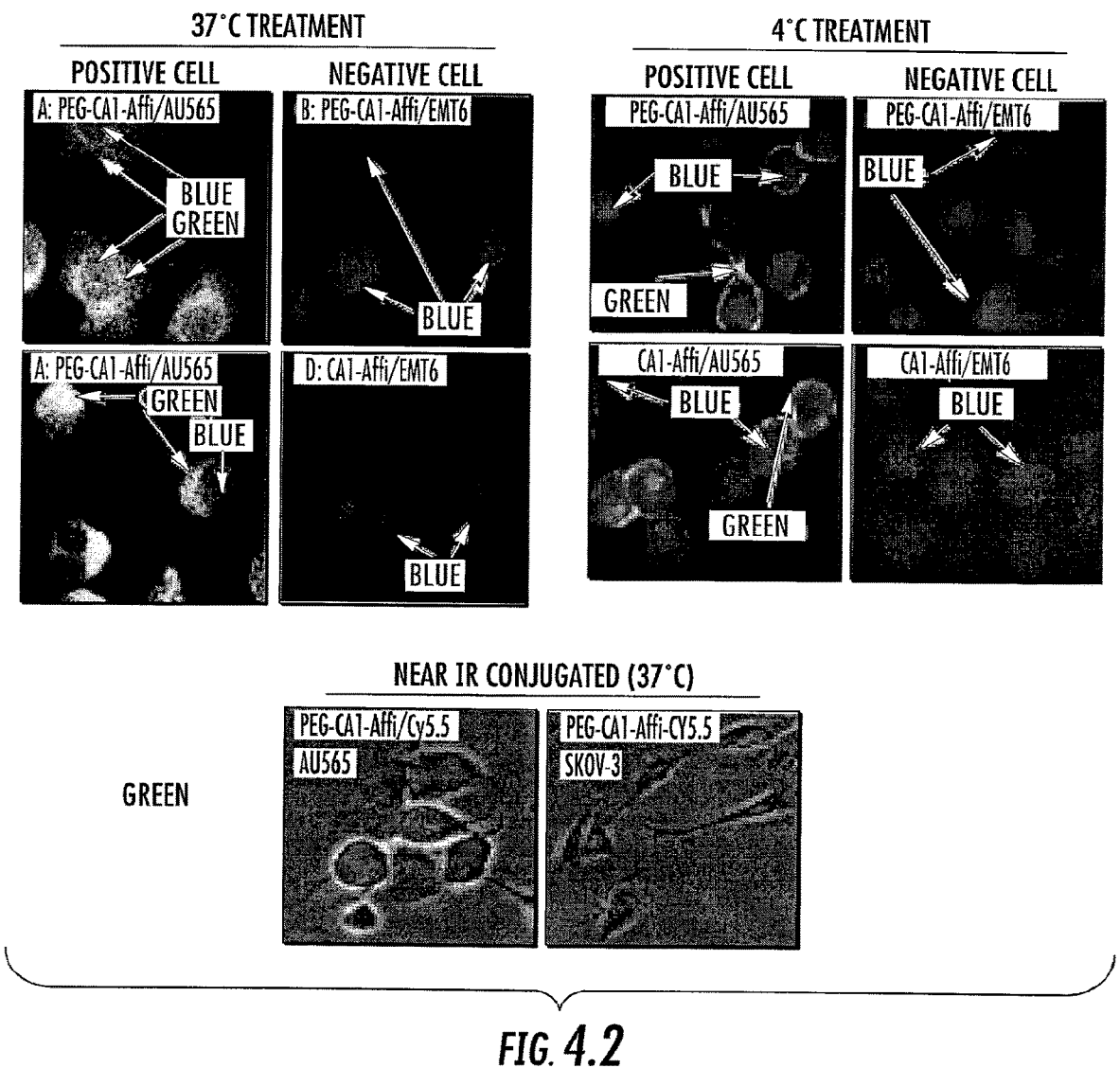
FIG. 4.2

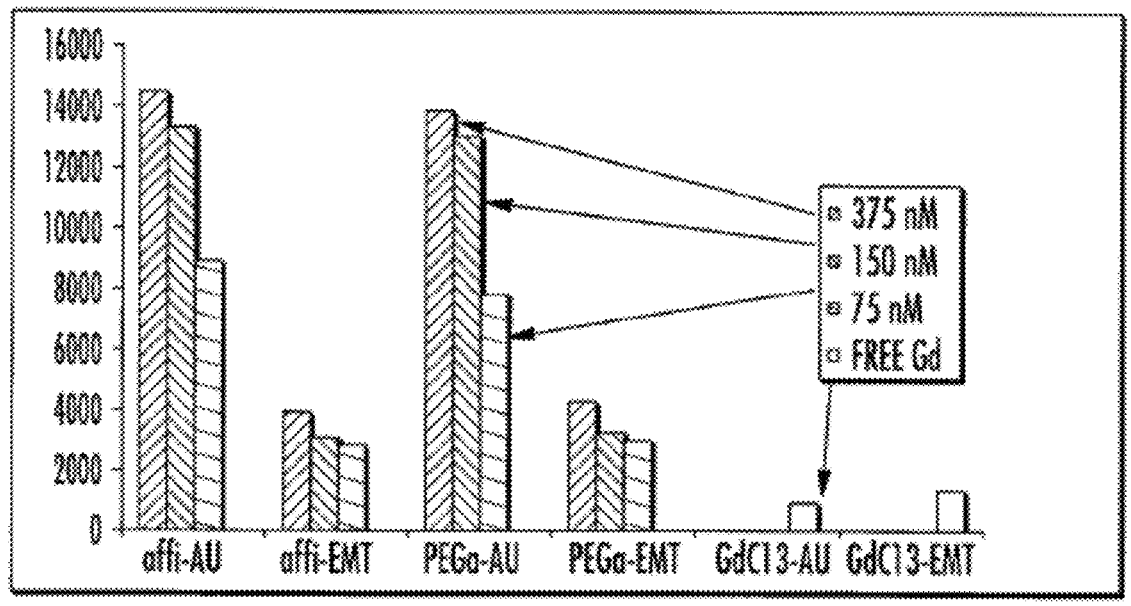
*Fig. 4.3A*
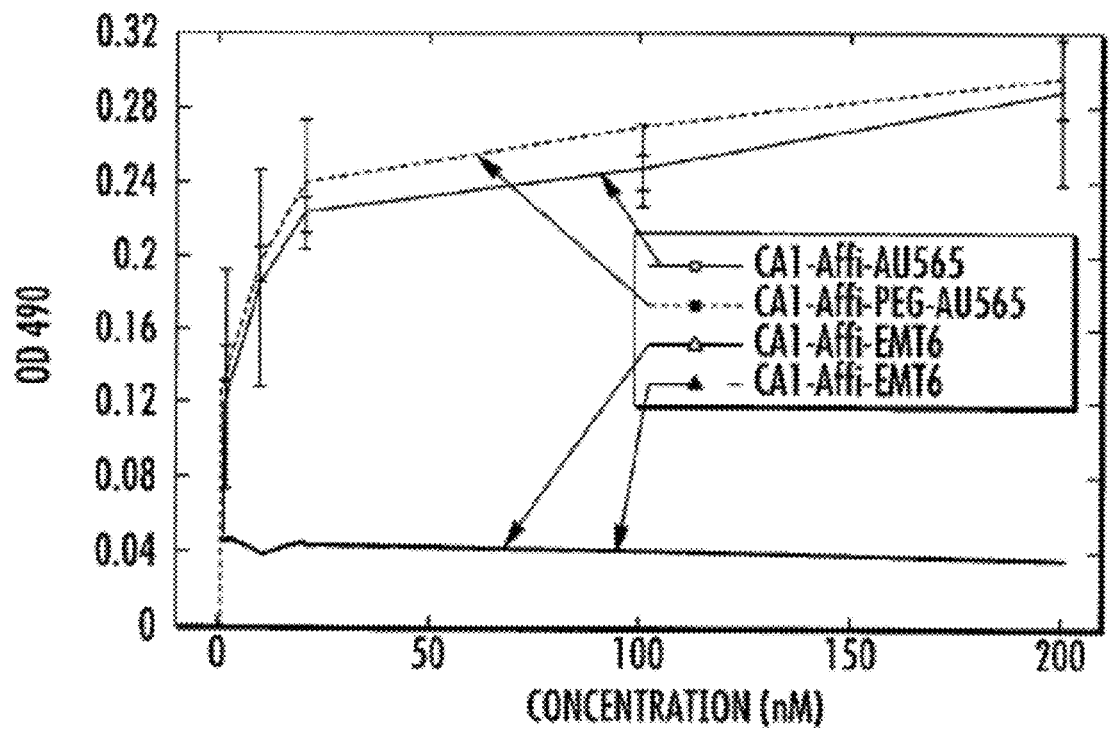
*Fig. 4.3B*

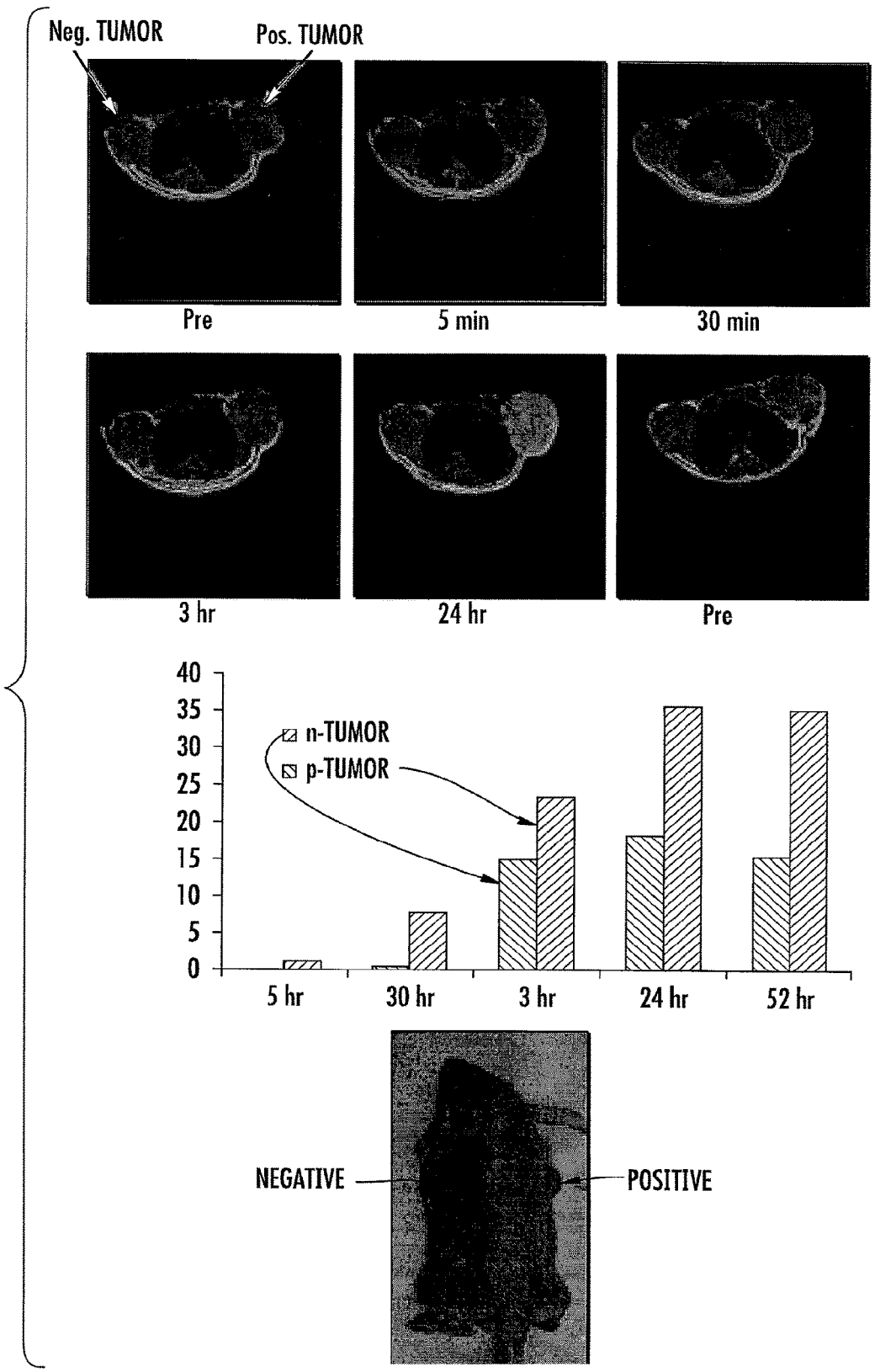
FIG. 4.4

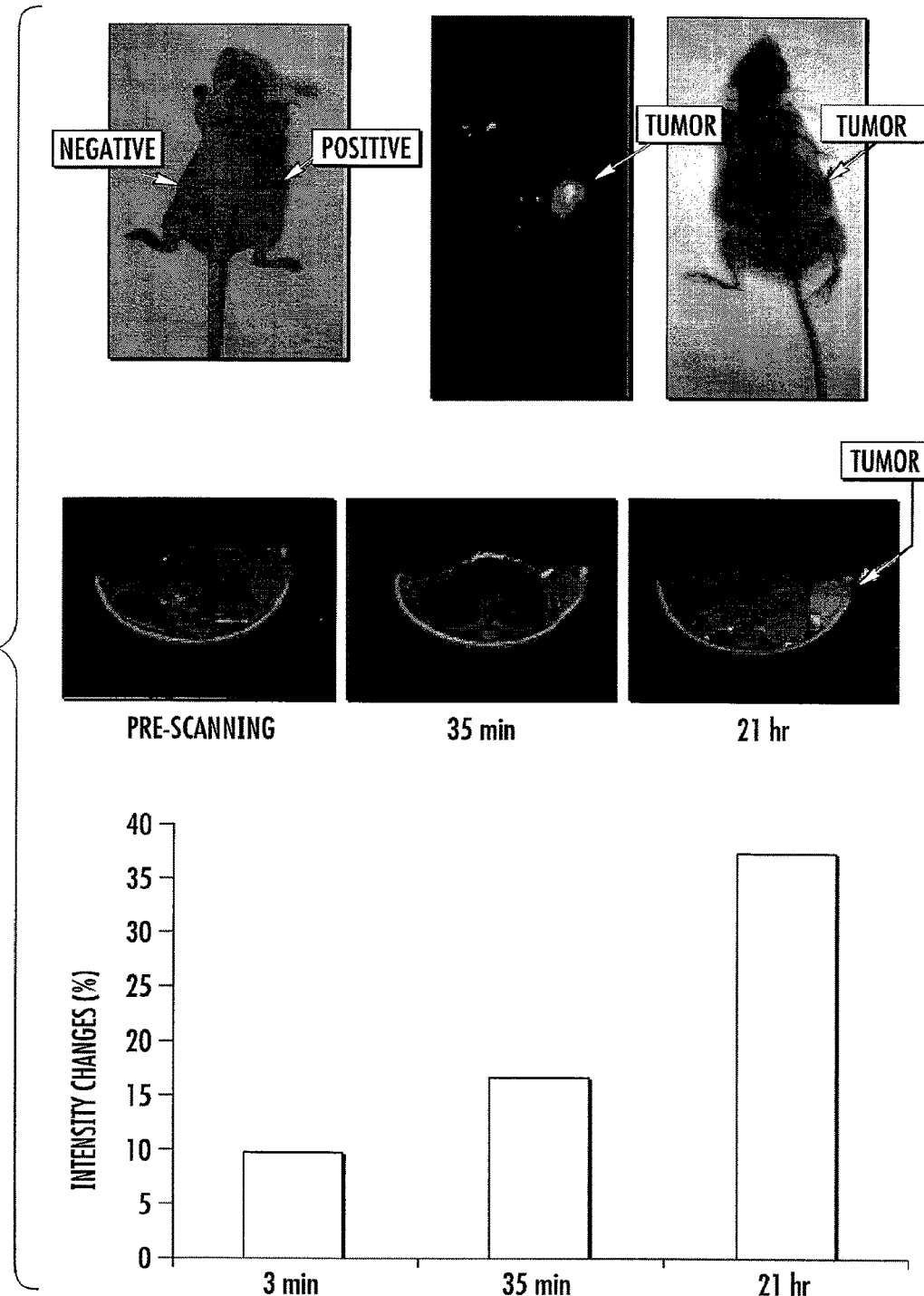
FIG. 4.5

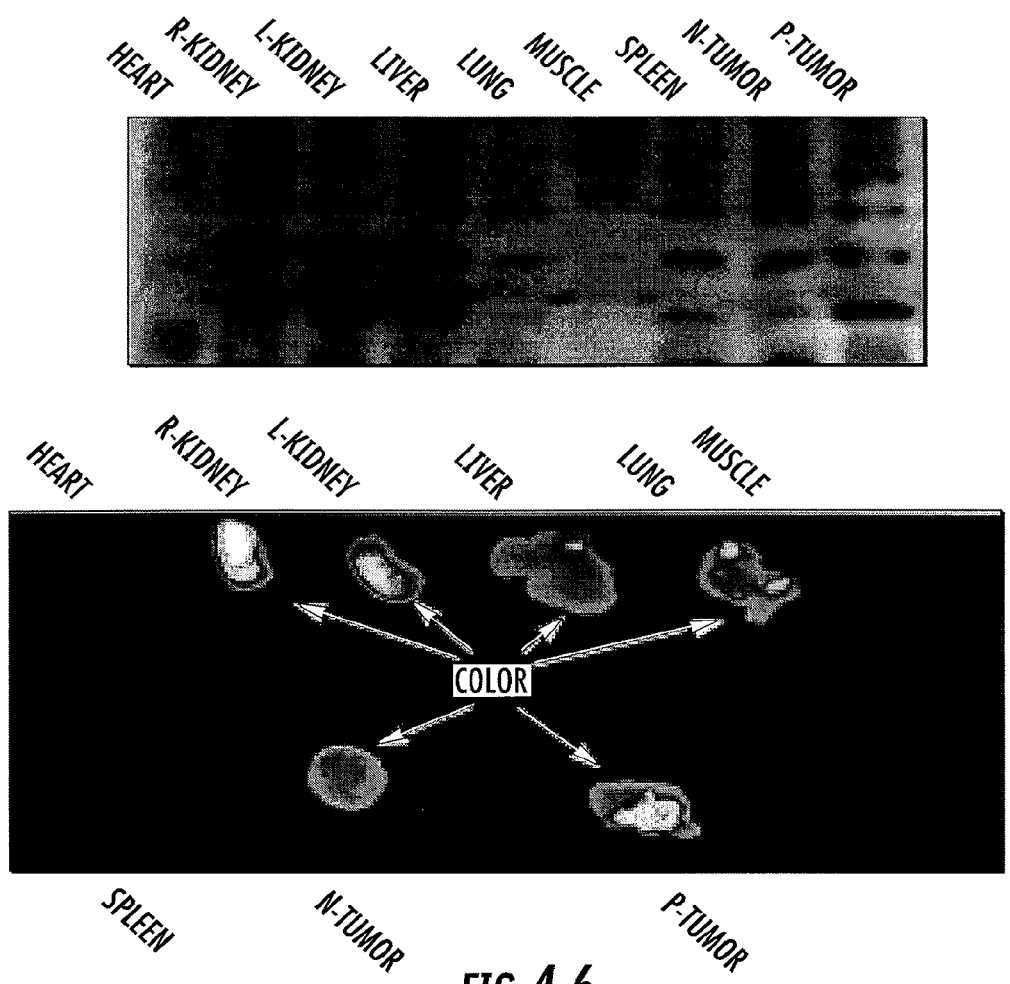
FIG. 4.6
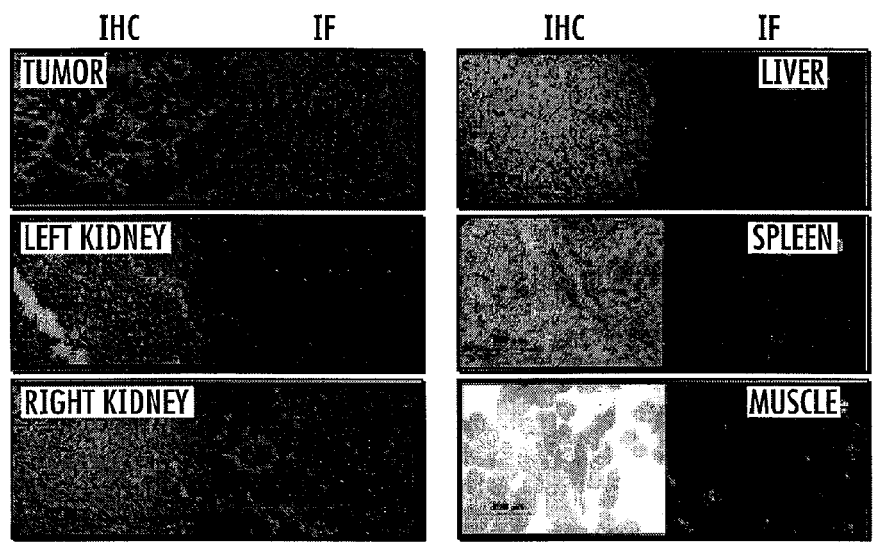
FIG. 4.7

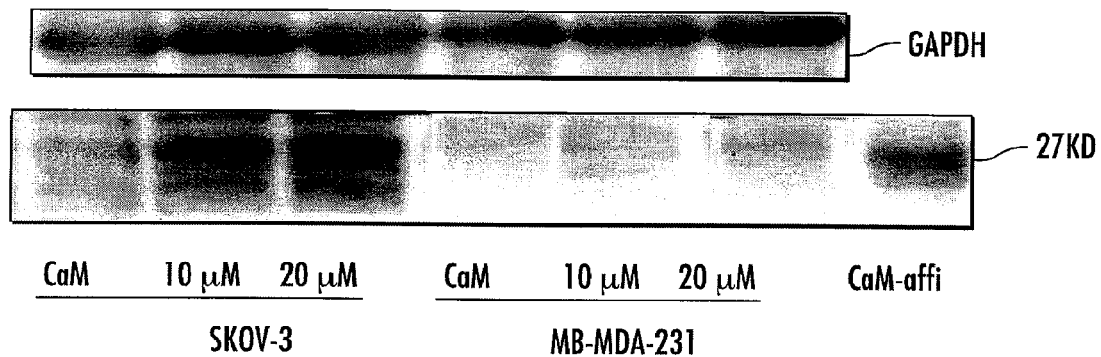
FIG. 4.8
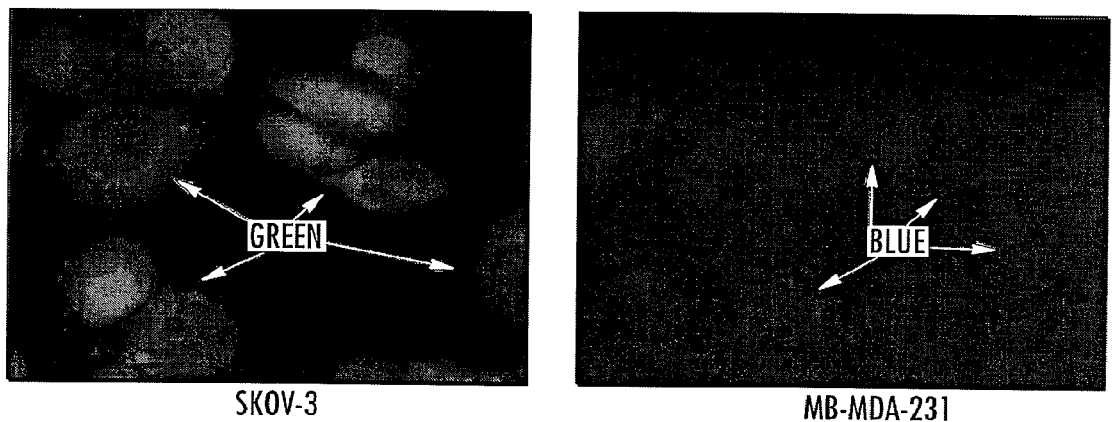
FIG. 4.9

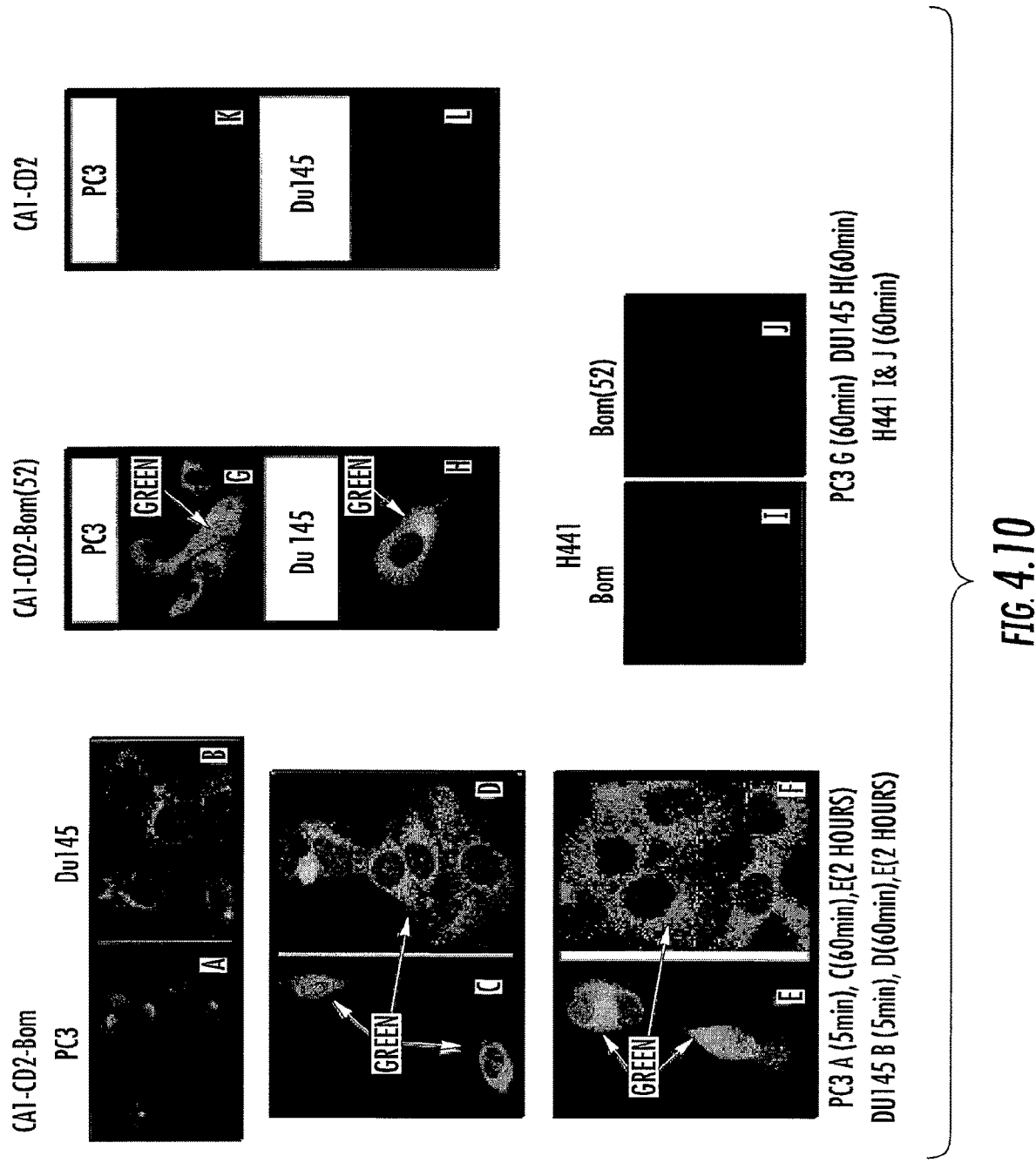
FIG. 4.10

FLUORESCENT IMAGING
AFTER INJECTION 26 hrs
DU-145
H441
FIG. 4.11

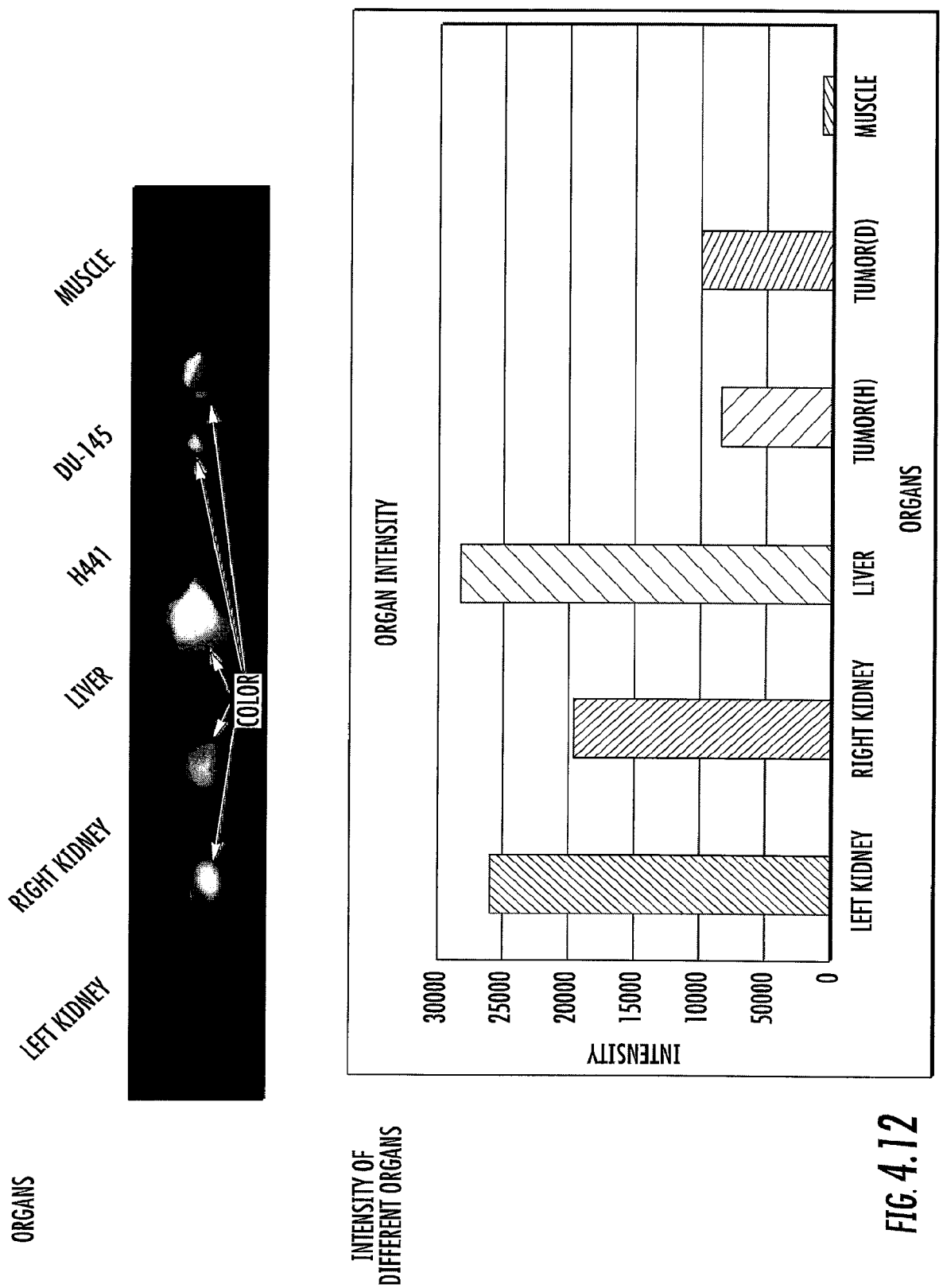
FIG. 4.12

CONTRAST AGENTS, METHODS FOR PREPARING CONTRAST AGENTS, AND METHODS OF IMAGING

CROSS-REFERENCE TO RELATED APPLICATION

This application is a continuation of, and claims priority to, co-pending U.S. patent application Ser. No. 12/935,413, filed on Dec. 22, 2010, which is incorporated by reference in its entirety. This application also claims priority to and benefit of PCT application entitled "CONTRAST AGENTS, METHODS FOR PREPARING CONTRAST AGENTS AND METHODS OF IMAGING," having serial number PCT/US2009/039276, filed on Apr. 2, 2009. This application also claims priority to and benefit of U.S. Provisional Patent Application No. 61/041,693, filed on Apr. 2, 2008, which is incorporated by reference in its entirety.

BACKGROUND

Magnetic resonance imaging (MRI) is a non-invasive technique providing high resolution, three-dimensional images of morphological features as well as functional and physiological information about tissues in vivo. It is capable of detecting abnormalities in deep tissues and allows for whole body imaging. It has emerged as a primary diagnostic imaging technique for human diseases.

Exogenous MRI contrast agents are often used to enhance the contrast between pathological and normal tissues by altering the longitudinal and transverse (i.e., $T_1$ and $T_2$) relaxation times of water protons. The relaxivity (unit capability of the agent to change the relaxation time) of a contrast agent is dependent on several factors including the number of water molecules in the coordination shell, the exchange rate of the coordinated water with the bulk water, and the rotational correlation time $\tau_R$ of the contrast agent. The MRI contrast agent can have: 1) high relaxivity for high contrast-to-noise ratio (CNR) and dose efficiency, 2) thermodynamic stability, especially metal selectivity for the target ions over excess physiological metal ions, to minimize the release of toxic paramagnetic metal ions, 3) adequate vascular, tissue retention time to allow imaging, and 4) proper excretion from the body. There is a need in the art to meet some or all of these properties.

SUMMARY

Embodiments of the present disclosure provide for contrast agents, methods of making contrast agents, and methods of using contrast agents, and the like. One exemplary contrast agent, among others, includes: a) a scaffold protein, and b) at least one metal ion chelating site, wherein the scaffold protein includes at least one metal ion chelating site that is already present or is integrated into the scaffold protein, wherein the scaffold protein includes a metal ion bound to a metal ion chelating site, wherein the contrast agent is stable in a physiological environment.

One exemplary method of imaging a sample, among others, includes: administering at least one of the contrast agent described herein to the sample; introducing the sample to an imaging system; and imaging the sample.

One exemplary method for preparing a contrast agent, among others, includes: a) selecting a scaffold protein; b) constructing at least one metal ion chelating site; c) operatively embedding the metal ion binding site into the protein, wherein the metal ion has contrast agent properties, and d) attaching at least one polyethylene glycol (PEG) to the scaffold protein.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

drawings, like reference numerals designate corresponding parts throughout the several views.

FIGS. 1.1A-1.1C: Schematic descriptions of different classes of MRI contrast agents and simulation of Tj relaxivity.

FIG. 1.1A: Different constructs of MRI contrast agents, (i) Small chelator DPTA with a fast $T_R$ ($\tau_{Rf}$) at ~100 ps level; (ii) Small contrast agents after being covalently conjugated to macromolecules with a slow $\tau_R$ ($T_{RS}$) still possess a fast $\tau_R$ due to its internal mobility; (iii) Schematic description of the design of reported MRI contrast agents by directly coordinating $Gd^{3+}$ ions to ligand residues on a rigid protein frame to eliminate the high internal mobility. The rotational correlation time of the $Gd^{3+}$ binding site is the same as that of the whole protein ($T_{RS}$).

FIG. 1.1B: Simulated Ti relaxivity at the given rotational correlation time $\tau_R$ (100 ps, below, or 10 ns, above), water dwelling time $\tau_m$, correlation time of splitting $\tau_v$ (1 and 10 ps, solid and dashed lines, respectively), and mean square zero field splitting energy $\Delta^2$ ($10^{18}$ s$^{-2}$). The $\tau_m$ valves are $10^{-10}$ (o), $10^{-9}$ (G), and $10^{-8}$ s ($\Delta$) for 100 ps $\tau_R$ and $10^{-9}$ (•), $10^{-8}$ (■), and $10^{-7}$ s (A) for 10 ns $\tau_R$ according to the theory developed by Blombergen, Solomon (refs 6 and 7 in Example 1). The water coordination number, q, is assumed to be 1 and the agent concentration is 0.001 M. See on-line supporting materials for r1 and r2 simulations.

FIG. 1.1C: Modeled structure of designed $Gd^{3+}$-CA1. CD2 based on the designed NMR structure 1T6W (ref 31 in Example 1). Ligand residues E15, E56, D58, D62 and D64 at the B, E, and D β-strands of the host protein CD2 are shown in red.

FIGS. 1.2A-1.2C: Comparison of in vitro relaxivity between DTPA and designed contrast agents.

FIG. 1.2A: MR images produced using Spin-echo sequence, TR 6000 ms, TI 960 ms, TE 7.6 ms at 3T. Samples are 1) $dH_2O$, 2) 10 mM Tris-HCl pH 7.4, 3) 0.10 mM Gd-DTPA in $H_2O$, 4) 0.10 mM Gd-DTPA in 10 mM Tris-HCl pH 7.4, 5) 0.10 mM $Gd^{3+}$ and CD2, 6) 0.077 mM Gd-CA4.CD2, 7) 0.050 mM Gd-CA2.CD2, 8) 0.10 mM Gd-CA9.CD2, 9) 0.020 mM Gd-CA1. CD2, and 10) 0.050 mM Gd-CA1. CD2.

FIG. 1.2B: Proton relaxivity values of Gd-CA 1.CD2 ($\eta$, solid black; $r_2$, cross) and Gd-DPTA ($j_\lambda$, shield; $r_2$, open) at indicated field strength were measured.

FIG. 1.2C: In vitro relaxivity of contrast agents Gd-DPTA (DTPA), Gd-CA 1.CD2 (CA1) and Gd-CA2.CD2 (CA2) in the absence Of$Ca^{2+}$ (black and grey), presence of 1 mM $Ca^{2+}$ (left strip and open) and 10 mM $Ca^{2+}$ (right strip and cross) at 3T. Ti (black, left & right strips) and $T_2$ (grey, open and cross) were determined using a Siemens whole-body MR system.

FIGS. 1.3A-1.3B: Dynamic properties and hydration water number of designed contrast agents.

FIG. 1.3A: S order values of the engineered metal binding protein. The positions of ligand residues are shown in vertical bars. Order factors of CA2-CD2 with discontinuous ligand residues have the same dynamic properties as the scaffold protein. Arrows indicate the position of ligand residues.

FIG. 1.3B: Measurement of coordination water number by monitoring $Tb^{3+}$ life time. Luminescence decay lifetime was obtained by fitting the acquired data in both $H_2O$ and $D_2O$ with a mono-exponential decay function. A standard curve correlating the $\Delta k_{obs}$ with water number was established by using well-characterized chelators, such as EDTA (q=3), DTPA (q=1), NTA (q=5), and Aquo $Tb^{3+}$ (q=9) solution with $R^2=0.997$.[26,27] Water numbers coordinated to $Tb^{3+}$-protein complexes were then obtained by fitting the acquired $\Delta k_{obs}$ value to the standard curve.

FIGS. 1.4A-1.4C: In vivo MR images and biodistribution of designed contrast agents.

FIG. 1.4A: MR images of mouse (26 g) pre (left) and 40 minutes post (right) the injection of 50 µL of 1.2 mM Gd-CA11.CD2 through the tail vein. The MRI was performed using a spin echo sequence with TE/TR/Angle=15 ms/500 ms/90° using a 3T scanner. The arrows indicate the contrast enhancements at different organ sites.

FIG. 1.4B: The MRI signal intensity changes at kidney (•), liver (▲), and muscle (Q) as a function of time. The 0 refers to the pre-injection.

FIG. 1.4C: Tissue distributions 1 hour post intravenous injection of Gd-CA1.CD2 (3.0 µmole/kg, solid black), Gd-DTPA (150 µmole/kg, grey), and GdCb (100 µmole/kg, open) The $Gd^{3+}$ in tissues was measured by ICP-MS and was calculated and expressed as percent of the injected dose.[45] The $Gd^{3+}$ in carcass is the average of randomly picked 10 different sites from rest of whole body after removing indicated organs. Error bars in FIGS. 1.4A, 1.4B, and 1.4C are standard deviations of four measurements or four animals (n=4).

FIG. 1.5: The ESI-TOF MS spectrum of Gd-CA 1.CD2. The CA1.CD2 (10 µM) in 1 mM ammonium acetate (pH 7.0) was mixed with 20 µM of gadolinium chloride ($GdCl_3$). The ESI-TOF MS spectra of the complex were recorded by Q-TOF Micro Mass Spectrometer (Micromass).

FIGS. 1.6A-1.6C: Measurement of metal binding constants. $Gd^{3+}$ binding affinity (FIG. 1.6A) and $Zn^{2+}$ binding affinity (FIG. 1.6B) of CA1.CD2 measured by dye competition assays. CA1. CD2 stock solution was gradually added into the 1:1 dye-metal complex to compete for the dye-bound metal ions. The insets show the titration curve for the dye indicators fluo 5N (FIG. 1.6A) and FluoZin (FIG. 1.6B), respectively. (FIG. 1.6C) $La^{3+}$ binding affinity obtained by Aromatic residue sensitized $Tb^{3+}$ luminescence energy transfer. The $Tb^{3+}$ fluorescence of a protein-$Tb^{3+}$ mixture decreases with the addition of $La^{3+}$. The $La^{3+}$ concentrations are 0, 0.30, 0.76, 5.95, 11.03, and 28.95 µM from top to bottom. The $Tb^{3+}$ fluorescence decrease competition was fitted (line) by a normal competition plus a nonspecific quenching effect (inset).

FIGS. 1.7A-1.7B: MRI imaging of CA1.CD2 at 9.4 T.

FIG. 1.7A: MR images of CD-I mouse (26 g) (four mice were imaged) at 9.4T field using Gd-CA1. CD2 as a $T_2$-weighted contrast agent. The images were recorded pre-(i) and 2 hours post-(ii & iii) injection of 50 µl of 1.2 mM Gd-CA1. CD2 agent through the tail vein. MR images were recorded using a multi-echo Carr-Purcell-Meiboom-Gill (CPMG) sequence. The in-plane resolution is 0.2×0.3×1.0 mm.

FIG. 1.7B: The $T_2$ MRI relative intensity changes at kidney cortex (cross bars), kidney medulla (bars), kidney center (bars), liver (bars), and muscle (bars) as a function of time (indicated). The MRI intensity in muscle at 10 minutes post contrast administration was defined as 1. MRI intensities at other tissue sites were normalized to the muscle intensity.

FIGS. 1.8A-1.8B: Detection of CA1.CD2 in serum and cytotoxicity of CA1.CD2.

FIG. 1.8A: Sandwich ELISA detection of CA1.CD2 in mouse blood using OX45 and PabCD2. PabCD2 was used as the capture antibody and 0X45 was used as the detection antibody in the sandwich-ELISA experiments. Serum samples were obtained from test mice at 0, 0.5, 1.0, 2, and 3 hours post injection (tail vein) of Gd-CA1. CD2 (~1.0 µmole/kg). The amounts of CA1.CD2 are expressed as percentages of the injected dose. Calculations are based on the assumption that the total blood volume is 8% of each individual mouse body weight.

FIG. 1.8B: The cytotoxicity of designed protein Gd-CA1.CD2. The SW480 cells were grown under standard conditions ($1\times10^4$ cells in 100 µl medium). The cells were treated by addition of wild type CD2 (stripe bars), CA1. CD2 (grey bars), Gd-CA 1.CD2 (black bars), and Gd-DTPA (cross bars) with concentrations of 30 µM (left panel) or 50 µM (right panel). The open bars are controls where cells were treated with PBS buffer. The cells were incubated with the treatments for 48 hours. The cells were then subjected for MTT assay. The results were presented as percentages of viable cells using the cells that were treated with buffer alone (filled bars) as a reference (100%). The cell lines SW620 and HEK293 were similarly examined. The error bars in FIGS. 1.8A and 1.8B are standard deviations of four measurements or four animals (n=4).

FIG. 2.1(a): Illustrates the model structure of the designed contrast agent CA1.CD2 with eight Lys residues highlighted. The solvent accessibility calculated by Getarea is also listed. FIG. 2.1 (b): Examples of PEGylation reagents used with different chain lengths and molecular weights and related chemical reactions.

FIG. 2.2: (top) illustrates a FPLC profile for the separation of pegylated protein CA1.CD2 with P12K and reaction mixture by gel filtration column, (bottom) The SDS gel of FPLC fractions (peaks 123) of CA1.CD2 pegylated with P40 stained by idiol (left) and commassie blue (right).

FIG. 2.3: The SDS gel stained by commassie blue (middle) for protein and iodine (top) for PEG moiety with 5:1 PEG:protein using the preactivated PEG reagents. 1. Marker; 2. CA1. CD2; 3. PEG4; 4. PEG12; 5. PEG40; 6. PEG5K; 7. PEG12K; 8. PEG20K. CA1. CD2 was Pegylated mainly with 3, 4, 5 PEG. (bottom) MALD-Mass analyses of mixture after PEGylation with PEG40.

FIG. 2.4: Illustrates the conformational analysis of PEGylaed CA1. CD2. (left) Trp emission fluorescence spectrum of CA1.CD2 is similar to that PEGylated CA1.CD2-PEG12 and CA1.CD2-PEG40 excited at 280 nm. (right) The Terbium-sensitized energy transfer was used to monitor the binding of metal ions in the designed binding pocket. The Tb3+ emission is gradually increased upon addition of terbium excited at 280 nm.

FIG. 2.5: Pegylated CA1.CD2-P40 remains intact after incubate with human serum for 24 hours at 37° C. monitored by SDS Page.

FIG. 2.6: R1 (left) and R2 (right) relaxivity values of CA1.CD2 alone, pegylated with P12, and P40 compared with DTPA at different field strengths (0.47, 3.0, 9.4, and 11.4T).

FIG. 2.7: Illustrates ELISA (left) or western blot (right) analyses of antibody produced in rabbit serum after i.p. injection of 3 ng/kg of protein CA1. CD2 or PEGylated CA1. CD2 (PEGCA1. CD2). In (left), Pre is the serum from pre-bleeding before antigen injection. CA1.CD2 was mixed with adjuvant (CA1.CD2+Ad) or with buffer saline (CA1.CD2+Sal) before injection. PabCD2 is the anti-serum from rabbits produced by a commercial source use CD2 as antigen. The open bars are the first bleed after first injection. The gray bars are the second bleed after second injection. The rabbit blood was taken 3 weeks after each injection. The error bars are standard deviations of four measurements. In (right), Western blots were performed with anti-serum (1st bleed) from rabbits that were injected; CA1. CD2 mixed with buffered saline (left panel, CA1.CD2+Sal), CA1.CD2 mixed with adjuvant (middle panel, CA1.CD2+Ad), and the PEGylated CA1. CD2 (right panel, PEG-CA1. CD2). The Western blots experiments were carried out with 0.5 mg of PEGylated CA1. CD2 (PEG-CA1. CD2) or unmodified CA1.CD2 (CA1.CD2). Arrow indicates the position of the detected protein bands 19 hours post injection.

FIG. 2.8: Table 2.1 is a summary of water number in CA1. CD2 and its variants.

FIG. 3.1: Illustrates the development of MRI contrast agents by modifying natural calcium binding proteins such as calmodulin with four metal binding sites.

FIGS. 3.2A-3.2C: Illustrates the determination OfGd$^{3+}$ stability constant of CaM variants. CaM titration (FIG. 3.2A) and its curve fitting (FIG. 3.2B) with Fura-2 fluorescence spectra. The measurement was performed at 20 mM Gd$^{3+}$ and 20 mM Fura-2 with 10 mM Tris and pH 7.4. The arrows show fluorescence intensity changes at 340 nm and 380 nm excitation wavelengths with the increase of CaM concentration, respectively, lem=510 nm. FIG. 3.2C: The meal selectivity of CBPP (left) and CBPP56 (right). The addition of 1.5 μM protein to free Tb$^{3+}$ (40 μM) solution resulted in an increase of fluorescence intensity at 545 nm by over 20-fold due to the binding of Tb$^{3+}$ to the protein and the resultant FRET. 10 mM Mg$^{2+}$, 2 mM Ca$^{2+}$, 1 μM Ca$^{2+}$, 0.1 mM Zn$^{2+}$, and 10 μM La$^{3+}$ and 10 μM Gd$^{3+}$ were subsequently added to individually prepared solutions containing 40 μM Tb$^{3+}$, 100 mM KcI and 1.5 μM CBPP or CBPP56.

FIG. 3.3: Illustrates the SDS gel of PEGylation of CaM variants with P12 (lanes 1-6), P40 (lanes 7-10), P5K (Lanes 11-14), and P40 (lanes 15-17) at different reaction time with PEG:protein 5:1 ratio stained by Idiol (top A) and commossie blue (bottom B).

FIG. 3.4: Illustrates the separation of PEGylation of CaM variants-P12 with mono-Q column (left) and UV absorption spectrum of purified protein (right).

FIGS. 3.5A-3.5C: Illustrates Tyr emission spectra of CAM variant without and with PEGYlation by P12K excited at 280 nm (FIG. 3.5A) Emission spectra of Tb fluorescence of CAM variant (FIG. 3.5B) and its PEGylated one in the presence of 0 (bottom), 5 uM (middle), and 20 uM of protein (top) excited at 280 nm (FIG. 3.5C).

FIGS. 3.6A-3.6B: Shows the SDS PAGE results of serum stability for new designed protein based MRI Contrast Agents at different time points incubating with serum at 37° C. (FIG. 3.6A). CBP1; (FIG. 3.6B). CBPP.

FIG. 3.7: Illustrates MRI images of Mice at 4.7T with tail vein injection of 6 mM CBP1 at 0, 10, and 30 mins post injection (top). Relative MRI intensity at different organs (bottom).

FIG. 3.8: Illustrates relaxivity of CBP1 at 0.47 T. Both R1 and R2 values are 5-8 fold higher than DTPA.

FIG. 3.9: Illustrates MRI images of Mice at 4.7T with tail vein injection of 6 mM CBP1-P40 at 0, and 13 mins post injection at slice 3 (top) and slice 4 (bottom), (right) These graphs illustrate the relative MRI intensity at different organs.

FIG. 3.10: Illustrates Table 3.1, which shows the dissociation constant of Ca$^{+}$, Tb3+ and Gd$^{+}$ to CBPP were measured by Fluorescence spectroscopy. To determine the Ca$^{+}$ and Gd$^{+}$ dissociation constant, the intrinsic tryptophan fluorescence change were used to monitor the binding process between CBP1/CBPP and metal. The free metal concentration were controlled by the metal-EGTA buffer system and calculated by [Metal]f$_{ree}$=Kd*[EGTA-metal]/[EGTA]f$_{ree}$. The aromatic residue-sensitized Tb$^{+}$ fluorescence at 545 nm were applied to monitor the process of Tb-$^{+}$ binding to CBP1/CBPP and the variants.

FIG. 4.1: The affibody that can specifically bind to Her2 biomarker on the cancer cells was fused to the C-terminal of the protein contrast agent CA1.CD2 with a designed Gd$^{3+}$ binding site (denoted as CA1-Affi). This contrast agent was surface modified with PEG40 to reduce immunogenesity and increase solubility and serum stability (PEG-CA 1-Affi). The affibody was further conjugated with near infra-red dye Cy5.5 via a Cys at the C-terminal to generate a dual labeled contrast agent PEG-CA 1-Affi-Cy5.5.

FIG. 4.2: Contrast agent with PeGylation (PEG-CA1-affi) and without PeGylation (CA1-Aff) is able to bind to the positive cell line AU565 with membrane staining at 4 C (top right) and both membrane and cytosol staining at 37 C (top left). This developed contrast agent does not bind to negative cell line EMT-6 at either 4 or 37 C. (Bottom right) Near IR labeled contrast agent PEG-CA 1-affi-Cy5.5 is able to bind to positive cell lines AU565 and AKOV-3 with NIR fluorescence signal. These data suggest that our contrast agent fused with the affibody can target to HER2 positive tumor cell lines specifically. PEGylation does not change the target capability to the cancer cell. At 37° C., the contrast agent is endocytosized.

FIGS. 4.3A-4.3B: Specific targeting to the positive cancer cell line (AU565) and negative cell line (EMT6) monitored by $^{153}$Gd (FIG. 4.3A) and ELISA (FIG. 4.3B). Similar radioactivity (CPM) of the contrast agents without PEGylation (CA1-Affi) and with PEGylation (PEG-CA1-Affi) at 75, 150, 375 nM were observed for AU565 cell line. Under identical conditions, negative cell line EMT has a small radioactivity after incubating with $^{153}$Gd labeled contrast agent.

FIG. 4.4: Breast cancer biomarker HER2 positive tumor and negative tumor were implanted on the left and right back in nude mice. 5 mM contrast agent CA1.Affi-P40 (100 fold lower than clinic used DTPA) was injected via tail vein. MRI images at 4.7 T using fast spin echo were acquired before injection, and at 5 min, 30 min, 3 hr, 24 hr and 52 hr post injection. Positive tumor shows a strong contrast after 30 mins and peaked at 24 hour with about 35% enhancement. Contrast capability was decreased after 52 hours, suggesting that the contrast agent was secreted out of the animal. This mouse was alive and looks normal after 52 hours MRI scanning.

FIG. 4.5: Nude mice were inoculated with negative cell line MDA-MB-231 and positive cell line SKOV-3 (top). The cell number for each spot was about 5×10$^6$. The specific binding of positive tumor on the right upon injection of the dual labeled contrast PeG-CA 1-Affi-Cy5.5 can be visualized using Kodak NIR in vivo FX-pro animal imaging system 21 hours poster injection, (middle) Traverse MR images of tumor mice at 4.7T with fast spin echo obtained at 3 min., 35 min., and 21 hours following administration of the contrast agent, (bottom right) The intensity enhancement at the positive tumor by our contrast agent analyzed by Image J.

FIG. 4.6: Western Blot with PAbPEGCA1 (top) and NIR imaging (bottom) of different tissues of the tumor nice after MRI imaging.

FIG. 4.7: Immunohistochemistry (IHC) staining using the antibody PAbPGCA1 with tissue slides made from the tissue samples from the imaged mice, including HER2 tumors. Strongest staining was observed with liver and HER2 positive tumor tissue slides. The kidney slides also gave strong immunostaining. Interestingly, the areas near proximal tubes showed the strongest staining in the slides made from the kidney, indicating that the protein contrast agent was ready to be filtered through the kidney.

FIG. 4.8: The binding of CAM-Affi with HER2 positive cells was measured by western blot.

FIG. 4.9: Immune staining of CaM-AfTi treated breast cancer cells for skov-3 (Left, Her 2 positive) and MDA-MB-231 (right, Her2 negative).

FIG. 4.10: Immunostaining CA-Bom, CA-52I-Bom, CA at different time points for PC-3 and DU145 (GRPR high expression), and H441 (GRPR low expression).

FIG. 4.11: Near IR imaging of nude mice xenografted with DU-145 tumor (high expression of GRPR, left) and H441 tumor (low expression of GRPR, control, right) post injection of CA1.CD2-52Ibom-cy5.5-P40 26 hours via tail vein.

FIG. 4.12: NIR imaging (top) and NIR intensity (bottom) of CA1.CD2-52I-Bom-Cy5.5-P40 at different organs of the mice.

DETAILED DESCRIPTION

Before the present disclosure is described in greater detail, it is to be understood that this disclosure is not limited to particular embodiments described, and the embodiment of the invention as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of imaging, synthetic organic chemistry, biochemistry, biology, molecular biology, recombinant DNA techniques, pharmacology, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

As used herein, a "contrast agent" is intended to include any agent that is physiologically tolerable and capable of providing enhanced contrast for magnetic resonance imaging. A suitable contrast agent is preferably biocompatible, e.g., non-toxic, chemically stable, not absorbed by the body or reactive with a tissue, and eliminated from the body within a short time.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

"Variant" refers to a polypeptide or polynucleotide or polymer that differs from a reference polypeptide or polynucleotide or polymer, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

A variant of a polypeptide may contain different modifications such as with PEGylation groups or the same type of groups with different sizes or lengths of the modifications.

"Variant" generated such as by modifying metal binding sites may have different metal binding properties and relaxivities and vivo properties.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST and XBLAST). The default parameters are used to determine the identity of the polypeptides of the present disclosure.

By way of example, a polypeptide sequence may be identical to the reference sequence, that is 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in *Xenopus* oocytes by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotide encompasses the terms "nucleic acid," "nucleic acid sequence," or "oligonucleotide" as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

The term "antibody" is used to refer both to a homogenous molecular entity, or a mixture such as a serum product made up of a plurality of different molecular entities. Monoclonal or polyclonal antibodies, which specifically react with the virosomes of the present disclosure, may be made by methods known in the art. (e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987)). Also, recombinant immunoglobulin may be produced by methods known in the art, including but not limited to, the methods described in U.S. Pat. No. 4,816,567, which is hereby incorporated by reference herein.

Affibody® ligands (U.S. Pat. No. 5,831,012, which is incorporated herein by reference) are highly specific affinity proteins that may be designed and used like aptamers. Affibodies may be produced or purchased from commercial sources (Affibody AB, Bromma, Sweden). Aptamers and affibodies may be used in combination with antibodies to increase the functional avidity of translucent or non-translucent solid matrices for probe molecule binding. Increased binding in turn results in an increased signal strength, greater signal-to-noise ratio, more reproducible target molecule detection and greater sensitivity of detection.

Aptamers must also be differentiated from the naturally occurring nucleic acid sequences that bind to certain proteins. These latter sequences generally are naturally occurring sequences embedded within the genome of the organism that bind to a specialized sub-group of proteins or polypeptides, or their derivatives, that are involved in the transcription, translation, and transportation of naturally occurring nucleic acids, i.e., protein-binding nucleic acids. Aptamers on the other hand are short, isolated, non-naturally occurring nucleic acid molecules. While aptamers can be identified that bind nucleic acid-binding proteins, in most cases such aptamers have little or no sequence identity to the sequences recognized by the nucleic acid-binding proteins in nature. More importantly, aptamers can be selected to bind virtually any protein (not just nucleic acid-binding proteins) as well as almost any target of interest including small molecules, carbohydrates, peptides, etc. For most targets, even proteins, a naturally occurring nucleic acid sequence to which it binds does not exist. For those targets that do have such a sequence, i.e., nucleic acid-binding proteins, such sequences will differ from aptamers as a result of the relatively low binding affinity used in nature as compared to tightly binding aptamers. Aptamers are capable of specifically binding to selected targets and modulating the target's activity or binding interactions, e.g., through binding, aptamers may block their target's ability to function. The functional property of specific binding to a target is an inherent property of an aptamer.

A typical aptamer is 6-35 kDa in size (20-100 nucleotides), binds its target with micromolar to sub-nanomolar affinity, and may discriminate against closely related targets (e.g., aptamers may selectively bind related proteins from the same gene family). Aptamers are capable of using intermolecular interactions such as hydrogen bonding, electrostatic complementarities, hydrophobic contacts, and steric exclusion to bind with a specific target. In the present disclosure, aptamers also employ boronic acid-Lewis base/nucleophile (such as hydroxyl groups, diols, and amino groups) interactions for binding. Aptamers have a number of desirable characteristics for use as therapeutics and diagnostics including high specificity and affinity, low immunogenicity, biological efficacy, and excellent pharmacokinetic properties.

As used herein, the term "PEGylation" means and refers to modifying a polymer (e.g., a protein) by covalently attaching polyethylene glycol (PEG) to the polymer, with "PEGylated" referring to a polymer having a PEG attached. For further general information on PEGylation methods see, for example, the Nektar Advanced PEGylation Catalogs 2004 and 2005-2006, as well as the references cited therein. PEGYlation can be achieved by non-specific interaction with functional group of polypeptide chain such as via amino group or specific interaction at certain location of the macromolecules such as amino terminal or at the Cys residues.

The terms "biomarker" or "biomarker probe" are used to refer to a substance used as an indicator of a biologic state. It is a characteristic that is objectively measured and evaluated as an indicator of normal biologic processes, pathogenic processes, and/or pharmacologic responses to a therapeutic intervention.

The term "disease marker" is used to refer to substances, such as proteins, bio-chemicals, nucleic acids, carbohydrates, or enzymes, produced by disease cells or by the body in response to disease cells during disease development and progression. These substances are indicative of a particular disease process.

By "administration" is meant introducing a compound into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of a contrast agent including a compound to provide a pharmacologic effect, even in the absence of a disease or condition. For example, "treatment" encompasses delivery of a disease or pathogen compound via the contrast agent that provides for enhanced or desirable effects in the subject (e.g., reduction of pathogen load, reduction of disease symptoms, etc.).

As used herein, the terms "prophylactically treat" or "prophylactically treating" refers to completely or partially preventing a disease or symptom thereof and/or may be therapeutic in terms of a partial or complete cure for a disease and/or adverse effect attributable to the disease.

The term "unit dosage form," as used herein, refers to physically discrete units suitable as unitary dosages for human and/or animal subjects, each unit containing a predetermined quantity of a contrast agent calculated in an amount sufficient to produce the desired effect in association with a pharmaceutically acceptable diluent, carrier or vehicle. The specifications for unit dosage forms depend on the particular compound employed, the route and frequency of administration, the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" is meant to encompass a contrast agent suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of a contrast agent being administered that is sufficient to effect the intended application. In an embodiment, the effective amount of the contrast agent includes enough so that the disease, for example, in the host can be imaged, studied, diagnosed, or the like. For example, an effective amount of a contrast agent including a compound will relieve to some extent one or more of the symptoms of the disease being treated, and/or that amount that will prevent, to some extent, one or more of the symptoms of the disease that the host being treated has or is at risk of developing. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

"Cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

It should be noted that precancerous cells, cancer cells, cancer, and tumors may be used interchangeably in the disclosure.

The terms "including", "such as", "for example", and the like are intended to refer to exemplary embodiments and not to limit the scope of the present disclosure.

Discussion

In accordance with the purpose(s) of the present disclosure, as embodied and broadly described herein, embodiments of the present disclosure, in one aspect, relate to contrast agents, compositions including contrast agents, methods of making contrast agents, methods of imaging, methods of diagnosing, methods of studying, and the like.

More particularly, embodiments of the contrast agents include magnetic resonance imaging contrast agents that accumulate in tissue and can be used to determine the presence and/or location of a target. In addition, contrast agents of the present disclosure can include targeting agents to target cells or tissue (e.g., cancer). Embodiments of the present disclosure can be tuned to have properties for diagnostic imaging.

In general, embodiments of the present disclosure include contrasts agents that include a scaffold polymer (e.g., protein or peptide) that includes (e.g., integrated into the scaffold protein) at least one tailored metal ion binding site (e.g., 1, 2, 3, 4, 5, or more biding sites) (also referred to as "metal ion binding site") capable of chelating paramagnetic and heavy metal ions. In an embodiment, the contrast agent can include a targeting agent. In an embodiment, the contrast agent can include a Near-IR moiety (e.g., functional group). In an embodiment, the modification of the metal binding site, either by residue mutation or insertion, is intended to alter the metal selectivity of the binding site. In an embodiment, the contrast agent includes a metal ion interacting (e.g., bonding with or chelating with) with the metal ion binding site. In an embodiment, a contrast agent can include two metal ions interacting (e.g., bonding with or chelating with) with two metal ion binding sites. In an embodiment, the metal ion binding site may be developed by a design approach or by a grafting approach. After the site has been developed, the site or sites are operatively integrated into the select areas of the scaffold polymer.

In an embodiment, the contrast agent is stable in a physiological environment. The phrase "physiological environment" can be described as cell, cellular conditions, tissues, organs, and vertebrate/invertebrates, animal/human or buffer conditions (e.g., pH of about 6-8 and a temperature of about 5-45° C.) mimic closely to the cellular, or in vivo conditions. The term "stable" in reference to "physiological environment" means that the contrast agent is able to provide contrast capability and remain intact. In an embodiment, the phrase "stable in a physiological environment" refers to the contrast agent including at least one metal ion and the binding of the metal ion causes no changes or substantially no changes (e.g., less than 50%) to the protein (scaffold protein) conformation or to the binding affinity of the tailored metal ion binding site under clinical conditions (physiological environment) that would cause premature release of the metal ion, and that the contrast agent functions as a contrast agent as described herein.

In an embodiment, the scaffold polymer of the contrast agent includes polyethylene glycerol compounds (PEG) attached to the polymer. The PEGs can be attached (e.g., bonded) to the polymer via an amino acid residue such as lysine (Lys), glutamic acid (Glu), aspartic acid (Asp), cysteine (Cys), and/or carboxyl/amino terminals. The position of the amino acids on the polymer can be selected to position the PEGs so that the PEGs do not substantially interfere (e.g., decrease metal binding affinity more than 20%) with or interfere with the metal ion binding sites ability to interact with the metal ion of interest or the conformation of the polymer. In an embodiment, the PEGs are attached to one or more Lys residues since the position of the Lys residues on the polymer is such that the PEGs do not substantially interfere with or interfere with the metal ion binding site ability to interact with the metal ion of interest or the conformation of the polymer. Unless otherwise indicated or understood from the context of the sentence or the embodiments being described, reference to "contrast agent" refers to a contrast agent that includes PEGs. As noted herein, embodiments of the present disclosure include contrast agents that include PEGs and contrast agents that do not include PEGs. Additional details regarding PEGs are described herein.

Embodiments of the present disclosure provide for PEGylated contrast agents, where the PEGylation increases the blood circulation time of the contrast agent in CD-1 mice. In addition, PEGylation of the contrast agent increased the solubility of the contrast agent by more than two-fold, three-fold, four-fold, five-fold, six-fold, seven-fold, eight-fold, nine-fold, ten-fold, or more relative to the un-PEGylated contrast agent. It should also be noted that PEGylation of the contrast agent further increased the in vitro of one or both R1 and R2 relaxivities of the contrast agents by about 10%, 25%, 50%, 75%, 100%, or 2-3 fold or more, relative to the un-PEGylated contrast agent. Although not intending to be bound by theory, the increase in molecular size due to the PEGylation and the addition of a hydration layer due to water retention by Poly-PEG chain on protein surface may be the reasons for the increases in the relaxivities.

Embodiments of this disclosure include contrast agents capable of enhancing image contrast by affecting water molecule proton relaxation rates. Such contrast agents are effective for magnetic resonance imaging, in part, because the water proton relaxation rate in the target tissue is affected differently from the relaxation rate of the water protons in the surrounding tissue. In an embodiment of the present disclosure, the contrast agents are paramagnetic species, which form complexes with metal ions, so to alter the relaxation rates of adjacent nuclei.

In an embodiment, the scaffold polymer (referred to as a "protein" or "peptide" hereinafter) for MRI applications are a protein that will host the tailored metal ion binding sites and has the following characteristics:

(a) stability in a physiological environment,
(b) a topology suitable for the integration of metal ion sites,
(c) a rotational correlation time optimized for the magnetic field (e.g., around 100 milliseconds in a magnetic field of 1.3 to 3T), e.g., higher magnetic field application can demand a host protein with a larger molecular weight, and
(d) a water exchange rate such that the relaxivity of the protein is not limited by the water exchange rate.

In another embodiment, the contrast agent for use in MRI applications can include a scaffold protein (referred to as a "protein", "polymer", or "peptide") that includes a natural metal binding protein or a fragment/domain of natural metal binding proteins either with metal binding sites modified by at least one amino acid or protein modification.

Properties of the scaffold protein also may include water solubility, low interaction with the other cellular metal ions and low toxicity. While all these properties are not required, the optimal properties of the scaffold protein can depend on the specific parameters of the imaging application.

Another property of the scaffold protein is its ability to accept the introduction of metal ion binding sites therein. In an embodiment, the scaffold protein has a three-dimensional structure or an amino sequence with some homology to the proteins whose structures have been solved, at least in part. Specifically, the scaffold protein is screened to determine whether it can tolerate the integration of various binding sites without excessive denaturation. For example, the integration of metal ion binding sites into the scaffold protein should not denature or unfold the protein. Thus, the metal ion binding site should not be placed by mutating a hydrophobic core or in a position that results in substantial structural perturbation. This can be examined by sequence alignment of proteins in the same family. In an embodiment, the amino acids that have an essential role in folding of the structure or the function will be conserved among different species of this same type of the protein.

In an embodiment, metal ion binding sites are placed into a scaffold protein such that the metal can be tumbled together with the protein. It is better to find a location that is not so flexible or the same flexibility as the protein body so as to match the correction time. In an embodiment, it is preferred to design or create the binding pocket in the protein. Although insertion could work, it is preferable to do so in a relatively not so flexible region. Usually the protein can be checked by looking at the B factor (temperature factor for X-ray) or S2 factor (dynamic flexibility factor for NMR) of the pdb (protein data bank) file of the structure.

In an embodiment, more than one metal binding site may be integrated into a scaffold protein. The inclusion of more than one binding site improves the sensitivity of the contrast agent. In embodiments where more than one binding site is integrated into the protein, the site could have different affinities, but should still have strong enough affinity for the selected metal so to avoid competition with physiological metal ions. Both metal ions should be embedded into the host protein with preferred rotational correlation times and water exchange rates to provide MRI contrast with an increased sensitivity.

In an embodiment, the contrast agent can have a high affinity to and can preferentially select a particular metal ion (e.g., $Gd^{3+}$, $Mn^{2+}$, or $Fe^{3+}$). In one example, exemplary contrast agents showed a dissociation constant $K_d$ less than $10^{-12}$ [M] for $Gd^{3+}$ in an environment having physiological metal ions and prevented those metal ions from precipitation under physiological conditions. Thus, the present disclosure may be used to create contrast agents having optimal selectivity for a specific metal ion.

Embodiments of the present disclosure can provide a new mechanism to increase the relaxivity of contrast agents. This is accomplished by designing the metal ion binding sites, e.g., $Gd^{3+}$, in proteins, which can eliminate the mobility and flexibility of the chelating moiety associated with currently available contrast agents. High proton relaxivity by contrast agents can further enhance images.

An advantage of the present disclosure is that it provides contrast agents that can preferentially chelate a specific metal ion. For example, a preferred contrast agent having $Gd^{3+}$ binding site(s) will preferentially chelate $Gd^{3+}$ over other metal ions, such as $Mg^{2+}$ or $Ca^{2+}$. The ability to preferentially chelate a specific metal ion can improve the specificity of a contrast agent and reduces the cytotoxicity of the contrast agent.

As mentioned above, some embodiments of the contrast agents include PEGs attached to the protein. Inclusion of the PEGs in the contrast agent increases blood circulation time, increases the solubility of the contrast agent in a physiological system, and/or increases R1 and R2 relaxivities, relative to un-PEGylated contrast agents. In an embodiment, the PEGs are bonded to the protein via an amino acid residue such as lysine (Lys), glutamic acid (Glu), aspartic acid (Asp), cysteine (Cys), carboxyl/amino terminals, or combinations thereof. As mentioned above, the position of the amino acids on the polymer should position the PEGs so that the PEGs do not substantially interfere with or interfere with the metal ion binding site ability to interact with the metal ion of interest or the conformation of the polymer.

In another embodiment, a fusion protein/peptide/polymer or a non-degradable particle moiety can be added to the protein contrast agent with a linker to tune the correlation time for optimal contrast sensitivity, targeting (e.g., subcellular, cellular, tissue and organ selectivity), biodistribution (e.g., affiibody against to Her-2 was fused to CA1 as a targeted contrast agent to breast cancer), and/or bioelimination (e.g., using proteins with molecular weight less than 60 KDa). One of ordinary skill in the art may determine such linkers without undue experimentation.

An additional advantage of the contrast agent of the present disclosure is that targets of interest (e.g., specific tissues, specific organs, and biomarkers for molecular imaging of tissues and tissue growths such as cancerous cells or tissue, precancerous cells or tissue, cancer, or tumors) can be imaged. The active targeting of contrast agents to specific organs or tissues can be achieved by attaching (directly or indirectly via linking) a compound (e.g., peptide, antibody, antigen, and the like) having an affinity for the target of interest. Thus, the contrast agent can be administered to the host, and the contrast agent will interact with the target of interest. Subsequently, the host can be imaged to determine the presence or absence, as well as the location of the target of interest. Additional details are provided herein.

Scaffold Proteins

Scaffold proteins suitable with the present disclosure include proteins or organic polymers containing amino acids. In an embodiment, the scaffold proteins can be modified. The scaffold proteins are inclusive of both natural amino acids and unnatural amino acids (e.g., beta-alanine, phenylglycine, and homoarginine, Gamma-carboxyglutamate (Gla)). In an embodiment, the amino acids are alpha-amino acids, which can be either of the L-optical isomer or the D-optical isomer. In an embodiment, the amino acids are D-optical isomers, as such isomers are less subject to proteolytic degradation. Such amino acids can be commonly encountered amino acids that are not gene-encoded, although preferred amino acids are those that are encodable. In an embodiment, a Near-IR functional group (e.g., Cy5.5, Cy7, Alexflour, and indocyanine green) for Near-IR detection is covalently bound to the scaffold protein, a PEG, and/or a targeting agent.

As mentioned previously, in some embodiments the scaffold proteins should include one or more amino acid residues (e.g., Lys, Glu, Asp, Cys, or combinations thereof) able to bond with the PEGs or otherwise modified. In this regard, the position of the amino acids on the protein should position the PEGs so that the PEGs do not substantially interfere with or interfere with the metal ion binding site ability to interact with the metal ion of interest or the conformation of the polymer.

Various scaffold proteins may be used according to the disclosure, but in general they will be proteins, and organic polymers. More specifically, suitable scaffold proteins can be selected properties suitable for diagnostic applications. The scaffold protein for use with this disclosure may be of unitary construction (a particulate, a polychelant or a dendrimeric polymer). Scaffold proteins suitable with this disclosure may be selected without undue experimentation.

Embodiments of the present disclosure can include proteins such as CD2 proteins (a cell adhesion protein) that exhibit high stability against proteolysis, thermal conditions (Tm 67° C.), pH (2-10), and salt (0-4 M NaCl) denaturation. CD2 proteins can be suitable with this disclosure because such proteins are stable in physiological environments, have a topology suitable for the integration of at least one or multiple metal ion chelating sites, and typically have a relaxivity greater than 10 $mM^{-1} s^{-1}$ (some of them up to about 50 $mM^{-1} s^{-1}$). In addition, CD2 proteins can tolerate multiple surface mutations without unfolding the protein. In another embodiment, the CD2 proteins can be used as a host protein to design calcium binding sites. Examples using CD2 are described herein.

Fluorescent proteins are another class of preferred scaffold protein for this disclosure, as these proteins are stable in a physiological environment against proteolytic degradation and pH denaturation (pH 5-10). Such fluorescent proteins include an array of fluorescent proteins including those related to *Aequorea*. Suitable fluorescent proteins should have a useful excitation and emission spectra and may have been engineered from naturally occurring *Aequorea victoria* green fluorescent proteins (GFPs). Such modified GFPs may have modified nucleic acid and protein sequences and may include elements from other proteins. The cDNA of GFPs may be concatenated with those encoding many other proteins—the resulting chimerics are often fluorescent and retain the biochemical features of the partner proteins. Such proteins also are included in the disclosure.

One advantage of using fluorescent proteins is that contrast agents constructed from such proteins can be multifunctional probes. In this embodiment, the contrast agent constructed from fluorescent proteins can be screened using both fluorescence and MR imaging. This can be advantageous as such properties equip the contrast agent with both the fluorescence needed for fluorescence detection methods and sensitivity needed for the deep tissue detection from MRI. Such contrast agents are multifunctional contrast agents.

Other proteins may be used as scaffold proteins for this disclosure. In an embodiment, scaffold proteins are able to tolerate the addition of the metal ion binding site without substantial disruption to its structure. One of ordinary skill in the art can select a scaffold protein based on preferences without undue experimentation.

Embodiments of this disclosure include natural calcium binding proteins with metal binding site such as calcium binding sites as scaffold protein proteins. These natural metal binding proteins such as calmodulin, calbindin D9K, troponin C, and parvalbumin, can be engineered to bind paramagnetic metal ions with very strong metal binding affinity thus are capable of enhancing image contrast by affecting water molecule proton relaxation rates. In addition, their selectivity over calcium and other physiologic metal ions such as zinc and magnesium is more than $10^5$ fold higher, which is similar to that of clinically approved contrast agents such as DTPA or DTPA-BMA. More than one water molecule can be in the coordination shells and protein surface, and this likely contributes to their extremely high relaxivity. Furthermore, functional sites of these engineered proteins, such as binding to the target molecules by calmodulin, were altered and PEGylation of these engineered proteins increases solubility and reduced immunogenicity and increase relaxivity (See, Example 3).

Embodiments of scaffold protein sequences (SEQ ID Nos: 1-53) that can be included in the contrast agent are provided that include the unmodified scaffold proteins and modified scaffold proteins (insertions and/or deletions) for a variety of illustrative scaffold proteins that include metal ion binding sites. The scaffold protein sequences include one or more possible locations for attachment of PEGs, mutation sites, C-terminal sites for pegylation or conjugation of moieties (e.g., fluorescent dyes), and the like.

PEGs

As mentioned above, embodiments of the present disclosure include contrast agents where PEGs are attached to the protein via one or more amino acid residues such as Lys, Glu, Asp, Cys, carboxyl/amino terminals, or combinations thereof. In an embodiment, the PEGs are attached to amino acid residues so that the PEGs do not substantially interfere with or interfere with the metal ion binding site ability to interact with the metal ion of interest or the conformation of the polymer. The PEGs can be attached to the amino acid residues through PEGylation processes known in the art. The PEGylation may, for example, be performed at a pH of about 7.5 to 9 or about 8 to 8.5.

The PEGs can be linear PEGs, multi-arm PEGs, branched PEGs, and combinations thereof. The molecular weight of the PEGs can be about 1 kDa to 100 kDa, about 1 kDa to 50 kDa, about 1 kDa to 40 kDa, about 1 kDa to 30 kDa, about 1 kDa to 20 kDa, about 1 kDa to 12 kDa, about 1 kDa to 10 kDa, or about 1 kDa to 8 kDa. It should be noted that the molecular weight can be any integer within any of the values mentioned above. When used in reference to PEG moieties, the word "about" indicates an approximate average molecular weight and reflects the fact that there will normally be a certain molecular weight distribution in a given polymer preparation. In an embodiment, 1 to 10 PEGs can be attached to the scaffold protein. In an embodiment, 2 to 6 PEGs can be attached to the scaffold protein. In an embodiment, 2 to 4 PEGs can be attached to the scaffold protein.

The PEGs can have additional functional groups to allow us to further modify the contrast agent by adding other moieties such as signal peptides (such as GRP signal peptide for targeting to prostate cancer).

Targeting Agent

In an embodiment, the contrast agent can have a specific affinity for a target by attaching (directly or indirectly, via the scaffold protein or the PEGs) a targeting agent to the contrast agent. In this regard, the term "affinity" means that the contrast agent is preferentially attracted to the target(s) as opposed to all other targets in the human subject. The contrast agent can be designed to have the affinity using one or more polypeptides (e.g., proteins) or chemical moieties on a target. If the targeting agent is attached to the scaffold protein (attached directly or indirectly), like the PEG (attached directly or indirectly), the targeting agent does not substantially interfere with or interfere with the metal ion binding site ability to interact with the metal ion of interest or the conformation of the polymer.

In an embodiment, a targeting agent can be attached (e.g., directly or indirectly) to the scaffold polymer or the PEG, where the targeting agent has an affinity for a target (e.g., a cell, a tissue, a protein, an antibody, an antigen, and the like). The targeting agent can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, or combinations thereof, where the targeting agent binds or otherwise interacts with the target. In an embodiment, the targeting agent specifically interacts with a specific type of target or specific target and substantially (e.g., 90%, 95%, 99% or more specificity to the target or type of target) or completely excludes other targets. In an embodiment, the targeting agent has an affinity for one or more targets. In general, the target can include, but is not limited to, a cell type, a cell surface, extracellular space, intracellular space, a tissue type, a tissue surface, vascular, a polypeptide, a nucleic acid, a polysaccharide, a sugar, a fatty acid, a steroid, a purine, a pyrimidine, a hapten, a ligand, and the like, related to a condition, disease, or related biological event or other chemical, biochemical, and/or biological event of the sample or host. In an embodiment, the targeting agent can be selected based on the target selected and the environment the target is in and/or conditions that the target is subject to. In an embodiment, the targeting agent can include: a biomarker probe, a precancerous targeting agent, a cancer targeting agent, a tumor targeting agent, and a probe or agent that targets at least two of a biomarker, a precancerous cell, a cancer cell, and a tumor.

The targeting agent can be linked, directly or indirectly, using a stable physical, biological, biochemical, and/or chemical association. In an embodiment, the targeting agent can be independently linked to the scaffold polymer or the PEG using, but not limited to, a covalent link, a non-covalent link, an ionic link, a chelated link, as well as being linked through interactions such as, but not limited to, hydrophobic interactions, hydrophilic interactions, charge-charge interactions, π-stacking interactions, combinations thereof, and like interactions.

In an embodiment, the targeting agent can include, but is not limited to, (gastrin release peptide (GRP) that can bind to specific types of cancer receptors, i.e. GRP receptors, and, RGD peptides (Arg-Gly-Asp) (corresponding to integrin $\alpha_v\beta_3$ target). In an embodiment, molecules that can be targets include, but are not limited to, vascular receptors (e.g., Vascular endothelial growth factor receptor (VEGF-R)), extracellular matrix proteins (e.g., proteases, MMP, thrombin), cell membrane receptors (e.g., epidermal growth factor receptor (EGFR) (e.g., HER2)), intracellular proteins, enzymes (e.g., caspases and PSA), serum proteins (e.g., albumin), and the like.

Metal Ion Binding Sites

The affinity of the metal ion binding site may vary the contrast agent affinity for metal ions. Specifically, as affinity and sensitivity of the metal ion binding sites may be modified, the relaxivity and metal affinity of the contrast agent may be modified. Preferably, the metal ion binding site has optimal imaging properties including metal binding affinity, selectivity, relaxivity, NMRD profile, and water exchange rates.

Embodiments of the metal ion binding site of the present disclosure may be constructed using three methods:

(1) A computational design approach in which the metal ion binding site with a selectivity and affinity for a metal ion is engineered and rationally designed de novo based on optimal binding characteristics of a metal ion with other moieties; and (2) A grafting method in which the metal ion binding site with a selectivity and affinity for a metal ion is engineered and constructed selectively by varying the primary, secondary, and tertiary of an identified binding site.

(3) Direct modification of natural metal binding proteins in which the metal binding affinity to the desired metal ions are significantly increased while the affinity to the physiological metal ions are decreased.

An engineered metal binding site can be created by a combination of more than one above mentioned methods.

The Computational Design Approach

The computational design approach focuses on designing a metal ion binding site de novo. This design approach focuses on using an algorithm to construct and engineer an optimal binding site. Preferably, the computation design approach is used to create optimal binding sites by, e.g., varying the coordination geometry of the site, the water number in the coordination shells, the ligand types, and the charges.

The computational design approach comprises the following steps:

(1) Accessing one or more databases having structural, coordination, and/or 3-dimensional structure or model on metal ion binding sites; or creating model structures based on the sequence homology;

(2) Generating one or more preliminary metal ion binding sites from portions of the structural data;

(3) Selecting rationally one or more suitable metal ion binding sites from the generated preliminary binding sites based on, e.g., coordination geometry; and (4) Creating a metal ion binding site by tailoring and tuning the selected metal ion binding site.

The metal ion binding site may be incorporated into a scaffold protein, e.g., a fluorescent or CD2 protein. Further, such a method may be used to alter metal ion binding properties of proteins and generate new materials with various ion binding affinities.

More particularly, the method involves searching and accessing public and or private databases for preferred components of a metal ion binding site. Such databases that may be searched for the criteria or components may include public domain banks (e.g., NBCI or PubMed) or knowledge banks such as protein modeling structure data banks (e.g., Cambridge or RCSB Protein Data Bank Data Bank and BioMagResBank database) or data bank. Further, the database could include structural data from metal ion binding proteins whose structures have been characterized previously. One of ordinary skill in the art can identify databases and sources of material for databases suitable with this disclosure. Use of a computer obviously would greatly speed up the searching and is preferred.

These databases may be used to provide structural analysis of one to several thousand different small molecules or metal ions that bind to a protein. Such analysis may include local coordination properties, types of residues or atoms commonly used to bind a desired metal ion, chemical features (e.g., pKa or changes), the number of charged residues on a site, and the range or deviation of the known binding sites. Further, such analysis may include the environment, such as types of atoms, residues, hydrophobicity, solvent accessibility, shapes of the metal binding sites, electrostatic potentials, and the dynamic properties (e.g., B-factors or the order factors of the proteins) of the binding sites. Such analysis also may include whether a binding site for a particular metal ion is a continuous or discontinuous binding site.

Once preliminary metal ion binding sites are found, using the structural data and analysis, one or more suitable metal ion binding sites may be generated based on rational factors. Specifically, different search algorithms may be used to generate potential metal ion binding sites based on other key features in addition to, for example, the geometric descriptors. These key features include the properties of the original residues in the scaffold protein, ligand positions that are essential to protein folding, the number of the charged residues and their arrangement and number of water molecules in the coordination shell. The hydrogen bond network and the electrostatic interactions with the designed ligand residues also can be evaluated. Furthermore, the protein environments of metal ion binding sites can be analyzed according to solvent accessibility, charge distribution, backbone flexibility, and properties of scaffold proteins. Thus, one of ordinary skill in the art may rationally select a binding site based on desired parameters.

Once the metal ion binding sites are generated, a site may be tailored using two complementary approaches of computational design and grafting (see below). First, as discussed above, the metal ion binding site may be tailored using a grafting method in which the primary, secondary, tertiary, and/or quaternary structures are tuned. Second, the metal ion binding site may be tailored using a computational design approach. It is understood that one or both of these approaches may be used to tailor the binding site.

The computational design approach includes modifying the metal ion binding site by modifying residues in the scaffold of the metal ion binding site. In one embodiment, a geometric description of the ligands around a metal ion, a three-dimensional structure of the backbone of proteins, and a library of side-chain rotamers of amino acids (or atoms from the main chain) can identify a set of potential metal-binding sites using a computer. Using the geometric and graph description of a particular metal ion site, key ligand residues are carefully placed in the amino acid sequence to form the metal (metal ion) binding pocket. This binding pocket can be created automatically by the computer algorithm according to the coordination description and the user's preferred affinity.

The created potential metal ion binding sites can be optimized and tuned to specification. A backbone structure of the metal ion binding site with different degrees of flexibility may be used according to the need or the flexibility of the metal ion binding site. The designed metal ion binding sites are further filtered and scored based on the local factors, which may include the shape of the metal ion binding sites, locations, charge numbers, dynamic properties, the number of mutation needed, solvent accessibility, and side chain clashes. To achieve the maximums relaxivity, one to two oxygen atoms from the solvent water molecules in the coordination shell may provide additional coordination without reducing the required binding affinity and selectivity.

Stronger metal ion binding affinities of the designed sites may be developed based on several modeled factors that contribute to metal ion affinity. For example, the number of ligand residues is a factor to directly chelate a specific metal ion. In some cases, in order to have a strong metal ion affinity with a $K_d$ necessary to measure a metal ion concentration, it is necessary to include residues from the protein frame for optimal metal ion binding. In other cases, the number of charged residues is able to change metal ion affinity. In still other cases, the ligand type is a factor as the binding preferences of a chelate may depend on the particular ligand type. Other factors, such as negatively charged environments, may contribute to the binding affinity of a metal ion binding protein and can be taken into account by those of ordinary skill in the art without undue experimentation. These charged residues could increase the water-exchange rate to avoid its limitation for the required relaxivity.

An illustrative version of this computational approach is the computerized (or otherwise automated) querying of one or more databases that comprise structural data on metal ion binding sites using selected criteria relevant to the metal ion binding site, generating at least one preliminary metal ion binding site from the database information based on compatibility with the selected criteria, and selecting one or more suitable metal ion binding sites from the preliminary metal ion binding sites based on optimal compatibility with the selected criteria. Once a suitable metal ion binding site is selected, the nucleic acid sequence of the selected metal ion binding site is obtained, tailored, and operatively linked with a scaffold protein sequence, whereby the nucleic acid sequence of the selected metal ion binding site is tailored so to achieve the metal ion binding site having a desired specificity for the metal ion. Further, a nucleic acid sequence encoding the preliminary binding sites can be generated from the structural or model data. The computational approach also can be used to produce the metal ion binding site.

The computational approach can be performed on or by a system comprising at least one database that comprises the structural data on metal ion binding sites, an algorithm for generating the preliminary metal ion binding sites from portions of the structural or model data using selected criteria relevant to the metal ion binding site and rating the preliminary metal ion binding sites based on specificity for a selected metal ion, and a computer for executing the algorithm so as to query the databases to generate the preliminary metal ion binding sites. The algorithm generally is a relatively simple searching algorithm that will query the databases based on inputted criteria.

The Grafting Method

The grafting method focuses on engineering and constructing a metal ion binding site by modifying the primary, secondary, tertiary, and/or quaternary structure of an identified binding site. By selectively manipulating the structure of the binding site, it is possible to obtain a metal ion binding site that can be engineered into a scaffold protein, e.g., CD2 or fluorescent protein, without significantly denaturing the protein. Using the grafting method, it is possible to achieve a binding site that has a stronger preference for one metal ion over another metal ion. Such modifications may allow for improved contrast abilities.

Initially, an identified binding site for use with the grafting method may be any continuous sequence site that has some affinity for a metal ion. Such binding sites may derive from either known binding peptides such as an individual EF-hand site or from short fragments that have demonstrated the ability to bind specific metal ions such as alpha-lactalbumin. Such peptides may be highly conserved in nature and prevalent throughout nature or may be unnatural but known to have an affinity for a particular metal ion. One of ordinary skill in the art is able to identify binding sites with affinity for a metal ion without undue experimentation.

Once the binding site has been identified, the primary structure of the metal ion binding site may be altered and tuned to achieve a metal ion binding site with improved binding characteristics. For example, more charged ligand residues such aspartate and glutamate may be engineered by inserting codon(s) into the metal ion binding site so as to tune the responsiveness of the site or the scaffold protein. The inclusion of additional charged ligands can allow the contrast agent to achieve an affinity for selected paramagnetic metal ions and to have a desired selectivity. Further, one or two water molecules can also be introduced into the coordination shell by removing or modifying ligand residues and their environments. Further other mutations to the primary structure include removing or adding amino acids to change properties such as flexibility or rigidity of the site. Adding or removing amino acids from the binding site alters the primary structure of the binding site.

The secondary structure of the metal ion binding site, that is the spatial arrangement of amino acid residues that are near one another in linear sequence, may be modified to tune the sensitivity and responsiveness of the metal ion binding site. The residues on the site itself, the flanking or the neighboring structures such as helices, beta strands, or turns may be modified by changing properties such as hydrophobicity, salt bridges, secondary structure propensity (e.g., helicity and β-sheets), and charge interactions with different amino acids, which all may inherently change the secondary structure.

The tertiary structure of the metal ion binding site may be modified to further tune the sensitivity and responsiveness of the metal ion binding site. The affinity of the metal ion binding site for the metal ion may be varied by selectively manipulating and adding helices, loops, bridges and/or linkers and chemical properties such as hydrogen bonding, electrostatic interactions and hydrophobic interactions. In fact, such variations in tertiary structure may add stability and affinity by increasing secondary structure propensity, adding charge interaction of the side chains, and by stabilizing the metal ion binding coordination chemistry. As such, it may be possible to increase or decrease the binding affinity of the continuous binding site by tuning the tertiary structure of the metal ion binding site. In addition, the dynamic properties can be modified by increasing the packing of the protein and replacing residues with amino acids or other moieties with more rigid (e.g., Pro) or flexible (e.g., Gly) properties, One method of directly altering the primary, secondary, and/or tertiary structure of the metal ion binding site is by altering the charges in the site. As the charges in any binding site have a significant role in the structure of the site, changing the charges or charge ratio may have significant impact on the structure of the site. In addition, as the charged side chains exhibit a strong influence on the metal ion binding affinity even though they are not directly involved as ligands, the variation of these chains results in variations in metal ion binding affinities and selectivity. A metal ion binding site may have stronger affinities to and better selectivity for a desired metal ion over a competitive metal ion by designing or modifying the site, e.g., changing the number of charged ligand residues to form metal ion binding pockets. For example, the metal ion binding affinity of the metal ion binding site may be varied by changing the charged side chains that are present on the metal ion binding site and/or the neighboring environment. The replacement of charged residues such as aspartate or glutamate with a residue such as alanine may dramatically reduce the binding affinity for the metal ion by up to 100 times.

In the case of multifunctional contrast agents, e.g., where the contrast agent is a fluorescent protein, it can be a factor to induce the metal binding site without altering significantly the chromophore environment to reduce the fluorescent signal. These metal binding sites can be added at remote locations away from the chromophore or simply fusion to the fluorescent moieties. Such locations can be evident from the sequence and protein folding.

In another embodiment, the grafting approach may be used with the design approach to create an optimal metal binding site. For example, metal binding sites can be created by using part of continuous site and part of ligand residues created by computer design. The loops or any sequences of the proteins can be removed or modified to achieve optimal required binding affinity, metal selectivity, relaxivity and stability.

Thus, by varying the primary, secondary, and/or tertiary structure of the metal ion binding site, it is possible to achieve a metal ion binding site with desired specificity and affinity and more importantly contrast abilities.

The Modification Method of Natural Metal Binding Proteins

Natural metal binding proteins' their metal binding affinity can be altered by directly modifying the proteins such as the addition of metal ligand residues in the calcium binding proteins to increase metal binding affinity to lanthanides. In an embodiment, fragments and/or domains of the natural metal binding proteins encompassing metal binding sites can also serve as scaffold protein of the contrast agents if they exhibit strong metal binding affinity for $Ln^{3+}$ or other paramagnetic metal ions, serum stability, and desired relaxation properties. The affinity to natural metal ions such as physiological metal ions, e.g., calcium, zinc, and magnesium, will be significantly reduced by deleting metal binding ligand residues or reducing the cooperativity between coupled metal binding sites. As noted in Example 3, the calcium binding sites in the natural calcium binding protein such as calmodulin and parvalbumin were modified so that the modified proteins have a strong metal binding affinity to lanthanides. On the other hand, the metal selectivity for lanthanides over calcium, magnesium and zinc are very high. If it is necessary, the molecular recognition sites of these natural calcium binding proteins can be altered by deletion at the active sites or PEGylation.

In addition, sequences for N- and C-terminal domains of calmodulin and its variants are listed that can be serve as a protein contrast agents (See sequences included herein). Additional modifications can performed to reduce their intrinsic biological function, avoid immunogenicity, increase serum stability, and targeting capability.

Selecting Metal Ion Binding Sites in the Scaffold Protein

The metal ion binding sites may be selectively introduced into numerous sites of a scaffold protein without substantially impairing its secondary structure. A number of methods for identifying integration sites in proteins, such CD2 proteins, fluorescent proteins (e.g., GFP, YFP, CFP, and RFP) are known in the art, including, for example, site directed mutagenesis, insertional mutagenesis, and deletional mutagenesis. Other methods, including the one exemplified below and in the Examples, are known or easily ascertained by one skilled in art.

The sites of the fluorescent protein that can tolerate the insertion of a metal ion binding site also may be determined and identified by gene manipulation and screening. By generating mutant proteins and by manipulating the DNA sequence, it is possible to obtain a variety of different insertions, which then may be screened to determine whether the protein maintains its intrinsic activities. Preferably, sites that remove or interfere with the intrinsic fluorescence of the fluorescent protein are not optimal and may be screened out. Variants identified in this fashion reveal sites that can tolerate insertions while retaining fluorescence.

The metal ion binding sites for use with scaffold proteins may be selected by considering five criteria so to as optimize the local properties of the metal binding site, the fluorescent protein, and the protein environment. First, the geometry of the metal ion binding site should have relatively minor deviations from the desired coordination geometry. Second, negatively charged residues should be varied by no more than 3-5 charges according to the desired affinity for metal ion (K). Third, the water coordination shell of the metal ion chelating sites should be able to coordinate at least 1-2 water molecules. Fourth, the residues from the loops between the secondary structures with good solvent accessibility are desired for both the folding of the protein and the fast kinetics required for the contrast agent.

The mutation or the introduction of the metal ion binding site should not substantially interfere with the synthesis and folding of the protein. More particularly, the introduction of the metal ion binding site does not interfere with either post-translational chromophore formation or intermolecular interactions required for stabilizing the chromophores and folding of the protein frame. Furthermore, the introduced side chain should not be overpacked and should not clash with the protein frame of the scaffold protein (e.g., the fluorescent protein). The direct use of chromophore residues as chelating sites is not preferred but is within the scope of this disclosure.

In an embodiment, the metal binding sites in the natural metal binding proteins can be directly modified to have proper metal binding affinity to the desired metal ions.

Metal Ions

One or more metal ions are atoms and ions, including the respective isotopes and radioisotopes, that can bind to proteins or peptides. A metal ion may bind reversibly or irreversibly and such a bond may be covalent or non-covalent. While $Gd^{3+}$ is used in some embodiments of this disclosure as an exemplary metal ion, it is understood that metal ions suitable with this disclosure include, but are not limited to metal ions including Group IIA metal ions, transition metal ions, and Lanthanide Series ions. Exemplary metal ions include, but are not limited to, the ion, isotope, and/or radioisotope forms of magnesium, calcium, scandium, titanium, manganese, iron, boron, chromium, cobalt, nickel, cooper, zinc, gallium, strontium, yttrium, strontium, technetium, ruthenium, indium, hafnium, tungsten, rhenium, osmium, and bismuth. Exemplary radioisotopes include, but are not limited to, $^{64}Cu$, $^{67}Cu$, $^{67}Ga$, $^{68}Ga$, $^{88}Y$, $^{89}Sr$, $^{90}Y$, $^{97}Ru$, $^{99m}Tc$, $^{103}Ru$, $^{111}In$, $^{153}Sm$, $^{186}Re$, $^{188}Re$, $^{203}Pb$, $^{211}Bi$, $^{212}Bi$, $^{213}Bi$, and $^{214}Bi$.

The metal ions chosen to be chelated by the contrast agents depend in part on the diagnostic role of the metal ion. Metals that can be incorporated, e.g., through chelation, include lanthanides and other metal ions, including isotopes and radioisotopes thereof. For MR imaging applications, the preferred metal ion is gadolinium (III). One of ordinary skill in the art can select a metal ion for chelation, based on the intended diagnostic application, without undue experimentation.

As mentioned, the choice of metal ions to be held in chelate complexes by the contrast agents of the disclosure depends upon the diagnostic technique for which the agent is to be used. For MRI or MRS applications, the metal ions should be paramagnetic, and preferably non-radioactive. For X-ray and ultrasound imaging, heavy metal ions, e.g., with atomic numbers of at least 37, and in an embodiment, at least 50, should be used, again preferably non-radioactive species. For scintigraphy the metal ions should be ions of radioactive isotopes. For MR, X-ray, EIT or magnetometric imaging, one may use chelating groups to bind to heavy metal clusters (e.g., polyoxoanions and full or partial sulfur analogues) or to iron oxides or other superparamagnetic polyatomic species.

Methods of complexing metal ions with chelants and polychelants are known to those with ordinary skill in the art. Metal may be incorporated into the contrast agent, i.e., the tailored binding sites, by direct incorporation, template synthesis, and transmetallation. Preferably, the metal ion is chelated into the contrast by direct incorporation, which involves titration with solution of sub-stoichiometric levels up to full incorporation.

In an embodiment, one or two or more metal ions can bind to the contrast agent. In an embodiment, the contrast agent includes one or two or more metal ion binding sites. In an embodiment, each of the metal ion binding sites binds to the same metal ion. In an embodiment, each of the metal ion binding sites binds to a different metal.

Methods of Use

Embodiments of the contrast agents (e.g., contrast agents including PEGs or not including PEGs, and/or including targeting agents or not including targeting agents) can be used in any one of a number of methods. Embodiments of this disclosure include, but are not limited to: methods of detecting, studying, monitoring, evaluating, and/or screening, diseases, conditions, and other biological events in vivo or in vitro. The conditions can include, but are not limited to, altered growth rate of tissues, cancerous transformation of tissues, inflammation or infection of a tissue, altered volume of a tissue, altered density of a tissue, altered blood flow in a tissue, altered physiological function, altered metabolism of a tissue, loss of tissue viability, presence of edema or fibrosis in a tissue, altered perfusion in tissue, and combinations thereof. In particular, embodiments of the present disclosure include: methods of imaging tissue; methods of diagnosing the presence of a disease, precancerous cells or tissue, cancer cells or tissue cancer, and tumors, as well as related biological events; methods of monitoring the progress of a disease, precancerous cells or tissue, cancer cells or tissue cancer, and tumors, as well as related biological events; and the like.

Embodiments of the present disclosure include, but are not limited to, imaging, detecting, studying, monitoring, evaluating, and/or screening biological materials (e.g., organs, tissues, tumors, cells, and the like), in vivo or in vitro. The tissue types that can be studied using the methods of the present disclosure include, but are not limited to, myocardial tissues, nervous tissue, lymphoid tissue, skeletal and smooth muscle tissue, bones and cartilages, tissues of various organs (e.g., the kidney, the liver, the spleen, the prostate, the uterus, the testicles, and the ovaries), and select portions of each.

Embodiments of the methods can use one or more types of detecting or imaging systems such as, but not limited to, magnetic resonance imaging (MRI), SPECT, PET, ultrasound, X-ray, CAT, optical imaging, and combinations thereof. In an embodiment, the contrast agent is a multimodality contrast agent that includes a polymer having optical properties (GFP). Thus, the polymer having optical properties can be detected using optical imaging, while the metal can be detected using another technique such as a MRI system.

In general, embodiments of the contrast agent are administered to a host using one or more techniques or routes (e.g., oral, mucosal, parenteral, and the like). After an appropriate amount of time, the host can be introduced to an appropriate detection or imaging system. The detection or imaging system can detect the contrast agent. In particular, the detection or imaging system can detect the location(s) of the contrast agents, the concentration of the contrast agent, and the like. The information obtained from the detection or imaging system can be used to create or form an image of the host or a portion thereof. The image would include the position and/or concentration of the contrast agent in the host.

In an embodiment, the contrast agents can be used to study, image, diagnose the presence of, and/or treat cancerous cells or tissue, precancerous cells or tissue, cancer, or tumors. For example, the presence and location of the cancerous cells or tissue, precancerous cells or tissue, cancer, or tumors can provide insight into the appropriate diagnosis and/or treatment. It should be noted that contrast agents could include targeting agents specific for other diseases or conditions so that other diseases or conditions can be imaged, diagnosed, and/or treated using embodiments of the present disclosure. In an embodiment, other diseases and/or conditions can be studied, imaged, diagnosed, and/or treated in a manner consistent with the discussion below as it relates to cancerous cells, precancerous cells, cancer, and/or tumors.

In an embodiment, the contrast agent can be used to study, image, diagnose the presence of, and/or treat cancerous cells or tissue, precancerous cells or tissue, cancer, or tumors. In studying, imaging, diagnosing, and/or treating cancerous cells or tissue, precancerous cells or tissue, cancer, or tumors in a host, the contrast agent is administered to the host in an amount effective to result in uptake of the contrast agent into the cancerous cells or tissue, precancerous cells or tissue, cancer, or tumors. After administration of the contrast agent, the cancerous cells or tissue, precancerous cells or tissue, cancer, or tumors that takes up the contrast agent is detected using an appropriate imaging system. Embodiments of the present disclosure can non-invasively image the cancerous cells or tissue, precancerous cells or tissue, cancer, or tumors throughout a host.

In an embodiment, the contrast agent includes a targeting agent having an affinity for a specific cancer. Detecting the presence of the contrast agent, in particular, the presence of the contrast agent at the typical location of the specific cancer can be used in the diagnosis of the presence of the cancer (or vice versa). Imaging the host over a time period (e.g., days, weeks, months, or years) can provide information about the progression of the cancer or other disease or condition.

The contrast agent or compositions including the contrast agent may be administered to a subject in an amount effective to achieve the desired result at the appropriate dosages and for the desired periods of time. An effective amount of the contrast agent or compositions may vary according to factors such as the age, body weight, general health, sex, and diet of the host; the time of administration; the route of administration; the rate of excretion of the specific compound employed; the duration of the treatment; the existence of other drugs used in combination or coincidental with the specific compositions employed; the ability of the composition to elicit a desired response in the subject; and like factors well known in the medical arts. An effective amount is also one in which any toxic or detrimental effects (e.g., side effects) of the contrast agent or compositions are outweighed by the therapeutically or diagnostically beneficial effects. The contrast agent or compositions of the disclosure may be administered at a concentration of, for example, about 1 to 3.0 µmole/kg or about 6-20 mM.

Dosage Forms

Unit dosage forms of the contrast agents of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the contrast agents of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions including the contrast agent and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions including the contrast agent and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

Like the amounts and types of excipients, the amounts and specific type of active ingredient in a dosage form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

Kits

This disclosure encompasses kits, which may include, but are not limited to, a contrast agent and directions (instructions for their use (written or electronic)). The components listed above can be tailored to the particular disease or condition to be monitored. The kit can further include appropriate reagents known in the art for administering various combinations of the components listed above to the host organism or patient.

EXAMPLES

Example 1

Rational Design of Protein Based MRI Contrast Agents
Introduction:

This Example describes the rational design of a novel class of magnetic resonance imaging contrast agents with an engineered protein chelated with gadolinium. The design of protein based contrast agents involves creating high coordination $Gd^{3+}$ binding sites in a stable host protein using amino acid residues and water molecules as metal coordinating ligands. Designed proteins show strong selectivity for $Gd^{3+}$ over physiological metal ions such as $Ca^{2+}$, $Zn^{2+}$, and $Mg^{2+}$. These agents exhibit a 20-fold increase in longitudinal and transverse relaxivity values over the current clinically used contrast agent, Gd-DTPA. They provide strong contrast enhancement in vivo with much longer vascular retention time. These protein contrast agents have good biocompatibility and potential functionalities may extend MRI applications in targeting disease markers.

Magnetic resonance imaging (MRI) is a non-invasive technique providing high resolution, three-dimensional images of morphological features as well as functional and physiological information about tissues in vivo. It is capable of detecting abnormalities in deep tissues and allows for whole body imaging. It has emerged as a primary diagnostic imaging technique for human diseases.[1, 2] Exogenous MRI contrast agents are often used to enhance the contrast between pathological and normal tissues by altering the longitudinal and transverse (i.e., $T_1$ and $T_2$) relaxation times of water protons.[3-5] Gadolinium ($Gd^{3+}$) is the most frequently used MRI contrast agent due to its high magnetic moment, asymmetric electronic ground state and potential for increased MRI intensity.[6, 7] The relaxivity (unit capability of the agent to change the relaxation time) of a contrast agent is dependent on several factors including the number of water molecules in the coordination shell, the exchange rate of the coordinated water with the bulk water, and the rotational correlation time $\tau_R$ of the contrast agent.[8-10] The MRI contrast agent can have: 1) high relaxivity for high contrast-to-noise ratio (CNR) and dose efficiency, 2) thermodynamic stability, especially metal selectivity for the target ions over excess physiological metal ions, to minimize the release of toxic paramagnetic metal ions, 3) adequate vascular, tissue retention time to allow imaging, and 4) proper excretion from the body.

To date, the most commonly used MRI contrast agent in diagnostic imaging is Gd-DTPA, or its derivatives such as Gd-DTPA-BMA. With an intrinsic rotational correlation time, $\tau_R$, of 100 picoseconds, these small molecular gadolinium contrast agents have longitudinal and transverse proton relaxivities, $r_1$ and $r_2$, less than 10 $mM^{-1}$ $s^{-1}$, much lower than the theoretically maximal value (>100 $mM^{-1}$ $s^{-1}$).[9, 11] In addition, these small molecule contrast agents exhibit very short blood circulation (within several minutes) and tissue retention time, limiting some MRI applications that require longer data collection time.[12] To increase correlation time, $\tau_R$, small contrast agents were covalently or non-covalently conjugated to macromolecules such as linear polymers,[13] dendrimers,[14,15] carbohydragates,[16] proteins,[17-21] viral capsids,[22] and liposomes[23]. However, conjugation yields limited improvement due to internal mobility and restricted water exchange rate (FIG. 1.1A).[11] An increase in relaxivity was observed when $Gd^{3+}$ binds to calcium binding peptides[24] or proteins such as concannavalin A and bovine serum albumin (BSA).[6] However, the application of these short peptides or proteins as MRI contrast agents is limited due to their weak metal binding affinity for Gd ($K_d$~100 μM for $Eu^{3+}$) and dynamic flexibility.[24, 25]

This Example describes the development of a new class of MRI contrast agents with significantly improved relaxivity using rational design of $Gd^{3+}$-binding proteins. This class of contrast agents was created by designing the metal binding sites into a stable host protein with desired dynamic properties and metal selectivity to increase relaxivity by optimizing local $\tau_R$. This approach provides a new platform for developing MRI contrast agents with high relaxivity and functionality.

Materials and Methods

Determination of $r_1$ and $r_2$ Relaxivity Values.

Relaxation times, $T_1$ and $T_2$, were determined at 1.5, 3, 9.4 Tesla using a Siemens whole-body MR system (1.5, 3T) or a Bruker MRI scanner (9.4T). $T_1$ was determined using inversion recovery and $T_2$ using a multi-echo Carr-Purcell-Meiboom-Gill (CPMG) sequence. The contrast agent samples (200 μl) with different concentrations were placed in eppendorf tubes. The tubes were placed on a tube rack, which was placed in MRI scanners for the measurement of relaxation times. $r_1$ and $r_2$ were calculated based on $r_1$ ($mM^{-1}$ $S^{-1}$)=(1/$T_{1s}$−1/$T_{1c}$)/C and $r_2$ ($mM^{-1}$ $S^{-1}$)=(1/$T_{2s}$−1/$T_{2c}$)/C, where $T_{1s}$ and $T_{2s}$ are relaxation times with contrast agent and $T_{1c}$ and $T_{2c}$ are relaxation times without contrast agent. C is the concentration of contrast agent in mM (the measured $Gd^{3+}$ concentrations by ICP-MS).

Measurement of Water Coordination Number by Terbium Life Time Luminescence.

The number of water ligands coordinated to $Gd^{3+}$-CA1.CD2 complex was determined by measuring $Tb^{3+}$ luminescence decay in $H_2O$ or $D_2O$. $Tb^{3+}$ excited state lifetime was measured using a fluorescence spectrophotometer (Photon Technology International, Inc.) with a 10 mm path length quartz cell at 22° C. Following excitation at 265 nm with a XenoFlash (Photon Technology International, Inc.), $Tb^{3+}$ emission was monitored at 545 nm in a time series experiment in both $H_2O$ and $D_2O$ systems. Luminescence decay lifetime was obtained by fitting the acquired data with a mono-exponential decay function. $H_2O$ in CA1.CD2 solution was replaced with $D_2O$ by lypholization and re-dissolved in $D_2O$ at least three times. A standard curve correlating the $\Delta k_{obs}$ with water number under our experimental conditions was established by using well-characterized chelators, such as EDTA (q=3), DTPA (q=1), NTA (q=5), and Aquo $Tb^{3+}$ (q=9) solution with $R^2$=0.997.[26,27] Water number coordinated to $Tb^{3+}$-CA1.CD2 complex was then obtained by fitting the acquired $\Delta k_{obs}$ value to the standard curve.

$Gd^{3+}$-Binding Affinity Determination.

$Gd^{3+}$-binding affinity of CA1.CD2 was determined by a competition titration with Fluo-5N applied as a $Gd^{3+}$ indicator. The fluorescence spectra of Fluo-5N were obtained with a fluorescence spectrophotometer (Photon Technology International, Inc.) with a 10 mm path length quartz cell at 22° C. Fluo-5N emission spectra were acquired at 500 nm to 650 nm with an excitation at 488 nm. $Gd^{3+}$-binding affinity of Fluo-5N, $K_{d1}$, was first determined by a $Gd^{3+}$ titration with $Gd^{3+}$ buffer system of 1 mM nitrilotriacetic acid (NTA). Free $Gd^{3+}$ concentration was calculated with a NTA $Gd^{3+}$-binding affinity of $2.6 \times 10^{-12}$ M.[28] Fluo-5N was mixed with $Gd^{3+}$ in 1:1 ratio for a competition titration. The experiment was performed with a gradual addition of CA1.CD2. An apparent constant, $K_{app}$, was estimated by fitting the fluorescence emission intensity of Fluo-5N at 520 nm with different CA1.CD2 concentrations as a 1 to 1 binding model. $Gd^{3+}$-binding affinity of CA1.CD2, $K_{d2}$, was calculated with the following equation:

$$K_{d2} = K_{app} \frac{K_{d1}}{K_{d1} + [Fluo-5N]_T} \quad (1)$$

Mouse MR Imaging.

Care of experimental animals was in accordance with institutional guidelines. CD-1 mice (25-30 g, four mice were imaged) were anesthetized with an isoflurane gas mixture. The anesthetized animal was positioned and stabilized with soft-supporting material (e.g., foam) in the scanner in the coil cradle and was kept warm during the MRI scan. The mice were scanned prior to the administration of any contrast agent (pre-contrast). Approximately 50 μl of Gd-CA1.CD2 (~1.2 mM) or Gd-DTPA (~300 mM) were injected into the animal via the tail vein. MR images were collected at different times (indicated). For $T_1$ weighted imaging at 3T, spin echo sequence with TE/TR=15 ms/500 ms was employed. Rectangular Field of View (FOV) at 100/40 mm, an acquisition matrix of $196^2$ and 1.1 mm slice thickness without gap were used. Images were collected from both transverse and coronal sections. The in-plane resolution of images was less than 0.5 mm after they were reconstructed to the matrix of $196^2$. For $T_2$ weighted imaging at 9.4T, MR images were recorded using a multi-echo Carr-Purcell-Meiboom-Gill (CPMG) sequence. The data were collected and processed by Dicomworks software. The MR signal intensity in several organs was ascertained by the average intensity in ROIs or points within the organs. Signal intensity for each organ was normalized to that of the leg muscle.

Blood Circulation Time, Tissue Retention Time, and Bio-Distribution.

CD-1 mice (25-30 g, a group of four mice were tested) were anesthetized with isoflurane. Appropriate dosages of Gd-CA1.CD2 or Gd-DTPA were i.v. injected (via tail vein). Blood (~50 μl) samples were collected via orbital sinus of the mouse at different time points. The mouse was euthanized at the final time point. Tissue samples from kidney, liver, heart, and lung, were collected. Serum samples were prepared from the collected blood. For the bio-distribution analyses, the animals were euthanized at single time point (indicated) after i.v. administration of the contrast agent (indicated). The organ/tissue samples were collected. Tissue extracts were freshly made from collected samples using commercially available tissue extracting kits (Qiagen). CA1.CD2 was detected and quantified by immunoblotting and Sandwich-ELISA using a monoclonal antibody (OX45, detecting antibody) and a home made polyclonal antibody (PabCD2, capture antibody). A series of known amounts of CA1.CD2 samples mixed with blank mouse serum or tissue extracts were used as standard in Sandwich-ELISA. ELISA signal from HRP was monitored using a Fluorstar fluorescence microplate reader. For quantification of $Gd^{3+}$ in the serum and tissue samples one hour (or indicated times) after the contrast agent administration, animals were sacrificed and critical organs were collected, and the tissues were then digested with concentrated nitric acid at 120-130° C. with proper amount of $^{157}Gd$ spike as an internal marker. The digested solution was analyzed by ICP-MS (Element 2) using an isotope dilution method.

Toxicity Analyses.

The MR imaged CD-1 mice that received the i.v. administered Gd-CA1.CD2 (at a dose of ~2.4 μmol/kg) were returned to their cages (one mouse per cage). The mice were observed for five days and were euthanized at the end of the fifth day. Tissue samples from kidney, liver, spleen, and lung were collected. $Gd^{3+}$ ion contents in the tissue samples were analyzed by ICP-MS (see above paragraph).

Two groups of mice were used to examine potential renal and/or liver damage by Gd-CA1.CD2. One group of mice received (i.v. tail veil) 50 μl of saline-buffer (as control). Another group received (i.v. tail veil) Gd-CA1.CD2 at 4 μmole/kg. The mice were observed for 48 hours and were euthanized. Blood samples were collected from the experimental mice. Serum samples were prepared from the collected blood. Liver enzymes in serum samples, including Alanine transaminase (ALT), Alkaline phosphatase (ALP), Aspartate transaminase (AST), Gamma glutamyl transpeptidase (GGT), and bilirubin and urea nitrogen were analyzed by a commercially available source (MU Research Animal Diagnostic Laboratory). All clinical chemistry parameters were measured on an Olympus AU 400 analyzer.

Cytotoxicity was analyzed by MTT assay of the cells that were treated with Gd-CA1.CD2 at appropriate doses (indicated in figure). The cells were grown under normal growth medium in 96 well plates. Gd-CA1.CD2 or saline-phosphate buffer was added to the cell culture medium. The cells were incubated for appropriate times. A standard MTT assay was employed to assess the cell growth status of the treated cells.

Serum Stability.

CA1.CD2 (40 μM) in complex with $Gd^{3+}$ was incubated with 75% human serum over 3 or 6 hours at 37° C. The degradation of the protein (disappearance of 12 kDa protein band) was analyzed by SDS-PAGE and visualized by coomassie blue staining. In parallel, the degradation of the protein was also analyzed by immunoblot using antibodies OX54 or PabCD2. The identities of the 12 kDa bands as CA1.CD2 were always verified by immunoblotting using antibody PabCD2.

Results

Rational Design of $Gd^{3+}$-Binding Proteins.

FIG. 1.1 shows the simulation of the dependence of $r_1$ and $r_2$ on the rotational correlation time, $\tau_R$, of a contrast agent at different magnetic field strengths according to the theory developed by Blombergen, Solomon[6, 7] (for detailed simulation procedures, please see on-line supporting materials). For small molecules such as Gd-DPTA with $\tau_R$ at hundreds of ps, the relaxivity is <10 $mM^{-1} s^{-1}$ regardless of how the other parameters are adjusted. On the other hand, the simulation clearly suggests that contrast agents with $\tau_R$ of 10-50 ns have the highest $r_1$ and $r_2$ values at clinically relevant magnetic field strengths from 0.47-4.7 Tesla (T).[11] Thus, we envisioned that high-relaxivity MRI contrast agents can be developed by directly designing $Gd^{3+}$ binding sites in proteins with desired $\tau_R$. Coordinating $Gd^{3+}$ ions directly to the rigid protein frame eliminates the high internal mobility associated with chelator-macromolecule conjugates (FIG. 1.1A).

We chose domain 1 of rat CD2 (referred to as CD2), a cell adhesion protein with a common immunoglobin fold, as a scaffold (FIG. 1.1C). CD2 protein exhibits strong stability against pH changes and excellent tolerance against various mutations,[29] which are essential features of functional protein engineering. In addition, it has a compact structure with rotational correlation time, $\tau_R$, of ~10 ns, corresponding to optimal relaxivity for the current clinically allowed magnetic field strength.[30] Moreover, its molecular size (12 kDa) is suitable for good tissue penetration and easy renal exclusion.[17]

We next designed a series of $Gd^{3+}$ binding sites into CD2 using computational methods.[32, 33] The design was based on the established structural parameters obtained from detailed analysis of metal binding sites in over 500 small chelators and metalloproteins. $Gd^{3+}$, $Tb^{3+}$, $La^{3+}$ and other $Ln^{3+}$ ions have coordination properties similar to those of $Ca^{2+}$ with a strong preference for oxygen ligand atoms.[34] Small chelators usually have on average 9.3 and 6.9 total coordinating atoms for $Gd^{3+}$ and $Ca^{2+}$, respectively. For example, DTPA has 5 oxygen ligand atoms and 2 nitrogen ligand atoms. For macromolecules such as proteins, the coordination atoms are almost always oxygen atoms, and the coordination numbers are lower than small chelators with an average of 7.2 for $Ln^{3+}$ and 6.0-6.5 for $Ca^{2+}$. These effects are possibly due to steric crowding and sidechain packing.[34] Previously, we successfully designed $Ca^{2+}$ and $Ln^{3+}$ binding sites in a scaffold protein with strong selectivity over excess physiological metal ions.[35] Structure determination by solution NMR revealed that the actual coordination geometry in a designed variant is the same as our design, verifying the computational methods and the design strategy of metal-binding sites in proteins.[31]

The designed proteins were named CA1.CD2-CA9.CD2 reflecting Gd-binding sites at different locations. FIG. 1.1C shows an example of designed $Gd^{3+}$-binding protein CA1.CD2 with a metal binding site formed by the six potential oxygen ligands from the carboxyl side chains of Glu15, Glu56, Asp58, Asp62 and Asp64. Based on our studies of charged residues in the coordination shell,[36] we placed 5 negatively charged residues to provide these six oxygen ligand atoms in the coordination shell of CA1.CD2 to increase the selectivity for $Gd^{3+}$ over $Ca^{2+}$. To achieve the desired relaxation property, one position of the metal binding geometry was left open in the design to allow fast water exchange between the paramagnetic metal ion and the bulk solvent (FIG. 1.1A). The $Gd^{3+}$-binding site has minimal internal flexibility as the ligand residues originate from rigid stretches of the protein frame. To test the requirement for rigid embodiment in achieving high relaxivity, another $Gd^{3+}$-binding protein, CA9.CD2, was engineered by fusing a continuous cation-binding EF-hand loop from calmodulin with flexible glycine linkers to the host protein.[37,38] This protein mimics previously reported highly flexible chelate-based contrast agents conjugated to macromolecules.[24, 25]

All of the designed $Gd^{3+}$ binding proteins were expressed in E. coli and subsequently purified by procedures previously published from our laboratory.[30, 31] All of the designed proteins form the expected metal:protein complex as demonstrated by ESI-Mass spectrometry (FIG. 1.5). Since metal selectivity for $Gd^{3+}$ over other physiological metal ions is for minimizing the toxicity of the agents,[39, 40] we measured metal binding constants using dye-competition assays with various chelate-metal buffer systems (Table 1). Low limit metal binding affinities of the proteins were also estimated based on $Tb^{3+}$-sensitized FRET and competition assays. CA1.CD2 exhibited disassociation constants ($K_d$) of $7.0 \times 10^{-13}$, $1.9 \times 10^{-7}$, $6 \times 10^{-3}$, and $>1 \times 10^{-2}$ M for $Gd^{3+}$, $Zn^{2+}$, $Ca^{2+}$, and $Mg^{2+}$, respectively. The selectivity $K_d^{ML}/K_d^{GdL}$ for $Gd^{3+}$ over physiological divalent cations $Zn^{2+}$, $Ca^{2+}$, and $Mg^{2+}$ are $10^{5.34}$, $>10^{9.84}$, and $>10^{10.06}$, respectively. The metal selectivity of CA1.CD2 is significantly greater than or comparable to that of FDA approved contrast agents DTPA- and DTPA-BMA[40] (Table 1). The high metal binding selectivity of CA1.CD2 was further supported by the observation that $r_1$ and $r_2$ of Gd-CA1.CD2 were not altered in the presence of excess $Ca^{2+}$ (10 mM) (FIG. 1.2). Further assays showed that potential chelators in serum, such as phosphate (50 mM), were not able to remove the $Gd^{3+}$ from the protein. This is considered for in vivo applications of the contrast agent as the phosphate concentration in serum is maintained at ~1.3 mM.[6,9] The stability of a contrast agent in blood circulation is another factor for in vivo applications. We characterized the stability by incubating Gd-CA1.CD2 with 75% human serum at 37° C. for 3 and 6 hours. The protein-Gd complex remained intact after 6 hours of incubation. The result suggests that the protein is stable in blood. Taken together, the designed protein contrast agent is comparable to the clinically used contrast agents with good metal binding stability and selectivity.[6,7]

TABLE 1

Example 1. Metal binding constants (Log $K_a$) and metal selectivity of DTPA, DTPA-BMA and CA1.CD2

| Sample | $Gd^{3+}$ | $Zn^{2+}$ | $Ca^{2+}$ | $Mg^{2+}$ | Log ($K_{Gd}/K_{Zn}$) | Log ($K_{Gd}/K_{Ca}$) | Log ($K_{Gd}/K_{Mg}$) |
|---|---|---|---|---|---|---|---|
| DTPA[28] | 22.45 | 18.29 | 10.75 | 18.20 | 4.17 | 11.70 | 4.25 |
| DTPA-BMA[41] | 16.85 | 12.04 | 7.17 | na* | 4.81 | 9.68 | na* |
| CA1.CD2 | 12.06 | 6.72 | <2.22 | <2.0 | 5.34 | >9.84 | >10.06 |

*na: not available.

The Designed Gd-Binding Proteins Exhibit High $r_1$ and $r_2$ Relaxivity.

We have determined the relaxivity values of the designed protein contrast agents at 1.5, 3.0 and 9.4 Tesla field strengths (FIG. 1.2). FIG. 1.2A shows that, at a concentration of 50 μM, the designed contrast agents Gd-CA1.CD2 and Gd-CA2.CD2 were able to introduce contrast enhancement in T1 weighted imaging at 3.0 T while 100 μM Gd-DTPA and protein CA1.CD2 alone did not lead to significant enhancement. The in vitro relaxivity values of the designed Gd-binding proteins were measured (Table 2). Gd-CA1.CD2 exhibits $r_1$ up to 117 $mM^{-1} s^{-1}$ at 1.5T, about 20-fold higher than that of Gd-DTPA. In contrast, Gd-CA9.CD2, which carries a flexibly-conjugated $Gd^{3+}$-binding site, had significantly lower relaxivity values (3.4 and 3.6 $mM^{-1} s^{-1}$, for $r_1$ and $r_2$ respectively, at 3.0 T), that are comparable to those of Gd-DTPA (Table 2). These data support the concept that elimination of the intrinsic mobility of the metal binding site resulted in the desired high relaxivity values.

TABLE 2

Example 1. Proton relaxivity of different classes of contrast agents

| CA class | Compounds (ligand residues) | $r_1$ (mM$^{-1}$ s$^{-1}$) | $r_2$ (mM$^{-1}$ s$^{-1}$) | B0 (T) | MW (kDa) |
| --- | --- | --- | --- | --- | --- |
| Designed proteins | CA1 (E15/E56/D58/D62/D64) | 117 | 129 | 1.5 | 12 |
| | | 48 | 88 | 3 | |
| | | 6 | 50 | 9.4 | |
| | CA2 (D15/D17/N60/D62) | 35 | 58 | 3 | 12 |
| | CA3 (E15/E56/D58/D62/E64) | 130 | | 1.5 | 12 |
| | | 34 | 57 | 3 | |
| | CA9 (Add EF-loop III from Calmodulin) | 3.5 | 3.6 | 3 | 12 |
| Small compound | GdDTPA | 5.4 | 8 | 1.5 | |
| | | 4.2 | 6.8 | 3 | 0.743 |
| *Protein carriers | Albumin | 11.5 | 12.4 | 0.25 | 80 |
| | Poly-lysine | 13 | 15 | 0.47 | 52 |
| *Dendrimers | Gadomer-17 | 13 | | 1.5 | 35 |
| *Liposome | ACPL | 12 | 11 | 1.5 | >10$^3$ |
| *Nanoparticle emulsion | Gd-perfluorocarbon nanoparticles | 34 | 50 | 1.5 | >10$^3$ |

*Based on references.[17,19-21]

The $r_1$ and $r_2$ of Gd-CA1.CD2 exhibited an inverse relationship with the magnetic field strength (Table 2, Example 1). In contrast, the $r_1$ and $r_2$ of Gd-DPTA showed weak dependence on field strengths. The magnetic field strength dependent changes in relaxivity are consistent with our simulation results based on the rotational IR of the contrast agent (FIG. 1.1B). The results showed that the protein contrast agent offers much higher relaxivities for MRI contrast enhancement at clinical magnetic field strengths (1.5-3.0 T). Interestingly, the transverse relaxivity of designed contrast agent is very high (i.e. >50 mM$^{-1}$ s$^{-1}$) at 9.4T compared to Gd-DTPA, making it appropriate as a $T_2$ contrast agent (Table 2) at high fields. It should be pointed out that $r_2$ of our protein-based contrast agent is smaller than the currently used $r_2$ agents such as iron oxides.[42] This property allows our contrast agents to fill a gap between small Gd-chelators and iron oxide nanoparticles, extending the range of MRI applications both at clinically relevant field strength and possibly higher field strength.

One factor that contributes greatly to the relaxivity of an MRI contrast agent is its rotational correlation time, $\tau_R$.[11, 30, 31] Dynamic NMR studies showed that the overall correlation time of our designed protein (CA1.CD2) is similar in the absence (9.20 ns) and presence of bound metal ions (9.08 ns), consistent with that for proteins of similar size.[43] The values of the order factor $S^2$ of the ligand residues are similar to the average value of the protein, suggesting that the metal binding pocket tumbles with the protein as a whole (FIG. 1.3A). Therefore, the measured correlation time of the protein directly reflects the $\tau_R$ of the metal binding site. In contrast, the flexible metal binding loop in CA9.CD2 has an $S^2$ order value of 0.3-0.4, which is very different from CA1.CD2 with an $S^2$ value very close to that of the backbone of the protein.

The hydration number of an MRI contrast agent is another determinant for $r^1$ and $r^2$. The hydration number of the designed protein-based contrast agents was determined by measuring the luminescence lifetime of Tb$^{3+}$.[26] The free Tb$^{3+}$ in H$_2$O and D$_2$O has a life time value of 410 s and 2,796 s, respectively. The formation of M-protein complex significantly increases Tb$^{3+}$ life time to 859 μs. The Tb$^{3+}$ life time values of CA1.CD2 were 1,679 s in D$_2$O, suggesting a hydration number of 2.1 (FIG. 1.3B). Interestingly, a well-known Ca$^{2+}$-binding protein troponin C exhibits a hydration number of 1.8 (FIG. 1.3B). It was determined by the X-ray crystal structure that trponin C has only one water molecule coordinated Tb$^{3+}$ in the metal binding pocket.[44] Therefore, it is conceivable that the hydration water molecules either from the coordination shell or the outer shell of the protein also contribute to the observed high relaxivity of CA1.CD2.

Application of the Designed Gd-Binding Proteins for In Vivo MR Imaging.

The effect of MRI contrast enhancement of the protein contrast agent was tested in mice (CD-1 mice). Gd-CA1.CD2 was administered via tail vein at a dose of ~2.4 μmole Gd/kg body weight, about 35 fold lower than the dosage of Gd-DTPA used in diagnostic imaging. Comparison of pre- and post-contrast $T_1$ weighted spin echo images obtained at 3T showed the contrast enhancement in several organs with the greatest enhancement of the MRI contrast observed in the kidney (FIG. 1.4A, arrows indicated), which exhibited a time dependent change of the contrast enhancement over a period of 2 hours (FIG. 1.4B). Careful analysis of image data showed the distribution of the contrast enhancement at different organs (FIG. 1.4B). The tissue dependent enhancement is consistent with the biodistribution of Gd$^{3+}$ analyzed at 1 hour time point using inductively coupled plasma mass spectrometry (ICP-MS) (FIG. 1.4C). The $T_1$ contrast enhancement in the kidney cortex diminished substantially at 18 hours after the administration of Gd-CA1.CD2, suggesting that the agent was gradually cleared from the kidney and other organs. Consistent with the simulations and relaxivity values determined in vitro, a strong $T_2$ contrast enhancement was observed at 9.4T. $T_2$-weighted images at the 9.4T and $T_1$-weighted images at 3T showed very similar tissue and organ distribution patterns (FIGS. 1.7A and 1.7B). At the same concentration, Gd-DTPA failed to exhibit contrast enhancements at either 3T or 9.4T.

Furthermore, contrast enhancement by Gd-CA1.CD2 was sustained over 4-7 hours at multiple organs (FIG. 1.8B), indicating much longer tissue retention time of the agent than that of Gd-DTPA. The tissue retention and blood circulation time of Gd-CA1.CD2 in mice were characterized by administering various doses of agents in mice and analyzing the collected blood samples or tissue sections from sacrificed animals using immunoblots and ELISA with monoclonal (OX45) and in-house developed polyclonal (PabCD2) antibodies. In contrast to the short blood circulation time of Gd-DPTA, Gd-CA1.CD2 exhibited a prolonged blood circulation time. No significant decrease in the CA1.CD2 levels in blood was observed until 45 minutes after i.v. administration. The protein remained in blood circulation for more than 3 hours (FIG. 1.8A). This property is considered for imaging of biological events that require prolonged imaging time, or imaging of pathological features that require time for delivery of the agent to the targeted site. In the kidney, CA1.CD2 was first detectable at 15 minutes and peaked at 4-5 hours. There was less than 10% of the injected dose of the contrast agent remaining in the kidney 15 hours after injection (by measurements of both $Gd^{3+}$ and CA1.CD2). This result, along with the observation of MRI contrast changes in the bladder, suggests a clearance of the agent by kidney.

Gd-CA1.CD2 did not exhibit acute toxicity at the dose (~2.4 µmole/kg) used for MRI. All mice that received the contrast agents (>10) showed no adverse effects before euthanization five days after agent injection. The effects of Gd-CA1.CD2 on liver enzymes (ALT, ALP, AST), serum urea nitrogen, bilirubin, and total protein from CD-1 mice 48 hours post-contrast injection were negligible compared to those in the control mice (Example 1, Table 3). In addition, no cytotoxicity was observed in tested cell lines, SW620, SW480 and HEK293, that were treated with 50 µM Gd-CA1.CD2, by MTT assay (FIG. 1.8B). Based on the preliminary characterization of toxicity, we conclude that the protein contrast agent did not possess acute toxicity at current dosages for mice.

TABLE 3

Example 1. Summary of Animal Clinical Pathology Profiles

| | Test mice[a] | Control mice[b] | Normal range[c] |
|---|---|---|---|
| Urea Nitrogen (mg/L) | 26.0 ± 0.2[d] | 27.0 ± 0.2 | 18-31 |
| Total Urine Protein (g/L) | 5.2 ± 0.2 | 5.3 ± 0.2 | 5.9-10.3 |
| Total Bili (mg/L) | 0.4 ± 0.2 | 0.5 ± 0.2 | 0.3-0.8 |
| Direct Bili (mg/L) | 0.0 | 0.0 | |
| ALT (U/L) | 49.0 ± 0.2 | 72.0 ± 0.2 | 44-87 |
| ALP (U/L) | 115.0 ± 0.2 | 302.0 ± 0.2 | 43-71 |
| AST (U/L) | 280.0 ± 0.2 | 219.0 ± 0.2 | 101-214 |
| GGT (U/L) | 0.0 | −3.0 | |

[a]Four mice per group were injected with Gd-CA1.CD2 at dose of 4.0 µmole/kg. All clinical chemistry parameters are measured on an Olympus AU 400 analyzer by MU Research Animal Diagnostic Laboratory (details see Material and Methods).
[b]Control group mice were injected with 50 µl of phosphate buffered saline pH = 7.4.
[c]Normal range values are from Quesenberry, K. E. and J. W. Carpenter; Ferrets, Rabbits, and Rodents Clinical Medicine and Surgery; W. B. Saunders: Philadelphia, 2003.
[d]The standard deviations of measurements with four animal (n = 4).

DISCUSSION

While new developments of $Gd^{3+}$ chelators[4, 5, 11, 21, 46] continue to expand the applications of small molecular contrast agents, macro-molecular agents are increasingly attractive for functional and molecular imaging applications. A common approach of using small molecular GdDTPA to bind albumin in serum (e.g., MS-325) has the capability to enhance the relaxivity in vivo. However, this class of contrast agents is currently limited to imaging the vascular system[47-50] with the complex pharmacokinetics.[51] Conjugation or encapsulation of small Gd-chelators to or in the liposome, fullerene, and nanotube, indeed resulted in increases in relaxivity; however, several important drawbacks limit the applications of these agents. Our approach of using an engineered protein to chelate the $Gd^{3+}$ for contrast enhancing effect differs fundamentally from those previous studies in several respects.

First, we have created a $Gd^{3+}$-binding site with strong metal selectivity in a stable and potentially fully functioning host protein by de novo design. This is significantly different from using a small peptide fragment to cross-link small $Gd^{3+}$-chelate in stability and rigidity of the binding site as well as biological functions of the protein. To our knowledge, this is the first example that an MRI protein contrast agent was made using an engineered $Gd^{3+}$ binding protein without using existing small metal chelators. This is an achievement in protein design, involving the rational development of a metalloprotein with high coordination number and charged ligand residues in the coordination shell.

Second, our approach provides a new platform for developing MRI contrast agents with further improved relaxivity and metal selectivity and stability by protein engineering. Our studies reveal that three factors are key in achieving high relaxivity: 1) the longer rotational correlation time $\tau_R$ of the designed agents, 2) the direct coordination of $Gd^{3+}$ ions to amino acid ligands at the rigid protein matrix to eliminate internal mobility, and 3) the increased hydration of water molecules. As predicted by the Solomon-Bloembergen-Morgan equation (Supplementary Equation 1), relaxivities can be significantly increased by increasing the number of hydration water molecules. Unfortunately, previous attempts to increase relaxivities by increasing the number of coordinating water molecules from 1 to 2 for BTPA and DTPA-BMA did not yield successful results. Our studies demonstrated an excellent example that it is possible to increase in relaxivity by increasing the hydration number of protein MRI contrast agent without sacrifice the metal binding properties, such as affinity and metal specificity. Presumably, the concept demonstrated in this study may be applied to the design of other macromolecule based MRI contrast agents. Using protein to chelate $Gd^{3+}$ as an MRI contrast agent has several potential advantages over currently used Gd-DTPA in functional and molecular imaging applications: 1) it greatly increases the contrast-to-noise ratio (CNR); 2) it improves dose efficiency with reduced metal toxicity; 3) it prolongs the tissue retention time, which enables imaging of abnormalities that requires prolonged tissue enhancement; and 4) provide a potential functioning protein or a protein carrier that can conjugate target specific ligands to a biomarker for targeted molecular MR imaging.

ESI-Mass spectrometry of metal:protein complex, determination of metal binding constants, MRI imaging and its data analysis, tissue retention and blood circulation time of contrast agents, toxicity, and simulation of contrast agent relaxivities.

Computational Simulation of Contrast Agent Relaxivities[52]

The simulation of $R_1$ and $R_2$ as a function of magnetic field strength is performed based on supplementary equations 1 and 2:

$$R_1 = \frac{cq}{55.5} \frac{1}{T_{1m} + \tau_m} \quad (1)$$

$$R_2 = \frac{cq}{55.5} \frac{T_{2m}^{-2} + \tau_m^{-1} T_{2m}^{-1} + \Delta\omega_m^2}{\tau_m((\tau_m^{-1} + T_{2m}^{-1})^2 + \Delta\omega_m^2)} \quad (2)$$

In these equations, the water coordination number, q, is assumed to be 1 and the agent concentration is 0.001 M; $\tau_m$ is the dwelling time of the coordination water; and $\Delta\omega_m$ is the chemical shift difference between the bound and free water. Since $\Delta\omega_m^2$ is much smaller than other components, equation 2 is simplified to supplementary equation 3 and used in this simulation:

$$R_2 = \frac{cq}{55.5} \frac{1}{T_{2m} + \tau_m} \qquad (3)$$

$T_{im}$ is determined by dipole-dipole (DD) and scalar or contact (SC) mechanisms as shown in supplementary equation 4:

$$\frac{1}{T_{im}} = \frac{1}{T_i^{DD}} + \frac{1}{T_i^{SC}} \quad i = 1, 2 \qquad (4)$$

Because the contribution from $T_i^{DD}$ is much greater than that of $T_i^{SC}$, only the former is used in the simulation, which is obtained using supplementary equations 5 and 6:

$$\frac{1}{T_1^{DD}} = \frac{2}{15} \frac{\gamma_I^2 g^2 \mu_B^2}{r_{GdH}^6} S(S+1) \left(\frac{\mu_0}{4\pi}\right)^2 \left[\frac{7\tau_{c2}}{1+\omega_s^2\tau_{c2}^2} + \frac{3\tau_{c1}}{1+\omega_I^2\tau_{c1}^2}\right] \qquad (5)$$

$$\frac{1}{T_2^{DD}} = \frac{1}{15} \frac{\gamma_I^2 g^2 \mu_B^2}{r_{GdH}^6} S(S+1) \left(\frac{\mu_0}{4\pi}\right)^2 \left[\frac{13\tau_{c2}}{1+\omega_s^2\tau_{c2}^2} + \frac{3\tau_{c1}}{1+\omega_I^2\tau_{c1}^2} + 4\tau_{c1}\right] \qquad (6)$$

The following values are used in the calculation: the gyro-magnetic constant for proton $\gamma_I$, $2.675\times10^8$ T$^{-1}$ s$^{-1}$; g, 2.0; Bohr magneton $\mu_B$, $9.274\times10^{-24}$ J T$^{-1}$; S, 7/2; permeability of vacuum $\mu_0$, $1.257\times10^{-6}$ N A$^{-2}$; and the distance between the Gd$^{3+}$ and proton $r_{GdH}$, $3.0\times10^{-10}$ m (normally 2.7-3.3 Å). The frequency of proton $\omega_I$ equals to the $\gamma_I$ multiplied by the magnetic field while the frequency of electron $\omega_s$ is 658-fold of $\omega_I$. The $\tau_{ci}$ is determined by the rotational correlation time $\tau_R$, the water dwelling time $\tau_m$, and $T_{ie}$ as shown in supplementary equation 7:

$$\frac{1}{\tau_{ci}} = \frac{1}{\tau_R} + \frac{1}{\tau_m} + \frac{1}{T_{ie}} \quad i = 1, 2 \qquad (7)$$

$T_{ie}$ is related to the electron frequency $\omega_s$ as well as the $\tau_v$ (correlation time of splitting) and $\Delta^2$ (mean square zero field splitting energy) of the Gd$^{3+}$ as in supplementary equations 8-10:

$$\frac{1}{T_{1e}} = 2C\left(\frac{1}{1+\omega_s^2\tau_v^2} + \frac{4}{1+4\omega_s^2\tau_v^2}\right) \qquad (8)$$

$$\frac{1}{T_{2e}} = C\left(\frac{5}{1+\omega_s^2\tau_v^2} + \frac{2}{1+4\omega_s^2\tau_v^2} + 3\right) \qquad (9)$$

Where $$C = \frac{1}{50}\Delta^2\tau_v\{4S(S+1)-3\} \qquad (10)$$

Various combinations of $\tau_R$ (1 ps, 10 ps, 100 ps, 1 ns, 10 ns, and 100 ns), $\tau_m$ (1 ps, 10 ps, 100 ps, 1 ns, 10 ns, and 100 ns), $\tau_v$ (1 and 10 ps), and $\Delta^2$ ($10^{17}$, $10^{18}$, $10^{19}$, and $10^{20}$ s$^{-2}$) have been proposed for the calculation of magnetic field-dependent relaxivities under magnetic field strengths ranging from 0.001 MHz to more than 1000 MHz. For small molecules such as DPTA with $\tau_R$ at hundreds of ps level, the relaxivity is <10 mM$^{-1}$ s$^{-1}$ no matter how the other parameters are adjusted. On the other hand, for the contrast agents with $\tau_R$ at 10 ns level, such as the CD2 derivatives in our study, the relaxivity can reach a much higher level by adjusting other parameters such as the $\tau_m$.

Toxicity of Contrast Agent Gd-CA1.CD2

The protein contrast agent Gd-CA1.CD2 did not exhibit acute toxicity at the MRI imaging dose (~2.4 mole/kg), as demonstrated by the fact that all MR imaged mice that received the contrast agent (>10) behaved normally and remained healthy (sacrificed five days after agent injection). The effects of Gd-CA1.CD2 on liver enzymes (ALT, ALP, AST), serum urea nitrogen, bilirubin, and total protein from CD-1 mice 48 hours post-contrast injection were negligible compared to the control mice (Table 3). In addition, no cytotoxicity was observed in tested cell lines, SW620, SW480 and HEK293 that were treated with 50 μM Gd-CA1.CD2, by MTT assay (FIG. 1.7B). Based on the preliminary characterization of toxicity, we conclude that the protein contrast agent is relatively safe.

REFERENCES FOR EXAMPLE 1, EACH OF WHICH ARE INCORPORATED HEREIN BY REFERENCE

1. Tyszka, J. M.; Fraser, S. E.; Jacobs, R. E., *Curr Opin Biotechnol* 2005, 16, (1), 93-99.
2. Lippard, S. J., *Nat Chem Biol* 2006, 2, (10), 504-507.
3. Louie, A. Y.; Huber, M. M.; Ahrens, E. T.; Rothbacher, U.; Moats, R.; Jacobs, R. E.; Fraser, S. E.; Meade, T. J., *Nat Biotechnol* 2000, 18, (3), 321-325.
4. Frangioni, J. V., *Nat Biotechnol* 2006, 24, (8), 909-913.
5. Woods, M.; Woessner, D. E.; Sherry, A. D., *Chem Soc Rev* 2006, 35, (6), 500-511.
6. Lauffer, R. B., *Chem. Rev.* 1987, 87, 901-927.
7. Aime, S.; Barge, A.; Cabella, C.; Crich, S. G.; Gianolio, E., *Curr Pharm Biotechnol* 2004, 5, (6), 509-518.
8. Toth, E.; Helm, L.; Merbach, A. E., *Contrast Agents I: Magnetic Resonance Imaging* W. Krause, Ed. 2002, 221, 61-102.
9. Merbach, A. E.; Toth, E., *The chemistry of contrast agent agents in medical magnetic resonance Imaging.* 2001.
10. Geraldes, C. F.; Sherry, A. D.; Cacheris, W. P.; Kuan, K. T.; Brown, R. D., 3rd; Koenig, S. H.; Spiller, M., *Magn Reson Med* 1988, 8, (2), 191-199.
11. Caravan, P., *Chem Soc Rev* 2006, 35, (6), 512-523.
12. Weinmann, H. J.; Press, W. R.; Gries, H., *Invest Radiol* 1990, 25 Suppl 1, S49-50.
13. Opsahl, L. R.; Uzgiris, E. E.; Vera, D. R., *Acad Radiol* 1995, 2, (9), 762-767.
14. Langereis, S.; de Lussanet, Q. G.; van Genderen, M. H.; Meijer, E. W.; Beets-Tan, R. G.; Griffioen, A. W.; van Engelshoven, J. M.; Backes, W. H., *NMR Biomed* 2006, 19, (1), 133-141.
15. Bryant, L. H., Jr.; Brechbiel, M. W.; Wu, C.; Bulte, J. W.; Herynek, V.; Frank, J. A., *J Magn Reson Imaging* 1999, 9, (2), 348-352.
16. Sirlin, C. B.; Vera, D. R.; Corbeil, J. A.; Caballero, M. B.; Buxton, R. B.; Mattrey, R. F., *Acad Radiol* 2004, 11, (12), 1361-1369.
17. Lanza, G. M.; Winter, P.; Caruthers, S.; Schmeider, A.; Crowder, K.; Morawski, A.; Zhang, H.; Scott, M. J.; Wickline, S. A., *Curr Pharm Biotechnol* 2004, 5, (6), 495-507.

18. Karfeld, L. S.; Bull, S. R.; Davis, N. E.; Meade, T. J.; Barron, A. E., *Bioconjug Chem* 2007, 18, (6), 1697-1700.
19. Gillies, R. J., *J Cell Biochem* Suppl 2002, 39, 231-238.
20. Artemov, D.; Bhujwalla, Z. M.; Bulte, J. W., *Curr Pharm Biotechnol* 2004, 5, (6), 485-494.
21. Aime, S.; Cabella, C.; Colombatto, S.; Geninatti Crich, S.; Gianolio, E.; Maggioni, F., *J Magn Reson Imaging* 2002, 16, (4), 394-406.
22. Anderson, E. A.; Isaacman, S.; Peabody, D. S.; Wang, E. Y.; Canary, J. W.; Kirshenbaum, K., *Nano Lett* 2006, 6, (6), 1160-1164.
23. Strijkers, G. J.; Mulder, W. J.; van Heeswijk, R. B.; Frederik, P. M.; Bomans, P.; Magusin, P. C.; Nicolay, K., *MAGMA* 2005, 18, (4), 186-192.
24. Caravan, P.; Greenwood, J. M.; Welch, J. T.; Franklin, S. J., *Chem Commun (Camb)* 2003, (20), 2574-2575.
25. Kim, Y.; Welch, J. T.; Lindstrom, K. M.; Franklin, S. J., *J Biol Inorg Chem* 2001, 6, (2), 173-181.
26. Sudnick, D. R.; Horrocks, W. D., Jr., *Biochim Biophys Acta* 1979, 578, (1), 135-144.
27. Beeby, A.; Clarkson, I. M.; Dickins, R. S.; Faulkner, S.; Parker, D.; Royle, L.; de Sousa, A. S.; Gareth Williams, J. A.; Woods, M., *J Chem. Soc., Perkin Trans.* 1999, 2, 493-504.
28. Martell, A. E.; Simth, R. M.; Motekaitis, R. J., *NIST Standard Reference Data, Gaithersburg, Md.* 1993.
29. Wilkins, A. L.; Yang, W.; Yang, J. J., *Curr Protein Pept Sci* 2003, 4, (5), 367-373.
30. Yang, W.; Wilkins, A. L.; Li, S.; Ye, Y.; Yang, J. J., *Biochemistry* 2005, 44, (23), 8267-8273.
31. Yang, W.; Wilkins, A. L.; Ye, Y.; Liu, Z. R.; Li, S. Y.; Urbauer, J. L.; Hellinga, H. W.; Kearney, A.; van der Merwe, P. A.; Yang, J. J., *J Am Chem Soc* 2005, 127, (7), 2085-2093.
32. Deng, H.; Chen, G.; Yang, W.; Yang, J. J., *Proteins* 2006, 64, (1), 34-42.
33. Yang, W.; Lee, H. W.; Hellinga, H.; Yang, J. J., *Proteins* 2002, 47, (3), 344-356.
34. Pidcock, E.; Moore, G. R., *J Biol Inorg Chem* 2001, 6, (5-6), 479-489.
35. Yang, W.; Jones, L. M.; Isley, L.; Ye, Y.; Lee, H. W.; Wilkins, A.; Liu, Z. R.; Hellinga, H. W.; Malchow, R.; Ghazi, M.; Yang, J. J., *J Am Chem Soc* 2003, 125, (20), 6165-6171.
36. Maniccia, A. W.; Yang, W.; Li, S. Y.; Johnson, J. A.; Yang, J. J., *Biochemistry* 2006, 45, (18), 5848-5856.
37. Ye, Y.; Lee, H. W.; Yang, W.; Shealy, S. J.; Wilkins, A. L.; Liu, Z. R.; Torshin, I.; Harrison, R.; Wohlhueter, R.; Yang, J. J., *Protein Eng* 2001, 14, (12), 1001-1013.
38. Ye, Y.; Lee, H. W.; Yang, W.; Shealy, S.; Yang, J. J., *J Am Chem Soc* 2005, 127, (11), 3743-3750.
39. Wedeking, P.; Shukla, R.; Kouch, Y. T.; Nunn, A. D.; Tweedle, M. F., *Magn Reson Imaging* 1999, 17, (4), 569-575.
40. Kumar K.; Tweedle, M. F.; Malley, M. F.; Cougoutas, J. Z., *Inorg. Chem.* 1995, 34, 6472-6480.
41. Cacheris, W. P.; Quay, S. C.; Rocklage, S. M., *Magn Reson Imaging* 1990, 8, (4), 467-481.
42. Bulte, J. W.; Kraitchman, D. L., *NMR Biomed* 2004, 17, (7), 484-499.
43. Wyss, D. F.; Dayie, K. T.; Wagner, G., *Protein Sci* 1997, 6, (3), 534-542.
44. Rao, S. T.; Satyshur, K. A.; Greaser, M. L.; Sundaralingam, M., *Acta Crystallogr D Biol Crystallogr* 1996, 52, (Pt 5), 916-922.
45. Barnhart, J. L.; Kuhnert, N.; Bakan, D. A.; Berk, R. N., *Magn Reson Imaging* 1987, 5, (3), 221-231.
46. van Zijl, P. C.; Jones, C. K.; Ren, J.; Malloy, C. R.; Sherry, A. D., *Proc Natl Acad Sci USA* 2007, 104, (11), 4359-4364.
47. Lauffer, R. B.; Parmelee, D. J.; Ouellet, H. S.; Dolan, R. P.; Sajiki, H.; Scott, D. M.; Bernard, P. J.; Buchanan, E. M.; Ong, K. Y.; Tyeklar, Z.; Midelfort, K. S.; McMurry, T. J.; Walovitch, R. C., *Acad Radiol* 1996, 3 Suppl 2, S356-358.
48. Lauffer, R. B.; Parmelee, D. J.; Dunham, S. U.; Ouellet, H. S.; Dolan, R. P.; Witte, S.; McMurry, T. J.; Walovitch, R. C., *Radiology* 1998, 207, (2), 529-538.
49. Parmelee, D. J.; Walovitch, R. C.; Ouellet, H. S.; Lauffer, R. B., *Invest Radiol* 1997, 32, (12), 741-747.
50. Allen, M. J.; Meade, T. J., *J Biol Inorg Chem* 2003, 8, (7), 746-750.
51. Brasch, R.; Turetschek, K., *Eur J Radiol* 2000, 34, (3), 148-155.
52. Toth, E.; Helm, L.; Merbach, A. E. *Contrast Agents I: Magnetic Resonance Imaging* W. Krause, Ed. 2002, 221, 61-102.

Example 2

PEGylation Modification of Protein MRI Contrast Agents with Enhanced Relaxivity and Reduced Immunogenicity Introduction:

In this Example, we report our progress in optimizing designed protein contrast agents for in vivo imaging by pegylation. Our experimental results clearly demonstrate that PEGylation substantially increases the solubility of protein by more than 100 fold without reducing metal binding affinity and selectivity. In addition, the serum stability is significantly improved. Interestingly, PEGylation further increased the in vitro R1 and R2 relaxivities of the developed protein contrast agents by 2-3 fold, which is in contrast to the loss of functionality of protein drug by pegylation. Such increased relaxivity is a result of the addition of a hydration layer due to water retention by Poly-PEG chain on the protein surface and alteration of correlation time. The agent demonstrated a strong contrast enhancement in the animal imaging with a dose 70 fold lower than that of Gd-DTPA. Our developed contrast agent showed a much longer blood circulation time, and the blood circulation time and its distribution of our protein contrast agent in mice can be modified by using different lengths of PEG. Furthermore, the immunogenicity of the contrast agent has been significantly decreased by pegylation. The optimized properties of protein contrast agents by pegylation facilitate the disease targeted tissue and molecular imaging.

PEGylation of protein is a method used to improve the pharmacokinetics and pharmaco-dynamics of various protein and peptide drugs. PEGylation involves modifications of Lys, Glu, Asp, or Cys residues of a protein or peptide with various sizes of polyethylene glycerol chain. The result of PEGylation modifications is the attachment of the different size of polyethylene glycerol chains on the surface of the modified protein or peptide. The protein or peptide experiences several property changes, especially in pharmacokinetics and pharmaco-dynamics. Two changes are obvious: (1) the increase in molecular size, especially in the case of small peptide, and (2) the reduction in surface charges of protein and peptide. A consequence of these two changes is the increase in blood circulation time and delay in the renal secretion. Another effect of the changes is the reduced immunogenicity of the protein or peptide drugs after PEGylation. The strategy has been successfully employed in a number of protein or peptide drugs for increased efficacy and/or reduced immuno-response of the drug. Since the polyethylene glycerol chains are strongly hydrophilic, PEGylation of protein will also result in a dramatic increase in solubility of protein or peptide drugs. However, the most significant drawback of PEGylation for a protein or peptide drug is that the bulk volume of the polyethylene glycerol chains on the surface of proteins often blocks the bio-active site(s) leading to significant decrease in bio-activity.

We have previously reported the development of protein-based MRI contrast agents by rational design of $Gd^{3+}$ binding sites into a stable protein using amino acids residues as metal coordinating ligands. The designed protein contrast agent exhibits a 10-20-fold increase in in vitro R1 and R2 relaxivities compared to the current clinically used contrast agent Gd-DTPA. To apply this class of novel class of protein contrast agents to in vivo imaging, several additional factors must be considered. First, contrast agents need to have high solubility. Because of limitations in the sensitivity of MRI techniques and injection volumes for animals, in order to provide significant in vivo tissue contrast, requires up to a 300-500 mM injection dose for a clinically used DTPA with a relaxivity of 5 $mM^{-1} s^{-1}$. Compared to DTPA, our protein contrast agents with a 10-20 fold increase of relaxivity require a soluble concentration of 30-50 mM. Second, proper blood circulation time is required to facilitate targeted tissue or molecular MR imaging. Third, the in vivo stability of the contrast agents against degradation and kinetic stability against metal transformation is essential to reduce toxicity. Fifth, the immunogenicity of the protein contrast agents needs to be reduced.

In this Example, we report our progress in optimizing designed protein contrast agents for in vivo imaging by pegylation. Our experimental results clearly demonstrate that PEGylation substantially increases the solubility of protein by more than 100 fold without reducing metal binding affinity and selectivity. In addition, the serum stability is significantly improved. Interestingly, PEGylation further increased the in vitro R1 and R2 relaxivities of the developed protein contrast agents by 2-3 fold, which is contrast to the loss of functionality of protein drug by pegylation. The agent demonstrated a strong contrast enhancement in the animal imaging with a dose 70 fold lower than that of Gd-DTPA. Our developed contrast agent showed a much longer blood circulation time, and the blood circulation time and its distribution of our protein contrast agent in mice can be modified by using different lengths of PEG. Furthermore, the immunogenicity of the contrast agent has been significantly decreased by pegylation. The optimized properties of protein contrast agents by pegylation facilitate the disease targeted tissue and molecular imaging.

2. Material and Methods

All pegylation reagents were purchased. Metal and dye reagents were purchased from Molecular Probes and Sigma. Cys was added at the C-terminal of the CA1.CD2 and subcloned in pet20b for protein expression. Site-directed mutagenesis method was used to remove Lys at different locations. DNA sequences were verified by DNA sequence core facility.

2.1 Protein Expression and Purification

Protein was expressed in *E. coli* as inclusion body and purified using urea refolding and ion-exchange column. N15 labeled protein was expressed in SV medium as GST fusion (Yang et al., Biochem 2006) and purification was by GST-4B affinity column and SP column. Protein was verifed by mass spectrometry. Protein concentration was calculated using extinction coefficient of w.t. CD2 of 11,000 (Ye et al., 2001). Protein solubility was determined by concentrating proteins to reach to precipitation using speed vac.

2.2 Pegylation

We first carried out the PEGylation modifications of Lys residues on our designed protein MRI contrast agents using different preactivated NHS with PEG units of 4, 12, 40, 12K, and 20 K (FIGS. 2.2-2.4). Typically reactions were carried out using 3:1 or 5:1 PEG: protein at room temperature for 1-2 hours. Reactions at pH 6, 7 and 9 were also performed with no maj or change in the pegylation results. N-terminal pegylation of Lys was performed at pH 6 according to published papers (1-5). All reactions were quenched by adding free amino acids and stored at −20° C. for further purification. Specifically modification at the Cys at the C-terminal was performed by using published methods (1-5).

Separation of pegylated proteins were achieved by 10 fold dilution of reaction mix and loaded on sp column using a pH gradient from 2 to 7. Free PEG was not able to bind to the column and washed away before pH gradient. Free unpegylated protein fractions were eluted out at the latest fraction at high pH. Separated protein samples were then verified by mass spectrometry analysis, metal binding and NMR.

2.3 Mass Spectrometry

ESI and MALDI spectrometry were used to identify the number of pegylation sites and metal binding stoichiometry. The pegylation sites were identified using trypsin cleavage followed by Mass analysis using TOF/TOF.

2.4 $Gd^{3+}$-Binding Affinity Determination.

$Gd^{3+}$-binding affinities of CA1.CD2 and its pegylated variants were determined by a competition titration with Fluo-5N applied as a $Gd^{3+}$ indicator (Yang et al., JACS, 2008). The fluorescence spectra of Fluo-5N were obtained with a fluorescence spectrophotometer (Photon Technology International, Inc.) with a 10 mm path length quartz cell at 22° C. Fluo-5N emission spectra were acquired at 500 nm to 650 nm with an excitation at 488 nm. $Gd^{3+}$-binding affinity of Fluo-5N, $K_{d1}$, was first determined by a $Gd^{3+}$ titration with $Gd^{3+}$ buffer system of 1 mM nitrilotriacetic acid (NTA). Free $Gd^{3+}$ concentration was calculated with a NTA $Gd^{3+}$-binding affinity of $2.6\times10^{-12}$ M.[28] Fluo-5N was mixed with $Gd^{3+}$ in 1:1 ratio for a competition titration. The experiment was performed with a gradual addition of CA1.CD2 or its variants. An apparent constant, $K_{app}$, was estimated by fitting the fluorescence emission intensity of Fluo-5N at 520 nm with different CA1.CD2 concentrations as a 1 to 1 binding model. $Gd^{3+}$-binding affinity of CA1.CD2, $K_{d2}$, was calculated with the following equation:

$$K_{d2} = K_{app} \frac{K_{d1}}{K_{d1} + [Fluo-5N]_T} \quad (1)$$

Metal binding affinity for $Ca^{2+}$ and $Zn^{2+}$ were determined using similar competition methods and specific dyes with proper Kd values.

2.5 Measurement of Water Coordination Number by Terbium Life Time Luminescence.

The numbers of water ligands coordinated to $Gd^{3+}$-CA1.CD2 and variants complex were determined by measuring $Tb^{3+}$ luminescence decay in $H_2O$ or $D_2O$ (Yang et al., 2008). $Tb^{3+}$ excited state lifetime was measured using a fluorescence spectrophotometer (Photon Technology International, Inc.) with a 10 mm path length quartz cell at 22° C. Following excitation at 265 nm with a XenoFlash (Photon Technology International, Inc.), $Tb^{3+}$ emission was monitored at 545 nm in a time series experiment in both H$_2$O and D$_2$O systems. Luminescence decay lifetime was obtained by fitting the acquired data with a mono-exponential decay function. H$_2$O in CA1.CD2 solution was replaced with D$_2$O by lypholization and re-dissolved in D$_2$O at least three times. A standard curve correlating the $\Delta k_{obs}$ with water number under our experimental conditions was established by using well-characterized chelators, such as EDTA (q=3), DTPA (q=1), NTA (q=5), and Aquo Tb$^{3+}$ (q=9) solution with R$^2$=0.997.[26, 27] Water number coordinated to Tb$^{3+}$-CA1.CD2 complex was then obtained by fitting the acquired $\Delta k_{obs}$ value to the standard curve.

2.6 In Vitro MRI Relaxivity

Relaxivity was determined using 0.47 T (20 Hz) minispec Magnetic Relaxometer (Bruker) and 300 and 500 MHz NMR (Varian).

2.7 NMR

Pulse field diffusion NMR was applied to measure the hydrodynamic radii of the protein (Lee et al., BBA 2003) with Protein samples CA1.CD2 and its variants of 0.2 mM in buffer. Lysozme and diaxone were used as an external and internal reference for calibration. The correlation size of the protein was measured using TauC pulse sequence developed by the Prestegard lab at UGA using $^{15}$N labeled protein.

2.8 In Vivo Mouse MR Imaging.

Care of experimental animals was in accordance with institutional guidelines. CD-1 mice (25-30 g, four mice were imaged) were anesthetized with an isoflurane gas mixture. The anesthetized animal was positioned and stabilized with soft-supporting material (e.g. foam) in the scanner in the coil cradle and was kept warm during the MRI scan. The mice were scanned prior to the administration of any contrast agent (pre-contrast). Approximately 50 µl of Gd-CA1.CD2 (~1.2 mM) or Gd-DTPA (~300 mM) were injected into the animal via the tail vein. MR images were collected at different times (indicated). For T$_1$ weighted imaging at 3T, spin echo sequence with TE/TR=15 ms/500 ms was employed. Rectangular Field of View (FOV) at 100/40 mm, an acquisition matrix of 196$^2$ and 1.1 mm slice thickness without gap were used. Images were collected from both transverse and coronal sections. The in-plane resolution of images was less than 0.5 mm after they were reconstructed to the matrix of 196$^2$. For T$_2$ weighted imaging at 9.4T, MR images were recorded using a multi-echo Carr-Purcell-Meiboom-Gill (CPMG) sequence. The data were collected and processed by Dicomworks software. The MR signal intensity in several organs was ascertained by the average intensity in ROIs or points within the organs. Signal intensity for each organ was normalized to that of the leg muscle.

2.9 Blood Circulation Time, Tissue Retention Time, and Bio-Distribution.

CD-1 mice (25-30 g) were anesthetized with isoflurane. Appropriate dosages of Gd-CA1.CD2 and its PEgylated variants (with Gd and $^{153}$Gd) or Gd-DTPA were i.v. injected (via tail vein). Blood (~50 µl) samples were collected via orbital sinus of the mouse at different time points. The mouse was euthanized at the final time point. Tissue samples from kidney, liver, heart, and lung were collected. Serum samples were prepared from the collected blood. For the bio-distribution analyses, the animals were euthanized at single time point (indicated) after i.v. administration of the contrast agent (indicated). The organ/tissue samples were collected. Tissue extracts were freshly made from collected samples using commercially available tissue extracting kits (Qiagen). CA1.CD2 and its variants were detected and quantified by immunoblotting and Sandwich-ELISA using a monoclonal antibody (OX45, detecting antibody) and a home made polyclonal antibody (PabCD2, capture antibody). A series of known amounts of CA1.CD2 samples mixed with blank mouse serum or tissue extracts were used as standard in Sandwich-ELISA. ELISA signal from HRP was monitored using a Fluorstar fluorescence microplate reader. For quantification of Gd$^{3+}$ in the serum and tissue samples one hour (or indicated times) after the contrast agent administration, animals were sacrificed and critical organs were collected, and the tissues were then digested with concentrated nitric acid at 120-130° C. with proper amount of $^{153}$Gd spike as an internal marker. The digested solution was analyzed.

2.10 Immunogenicity

Rabbits were i.p. injected with Gd-CA1.CD2 and its pegylated variants. The agents (CA1.CD2) were mixed with adjuvant or with buffer saline and injected at a dose of 3.0 nmole/kg according to the standard protocol for the antibody production. The rabbits were subjected to double immunolizations in four weeks interval. Blood samples were taken from the immunolized rabbits 3 weeks after each injection. Production of antibodies against the protein contrast agent in each rabbit was examined by ELISA 2.11 Toxicity Analyses.

The MR imaged CD-1 mice that received the i.v. administered Gd-CA1.CD2 and its variants (at a dose of ~2.4 µmol/kg) spiked with $^{157}$Gd$^{3+}$ were returned to their cages (one mouse per cage). The mice were observed for five days and were euthanized at the end of the fifth day. Tissue samples from kidney, liver, spleen, and lung were collected. Gd$^{3+}$ contents in the tissue samples were analyzed by radioactivity counter.

Two groups of mice were used to examine potential renal and/or liver damage by Gd-CA1.CD2. One group of mice received (i.v. tail veil) 50 µl of saline-buffer (as control). Another group received (i.v. tail veil) Gd-CA1.CD2 and variants at 4 µmole/kg. The mice were observed for 48 hours and were euthanized. Blood samples were collected from the experimental mice. Serum samples were prepared from the collected blood.

Liver enzymes in serum samples, including Alanine transaminase (ALT), Alkaline phosphatase (ALP), Aspartate transaminase (AST), Gamma glutamyl transpeptidase (GGT), and bilirubin and urea nitrogen were analyzed by a commercially available source (MU Research Animal Diagnostic Laboratory). All clinical chemistry parameters were measured on an Olympus AU 400 analyzer.

Cytotoxicity was analyzed by MTT assay of the cells that were treated with Gd-CA1.CD2 and its variants at appropriate doses (indicated in figure). The cells were grown under normal growth medium in 96 well plates. Gd-CA1.CD2 or saline-phosphate buffer was added to the cell culture medium. The cells were incubated for appropriate times. A standard MTT assay was employed to assess the cell growth status of the treated cells.

2.12 Serum Stability.

CA1.CD2 (40 µM) in complex with Gd$^{3+}$ was incubated with 75% human serum over 3 or 6 hours at 37° C. The degradation of the protein (disappearance of 12 kDa protein band) was analyzed by SDS-PAGE and visualized by coomassie blue staining for protein and idiol staining for PEG moiety. In parallel, the degradation of the protein was also analyzed by immunoblot using antibodies OX54 or PabCD2. The identities of CA1.CD2 and pegylated variants were verified by immunoblotting using antibody PabCD2. and idiol staining.

3. Results
3.1 PEGylation Modifications of Designed Protein Contrast Agent CA1.CD2

We previously reported the development of a novel class of protein-based MRI contrast agents. The contrast agents exhibit a 20 fold increase in R1 and R2 relaxivities and provide a strong contrast enhancement in the mouse MR imaging (Yang, et. al. JACS 2008). The developed MRI contrast agent also demonstrated a prolonged blood circulation time, which is considered for the application of the agents in disease targeted molecular imaging. In the processes of preparing the protein contrast agent for animal MR imaging, we realized that it is desirable to have a higher protein concentration up to 30-50 mM based on the in vivo application dose of DTPA (300-500 mM) per 100 ul injection. However, the solubility of the current formulation of our protein contrast CA1.CD2 is ~0.7 mM.

As shown in FIG. 2.1, the designed contrast agent CA1.CD2 has eight Lys residues with different solvent accessibility and six Lys residues are well exposed. Based on the considerations of solubility, circulation, relaxivity and serum stability, we therefore carried out PEGylation of our protein contrast agents by modifying surface Lys residues and site specific pegylation. First, preactivated PEG units with varied chain length and branches of 4, 12 (Poly-PEG12), 40 (PolyPEG40k), 5K, and 12 K (see FIG. 2.1b) were used to modify surface lys residues. Site-specific pegylation was performed at both N-terminal Lys and C-terminal Cys.

To identify optimal conditions for pegylation, PeG reactions were performed at different reaction time, pH 6, 7 and 9, and reaction ratio. FIGS. 2.2-2.4 shows the SDS gel of the protein contrast agent CA1.CD2 pegylated with PEGylation kits with different reaction moieties stained by both commassie blue for protein and idiol for the PEG moiety.

FIG. 2.2 shows that the PEGylated proteins were separated using ion exchange column, size exchange column, and a Cis reverse phase HPLC chromatography column.

The modified proteins were purified by HPLC to relative homogeneity. FIG. 2.2 shows that there were several major peaks of the PEGylated proteins on the FPLC chromatography. MALD-Mass analyses of the separated protein fraction reveal that at pH 7.4 with 5:1 pEG:protein:preactivated pEG reagents, CA1.CD2 was pegylated mainly with 2, 3 with P4-P40 and 1 PEG unit with PEG 12 K to 20K.

3.2 Determination of PeGylation Numbers

With the addition of N-terminal $NH_2$ groups, the CA1.CD2 has total of seven potential PEGylation sites. The PEGylation sites of the purified protein were examined first by trypsin cleavage to generate the peptides/fragments and then sequenced by TOF/TOF MS. Usually 2-4 PEG units were attached to each protein depending on the ratio of PEG:protein under reaction and the reaction conditions.

3.3 Conformation and Metal Binding Capabilities

FIG. 2.4a of Trp fluorescence spectra shows that these PEGylated proteins (CA1.CD2-PEG12 and CA1.CD2-PEG40) maintain the native structure of the protein contrast agents with unchanged Trp emission maximum compared with CA1.CD2.

All of the designed $Gd^{3+}$ binding proteins were expressed in *E. coli* and subsequently purified by procedures previously published from our laboratory.[30, 31] All of the designed proteins form the expected metal:protein complex as demonstrated by ESI-Mass spectrometry.

Tb-FRET was first used to monitor the effect of pegylation on the metal binding capabilities. As shown in FIG. 2.4b, the pegylated A1.CD2 is able to have Tb-sensitized energy transfer similar to that of CA1.CD2. FIG. 2.5 shows that PEGylated CA1.CD2-P40 remains intact after incubate with human serum for 24 hours at 37° C. monitored by SDS Page.

$Gd^{3+}$-binding affinity of CA1.CD2 was further determined by a competition titration with fluorescent dye applied as a $Gd^{3+}$ indicator in various chelate-metal buffer systems. The PEGylated variants exhibit similar metal binding affinities to unpegylated ones for $Ca^{2+}$, $Gd^{3+}$ and $Zn^{2+}$.

3.4 the Effect of PEGylation on the Relaxivities of the Protein Contrast Agent

We first measured the in vitro relaxivities of the PEGylated protein contrast agent in MRI scanner such as at 0.47, 3.0, and 9.4T field strengths (FIG. 2.6). Very similar procedure used in our previous studies in measuring the relaxivities of protein MRI contrast agent {Yang, et. al., JACS 2008} was employed here to measure the relaxivities of PEGylated CA1.CD2. It was clear that the relaxivities (both R1 and R2) were increased compared to those of the same protein contrast agent before PEGylation modification. In addition, the MRI relaxivity increases with the increase of PEG length as shown in FIG. 2.6.

Increasing the degree of PEGylation modification increased the R1 and R2 relaxivities (FIG. 2.6). The R1 and R2 relaxivities of the PEGylated protein were also affected by the size of the PEG chains. The relaxivities of the PEGylated protein contrast agents demonstrated higher increases when the protein was modified by a longer PEG chain. Interestingly, both R1 and R2 relaxivities of the PEGylated protein contrast agent experienced the most dramatic increases at higher magnetic field. This is contrary to the case of unPEGylated protein, in which dramatic decreases in R1 and R2 relaxivities were observed at high field (Yang et al., JACS, 2008). FIG. 2.6 shows the MRI relaxivity as a function of chain dependencies. Specific modification of the N-terminal amine and Cys residues at the C-terminus have a similar effect on the relaxivity of the protein.

Table 2.1 of Example 2 shows that the water numbers in the coordination shell of CA1.CD2 increased from 2 to 3 upon PEGylation with PEG40. This may contribute to the increased relaxivity by PEGylation.

3.6 PEGylation Improved Blood Circulation Time

PEGylation has been demonstrated to increase blood circulation time and reduce immunogenicity of a number of protein drugs. While longer blood circulation time is a desired property for the applications of MRI contrast agents. Elimination or reduction of immunogenicity is essential for clinical applications of the protein MRI contrast agents. We therefore examined whether PEGylation of CA1.CD2 changed the bio-distribution and immunogenicity properties of the agent. The PEGylated or unPEGylated CA1.CD2 was introduced to CD-1 mice via i.v. tail vein injection. Distributions of the administered agent among different organs/tissues and blood circulation were analyzed at different time intervals by quantization of both the protein CA1.CD2 using immunochemical assays and the metal $Gd^{3+}$ using γ-radiation counting the radio-isotope $^{157}Gd^{3+}$. It was clear from analyses of both protein CA1.CD2 and $Gd^{3+}$ in multiple organ sites and blood that the PEGylation changed the bio-distribution of the protein contrast agent. First, PEGylation increased the blood circulation time of the agent. Before PEGylation modifications, a sharp decrease in blood concentration of both $Gd^{3+}$ and CA1.CD2 was observed at about 50 minutes post i.v. injection. In contrast, no significant decrease was observed with PEGylated proteins 6 hour post injection. The longer circulation time was observed with the protein with higher degree of PEGylation modifications. Serum stability was further examined by measuring the protein content incubating with serum. Gegylated proteins remain stable after 48 hours.

3.7 PEGylation Reduced Immunogenicity

Immunogenicity is one of the main concerns on the application of our developed protein MRI contrast agent. We therefore carried out experiments to test immunogenicity in rabbits by i.p. injection. The agents (CA1.CD2) were mixed with adjuvant or with buffer saline and injected at a dose of 3.0 nmole/kg according to the standard protocol for antibody production. The rabbits were subjected to double immunolizations in four weeks interval. Blood samples were taken from the immunolized rabbits 3 weeks after each injection. Production of antibodies against the protein contrast agent in each rabbit was examined by ELISA (FIG. 2.7 Left) and immunoblotting (FIG. 2.7 Right) using our previous polyclonal antibody PabCD2 as positive control and the pre-bleed from each rabbit as negative controls. It was clear that without adjuvant, injection of CA1.CD2 alone did not lead to antibody production in rabbits even after a double dose immunization. Addition of adjuvant indeed resulted in immuno-responses. PEGylation modifications of protein dramatically reduced immuno-responses. There was almost no antibody production in the first immunization. The production of antibody was negligible three weeks after the second immunization. Our results suggest that the immunogenicity of the protein contrast agent may not be very strong, especially without addition of adjuvant. Modification of the protein by PEGylation substantially reduced the immune responses.

FIG. 2.7 shows that PEGylation with P40 completely eliminates the binding of CA1.CD2 by antibody OX55 and decreases by 50% binding of OX34 in Western Blot. Since the epitope binding sites of OX55 and OX34 are well known, we have shown that K66, K45, K44, and K47 exhibit a high probability for the specific PEGylation by PEG12. These results confirm that antibody recognition sites can be eliminated by PEGylation, which is essential for the reduction of immunogenicity.

REFERENCES FOR EXAMPLE 2, EACH OF WHICH IS INCORPORATED HEREIN BY REFERENCE

1. Gaberc-Porekar V, Zore I, Podobnik B, Menart V. Obstacles and pitfalls in the PEGylation of therapeutic proteins. Curr Opin Drug Discov Devel. 2008 March; 11(2):242-50.
2. Fishburn C S. The pharmacology of PEGylation: Balancing PD with PK to generate novel therapeutics. J Pharm Sci. 2008 Jan. 15;
3. Veronese F M, Pasut G. PEGylation, successful approach to drug delivery. Drug Discov Today. 2005 Nov. 1; 10(21):1451-8. Review.
4. Harris J M, Chess R B. Effect of pegylation on pharmaceuticals. Nat Rev Drug Discov. 2003 March; 2(3):214-21. Review.

5 Yang, W., Wilkins, A. L., Li, S., Ye, Y., and Yang, J. J. (2005) The effects of Ca2+ binding on the dynamic properties of a designed Ca2+-binding protein. *Biochemistry* 44, 8267-73.

6 Adair, F., and Ozanne, D. (2002) The immunogenicity of therapeutic proteins. *Biopharm-the Applied Technologies of Biopharmaceutical Development* 15, 30-+.

7 Leyland-Jones, B., Arnold, A., Gelmon, K., Verma, S., Ayoub, J. P., Seidman, A., Dias, R., Howell, J., and Rakhit, A. (2001) Pharmacologic insights into the future of trastuzumab. *Ann Oncol* 12 *Suppl* 1, S43-7.

8 Hermeling, S., Crommelin, D. J., Schellekens, H., and Jiskoot, W. (2004) Structure-immunogenicity relationships of therapeutic proteins. *Pharm Res* 21, 897-903.

9 Lucas, A., and McFadden, G. (2004) Secreted immunomodulatory viral proteins as novel biotherapeutics. *J Immunol* 173, 4765-74.

10 Schellekens, H. (2002) Immunogenicity of therapeutic proteins: clinical implications and future prospects. *Clin Ther* 24, 1720-40; discussion 1719.

10 Schellekens, H. (2002) Bioequivalence and the immunogenicity of biopharmaceuticals. *Nat Rev Drug Discov* 1, 457-62.

11 Federico, R., Cona, A., Caliceti, P., and Veronese, F. M. (2006) Histaminase PEGylation: Preparation and characterization of a new bioconjugate for therapeutic application. *J Control Release* 115, 168-174.

12 Veronese, F. M., and Pasut, G. (2005) PEGylation, successful approach to drug delivery. *Drug Discov Today* 10, 1451-8.

13 Bhadra, D., Bhadra, S., Jain, P., and Jain, N. K. (2002) Pegnology: a review of PEG-ylated systems. *Pharmazie* 57, 5-29.

14 Bailon, P., Palleroni, A., Schaffer, C. A., Spence, C. L., Fung, W. J., Porter, J. E., Ehrlich, G. K., Pan, W., Xu, Z. X., Modi, M. W., Farid, A., Berthold, W., and Graves, M. (2001) Rational design of a potent, long-lasting form of interferon: a 40 kDa branched polyethylene glycol-conjugated interferon alpha-2a for the treatment of hepatitis C. *Bioconjug Chem* 12, 195-202.

15 Basu, A., Yang, K., Wang, M., Liu, S., Chintala, R., Palm, T., Zhao, H., Peng, P., Wu, D., Zhang, Z., Hua, J., Hsieh, M. C., Zhou, J., Petti, G., Li, X., Janjua, A., Mendez, M., Liu, J., Longley, C., Zhang, Z., Mehlig, M., Borowski, V., Viswanathan, M., and Filpula, D. (2006) Structure-function engineering of interferon-beta-1b for improving stability, solubility, potency, immunogenicity, and pharmacokinetic properties by site-selective mono-PEGylation. *Bioconjug Chem* 17, 618-30.

16 Kozlowski, A., Charles, S. A., and Harris, J. M. (2001) Development of pegylated interferons for the treatment of chronic hepatitis C. *Bio Drugs* 15, 419-29.

17 Kozlowski, A., and Harris, J. M. (2001) Improvements in protein PEGylation: pegylated interferons for treatment of hepatitis C. *J Control Release* 72, 217-24.

18 Yang, Z., Wang, J., Lu, Q., Xu, J., Kobayashi, Y., Takakura, T., Takimoto, A., Yoshioka, T., Lian, C., Chen, C., Zhang, D., Zhang, Y., Li, S., Sun, X., Tan, Y., Yagi, S., Frenkel, E. P., and Hoffman, R. M. (2004) PEGylation confers greatly extended half-life and attenuated immunogenicity to recombinant methioninase in primates. *Cancer Res* 64, 6673-8.

19 Nie, Y., Zhang, X., Wang, X., and Chen, J. (2006) Preparation and stability of N-terminal mono-PEGylated recombinant human endostatin. *Bioconjug Chem* 17, 995-9.

20 Daugherty, A. L., and Mrsny, R. J. (2006) Formulation and delivery issues for monoclonal antibody therapeutics. *Adv Drug Deliv Rev* 58, 686-706.

21 Mohs, A. M., Zong, Y., Guo, J., Parker, D. L., and Lu, Z. R. (2005) PEG-g-poly(GdDTPA-co-L-cystine): effect of PEG chain length on in vivo contrast enhancement in MRI. *Biomacromolecules* 6, 2305-11.

22 Luciani, A., Olivier, J. C., Clement, O., Siauve, N., Brillet, P. Y., Bessoud, B., Gazeau, F., Uchegbu, I. F., Kahn, E., Frija, G., and Cuenod, C. A. (2004) Glucosereceptor MR imaging of tumors: study in mice with PEGylated paramagnetic niosomes. *Radiology* 231, 135-42.23 Yang J J, Yang J, Wei L, Zurkiya O, Yang W, Li S, Zou J, Zhou Y, Maniccia A L, Mao H, Zhao F, Malchow R, Zhao S, Johnson J, Hu X, Krogstad E, Liu Z R. *Rational design of protein-based MRI contrast agents.* J Am Chem Soc, 2008. 130(29): p. 9260-7.

Example 3

Developing Protein-Based MRI Contrast Agents with Multiple Metal-Binding Sites by Engineering of Natural Calcium Binding Proteins Natural calcium binding proteins with continuous calcium binding sites such as calmodulin, calbindin D9K, troponin C, parvalbumin and discontinuous calcium binding sites such as therminase subtilisin have exhibited high metal binding affinity for calcium as shown in Table 3.1 (shown in FIG. 3.10). Most of these calcium binding proteins have multiple calcium binding sites and their protein stabilities against temperature and proteolysis were significantly increased. For example, calcium binding to calmodulin has increased its stability to higher than 100° C. While a great deal of research has shown that the calcium binding affinity of naturally evolved proteins can be reduced by site-directed mutagenesis, methods to increase calcium binding affinity have rarely been reported. In addition, while lanthanide ions were shown to have coordination chemistry properties similar to calcium and often were able to compete with calcium for the metal binding sites, the accurate measurement of lanthanide metal binding affinities was not reported due to the limitation of extremely high metal binding affinity. Traditional titration methods by direct addition of metal ions monitoring lanthanide emission or Tb-sensitized energy transfer only provide low estimation of the metal binding sites. Furthermore, calcium ions in the strong metal binding sites of proteins are often difficult to remove and require careful treatment.

In this study, we report the engineering of protein based contrast agents by modifying calcium binding pockets of natural calcium binding proteins using calmodulin (CBP1) (FIG. 3.1) and parvalbumin (CBPP) as examples. These engineered proteins exhibit strong metal binding affinity to $Gd^{3+}$ and other lanthanide (FIGS. 3.2A-3.2C). Both proteins have strong $Gd^{3+}$ binding affinity dissociation constants ($K_d$, M) of $1.0 \times 10^{-15}$ to $1.0 \times 10^{-18}$ M. In addition, their selectivity over calcium and other metal ions such as zinc and magnesium is more than $10^5$ fold higher, which is similar to that of clinically approved contrast agents such as DTPA or DTPA-BMA. CBPP and its variants exhibit strong metal selectivity for Ln3+ over calcium, magnesium, zinc and copper (FIG. 3.2C). Furthermore, the water numbers in the coordination site can be estimated by Tb-sensitized energy transfer in water and in $D_2O$. These data suggest that more than one water molecules are in the coordination shells and protein surface, and this likely contributes to their extremely high relaxivity. FIG. 3.8 shows that calmodulin and its variants can be pegylated with peg units of 4, 12, 40, 5K, 12K, 20 K and reaction products can be well separated by size-exclusion and ion exchange columns (FIG. 3.3 and FIG. 3.4).

Furthermore, functional sites of these engineered proteins, such as binding to the target molecules by calmodulin and parvalbumin, were eliminated by both deleting the molecular recognition sites and creating submodulin without completed recognition sites. Moreover, pegylation of these engineered proteins further reduced the natural function of CBP with increased solubility and reduced immunogenicity.

The conformation and metal binding properties of PEGylated proteins were not changed as revealed by Tyr emission spectra and $Tb^{3+}$ sensitized energy transfer and CD methods (FIGS. 3.5A-3.5C). FIGS. 3.6A and 3.6B show that both BCBP1 and CBBP1 and their variants have strong serum stability revealed by SDS page. These proteins remain intact upon incubation with serum greater than 48 hours.

These engineered proteins exhibit extremely high $r_1$ and $r_2$ relaxivities that are about 20 fold higher than DTPA. More strikingly, a clear in vivo mice imaging shown in FIG. 3.7 and FIG. 3.9 can be achieved using one dose tail vein injection with 6 mM of engineered protein contrast agent, CBP1 and its pegylated variant CBP1-P40. This dosage is about 70 fold lower than that of DTPA, with relaxivity values at 20-40 $mM^{-1}$ $s^{-1}$ at 0.47 T. These values are comparable to CA1.CD2 and 5-8 fold greater than that of DTPA (FIG. 3.8). Example 3, FIG. 3.9 (left) illustrates mice MRI images at slice 3 (top) and slice 4 (bottom) at 4.7T with tail vein injection of 6 mM CBP1-P40 at 0, and 13 mins post injection. Relative MRI intensity at different organs is shown on right.

Based on the fact that the blood circulation and biodistribution can be further optimized and the existence of ample natural calcium binding proteins with multiple sites and different molecular weights/sizes, in addition to their superior capability for targeting our reported approach opens a new way to engineer MRI contrast agents with significantly improved relaxivity and in vivo properties for both blood pool and molecular imaging.

Example 4

Developing PEGylated Protein Contrast Agents Capable of Target Cancer Tumor Biomarkers Both in Cells and in Mice Embodiment of the PEGyation method of the present disclosure was applied to enhance the performance of developed contrast agents in imaging cancer biomarker.

Example 4 describes a novel protein-based MRI contrast agent for molecular targeting cancer marker HER2 has been developed by modification with pegylation. The MRI contrast agent also carries a near-IR dye Cy5.5 for dual modality imaging of HER2 in cancer (Section 4.1).

In addition, Example 4 describes the development of a contrast agent that demonstrates specific interaction with HER2 positive cancer cells but not HER2 negative cells (4.2). The in vitro MR imaging experiments with different cells that express different levels of HER2 have shown a close correlation between MRI contrast enhancements and HER2 levels (Section 4.3).

Furthermore, Example 4 describes that the MR imaging of xenograft models of human HER2 positive cell line SKOV3 and HER2 negative cell line MDA-MB-231 has indicated a HER2 level-dependent MRI contrast enhancement. This image intensity enhancement is further confirmed by NIR imaging (Section 4.4).

In addition, Example 4 describes immunohistochemical staining of tissue samples (including tumor tissue) collected after imaging analyses has shown that the designed contrast agent penetrated deep into the tumor mass (i.e., distant from tumor vasculature), demonstrating a good tissue penetration of the MRI contrast agent. Differential targeting of the MRI contrast agent to HER2 positive and to HER2 negative tumors was further verified by immunoblot and ELISA analyses of the tissue samples collected from imaging mice (Section 4.5).

4.1 Design of HER2 Targeting MRI Contrast Agent

To apply this MRI contrast agent in targeted molecular MR imaging, we fused a high affinity 58 amino acid HER2 affibody at the C-terminal of the protein via a flexible linker GGSGG. We also introduced a photo-probe by conjugating a near-IR dye Cy5.5 to a Cys residue added to the C-terminal of the protein (FIG. 4.1). The designed dual probe protein was expressed in *E. coli* and subsequently purified by procedures described in our previous report {{Yang, et. al., JACS 2008}, which is incorporated herein by reference}.

PEGylation of the designed Gd-binding protein not only increases protein solubility and blood circulation time, but also decreases immunogenicity of the protein without decrease of MRI relaxivity of the protein contrast agent. Therefore the designed HER2 targeting protein contrast agent was PEGylated using PEG-40, a PEG molecule with triple-branched 12 units PEG. The resulting agent (PEG-CA1-Affi) exhibits very similar $Gd^{3+}$ binding properties and its T1 and T2 relaxivity values are similar to its parent protein CA1.CD2. Modifications did not change the overall protein fold as demonstrated by circular dichroism and fluorescence spectra.

4.2 the HER2 Targeting MRI Contrast Agent Targeted to HER2 Positive Cells but not HER2 Negative Cells We first examined whether the designed CA1.HER2/Affi can target cancer cells by cell binding analyses. We used two cancer cell lines for the binding analyses. AU565 is derived from breast carcinoma. EMT6 is a mouse mammary tumor cell line. AU565 cells express very high levels of HER2. The EMT is regarded as a HER2 negative cell line. Binding of the Gd-CA1.HER2/Affi to the cancer cells was first analyzed by immuno-fluorescence staining using a polyclonal antibody against PEGylated parental protein CA1.CD2 (PAb-PGCA1). A substantial increase in staining intensities of CA1-Affi bound to AU565 cells was observed at both 37 and 4° C. The protein did not bind to EMT6 cells. As a control, CA1.CD2 without HER2 affibody did not bind to either of the tested cultured cells (FIG. 4.2). Proteins binding to cell surface HER2 with a clear membrane staining pattern in AU565 cells was observed at 4° C. The binding of the proteins to the cells triggered receptor-mediated endocytosis at 37° C. as demonstrated by the staining of the protein inside the cells. In addition, PEGylation of the targeted contrast agent PEG-CA1-Affi does not change its target capability the positive cell as shown in FIG. 4.2 at both 4 and 37° C. Further labeling with NIR dye Cy5.5, the binding of the contrast agent (PEG-CA1-Affi-Cy5.5) to both AU565 and SKOV-3, a cell line derived from ovarian cancer with very high HER2 expression, is readily detected by our fluorescence microscope.

Binding of the Gd-CA1-Affi to the cancer cells was further analyzed by quantification of cell bound $Gd^{3+}$ with AU565 and EMT6 cells. The amounts of $Gd^{3+}$ were quantified by γ-counting the trace of isotope $^{153}Gd^{3+}$ in the Gd-protein complexes. The quantification of cell bound $Gd^{3+}$ supported our immuno-analyses that Gd-CA1-Affi exhibited targeted binding to AU565 cells but not to EMT6 cells (FIGS. 4.3A and 4.3B). The protein without the HER2 affibody targeting moiety could not bind to the cells that express HER2. Interestingly, calculating the amounts of bound $Gd^{3+}$ from γ-counting revealed that the $Gd^{3+}$ ions were bound to cells at ~0.2 fmole Gd/cell. Based on the assumption that $1 \times 10^7$ cells occupy a volume of 50-100 μl, this binding capacity leads to the accumulation of $Gd^{3+}$ at 5-15 μM in the cell pellets. This local concentration is sufficient to produce strong MRI contrast, especially with high relaxivity protein-based contrast agent. Further, the level of HER expression can be monitored by ELISA (FIGS. 4.3A and 4.3B).

4.3 MRI Imaging of Different Cancer Cells by the Developed HER2 Targeting Contrast Agents Experiments demonstrated that the developed MRI contrast agent binds specifically to HER2 expression cells. To test whether our designed proteins are applicable for targeted imaging, we carried out MR imaging of cancer cells that were incubated with the designed protein contrast agents Gd-CA1-Affi using four different cancer cell lines with different expression levels of HER2. Cancer cells AU565 and SKOV3, with high numbers of HER2, exhibit a brighter imaging in the presence of our contrast agent Gd-CA1.HER2-Affi. In contrast, no significant changes in MR image were observed in the imaging pellets of AU565 and SKOV3 cells that were incubated with Gd-CA1.CD2, without the HER2 targeting moiety. The MR imaging of MDA-MB-231, another breast cancer cell line with limited HER2 expression, demonstrated slight contrast enhancement. Almost no contrast enhancement was observed with MR imaging of EMT6 cells using our HER2 targeting contrast agent. Quantification of the MR image intensity revealed a strong correlation between MR imaging intensity and the HER2 levels among the different cell lines used. These results confirm that the addition of HER2 targeting affibody to our protein contrast agent has the potential to provide molecular imaging of cancer cells via receptor-mediated recognition. The MR image contrast enhancements from the contrast agent can be correlated to the HER2 levels.

4.4 the HER2 Targeting Contrast Agent Provided Strong MR Image Contrast Enhancement in Nude Mice Xenograft Model We next tested whether our designed contrast agent would produce MR imaging contrast enhancement in nude mice xenograft models of two human cancer cell lines, SKOV3 and MDA-MB-231. Since AU565 did not grow tumors in nude mice, we used SKOV3 and MDA-MB-231 cell lines. The HER2 positive SKOV3 and negative MDA-MB-231 tumors were implanted on the right and left flanks, respectively, of different mice (FIG. 4.5). The contrast agent Gd-CA1.HER2/Affi (60 μl) was introduced via the tail vein at concentration of 6 mM. Pre- and post-contrast MRIs were collected at different time points using T1 weighted spin echo or gradient echo sequences. At an early time point (40 minutes), little contrast enhancement was observed with either HER2 positive or negative tumors. The contrast enhancements with both positive and negative tumors were apparent at 4 hours post-contrast agent injection. However, after 21 hours post-contrast, the image enhancements of the negative tumor decreased dramatically, while conversely there were no significant decreases in the MRI intensities in the positive tumor. In parallel, the mice were imaged using a Kodak in vivo FX-pro animal imaging system. Consistent with MRI imaging, we observed strong NIR light emission from both positive and negative tumor sites at early time points (50 minutes post-injection). After 24 hours post-contrast, the NIR intensities at the negative tumor site were almost identical with the background, while the light intensities at the positive tumor experienced only a minor decrease (FIG. 4.5). The in vivo imaging experiments were repeated with four tumor-bearing mice (four positive tumor mice and four negative tumor mice) with similar results. FIG. 4.4, shows the result of another mouse. 5 mM of contrast agent CA1.Affi-P40 (100 fold lower than clinic used DTPA) was injected via tail vein. MRI images at 4.7 T using fast spin echo were acquired before injection, 5 min, 30 min, 3 hr, 24 hr and 52 hr post injection. Positive tumor shows a strong contrast after 30 mins and peaked at 24 hour with about 35% enhancement. Contrast capability was decreased after 52 hours, suggesting that the contrast agent was secreted of out the animal. This mouse was alive and looks normal after 52 hours MRI scanning.

4.5 IHC Analyses and NIR Imaging Indicate Molecular Targeting Rather than Vascular Retention To further analyze the HER2 targeting properties of the protein contrast agent, tumors and organs from the imaged mice were collected after imaging at 45 minutes or 24 hours. The organs and tumors were imaged under the Kodak in vivo FX-pro animal imaging system. It was clear that there were very high levels of accumulation of Cy5.5 at the liver and HER2 positive tumor, with moderate levels of the NIR dye present in the kidney and spleen. NIR fluorescence intensities in the lung and heart were very weak. The IHC analyses are consistent with our biodistribution analyses of the contrast agent in CD1 mouse. The levels of Cy5.5 at the negative tumor were also very weak (FIG. 4.6). There was almost no detectable NIR fluorescence in the muscles.

Targeting of the protein contrast agent to HER2 positive tumor was further analyzed by immunoblot. To this end, protein extracts were made from the tissue samples that were collected from the imaged mice. Immunoblot experiments were performed with the protein extracts using the antibody PAbPGCA1. Consistently, we detected very high levels of PEGylated protein contrast agent in extracts made from liver, kidney, and positive tumor. The antibody detected very faint bands in the extracts made from muscle and negative tumor samples (FIG. 4.6). The results strongly suggested that our protein contrast agent led to a HER2 specific MR image enhancement.

In addition, we carried out immunohistochemistry (IHC) staining using the antibody PAbPGCA1 with tissue slides made from the tissue samples from the imaged mice, including HER2 positive and negative tumors. Strongest staining was observed with liver and HER2 positive tumor tissue slides (FIG. 4.7). Close examination of the staining patterns of the positive tumor slides revealed very high CA1-Affi protein levels inside the cancer cells, indicating internalization (endocytosis) of the protein contrast agent. The results also suggested that the contrast agent penetrated the tumor tissue, rather than being trapped in the tumor vasculature. This is an important property for HER2 targeting in the whole cancer mass. The kidney slides also gave strong immunostaining. Interestingly, the areas near proximal tubes showed the strongest staining in the slides made from the kidney (FIG. 4.7), indicating that the protein contrast agent was ready to be filtered through the kidney. This is consistent with observations that there were good levels of both $Gd^{3+}$ (by $\gamma$-counting of $Gd^{3+}$-153) and protein CA1-Affi (by NIR fluorescence) in the urine of mice that were injected with PEGylated Gd-CA1-Affi. Co-immunostaining the slides made from HER2 positive tumor with the antibody PAbPGCA1 and the antibody against CD31, an endothelial molecular marker, demonstrated that the protein contrast agent largely localized in tissue areas other than the tumor micro-vascular structure (CD31 positive areas). This staining pattern suggested that the designed protein contrast had penetrated tissue rather than simply being trapped in the blood in the micro-vasculature of the tumor tissue.

4.6 HER2-Targeted Contrast Agent has been Generated by Engineering Metal Binding Sites in Natural Calcium Binding Proteins We have created the second generation contrast agent by grafting affibody within the engineered multiple metal binding protein CBP1 based on calmodulin (CBP1-affi). In addition GRP/Bombesin sequence was also inserted into CBP1 to create a contrast agent to specifically target to prostate cancer with GRPR over expressed (CBP1-Bom). These targeted contrast agents were then PEGylated by PEG with different units and purified. Initial binding to HER2 has been studied. The HER2 positive cell line SKOV-3 and HER2 negative cell line MDA-MB-231 was treated with CBP1-affi at different concentration: 10 µM and 20 µM in 1 ml medium. Both of the cell numbers is about $1 \times 10^5$. One hour later, the medium will be carefully washed for 3 times. The non-binding proteins will be washed away. Then the cells will be lysized by RIPA buffer for 30 min and centrifuged to obtain the cell lysate. The cell lysate is used to run western blot to measure the binding of CBP1-affi with HER2 positive cells. FIG. 4.8 shows that the bands in SKOV-3 cells are much darker than those in MDA-MB-231 cells, which means the binding of CBP1-affi to HER2 is specific.

The two cell lines been treated with CBP1-affi are fixed in chamber by cold methanol for 5 min. Then primary antibody against CBP1-affi and secondary antibody will be applied consequently. Finally, the slides will be mounted by anti fade reagent with DAPI staining. The second day, images will be taken under microscope. The green color indicates FITC staining on CBP1-affi; the blue color indicates the nuclear staining. FIG. 4.9 shows the HER2 positive cell line SKOV-3 has been stained. The staining on the negative cell line is rarely.

4.7 GRP Receptor Targeted Contrast Agents have been Created for Both NIRfluorescence and MRI to Image Prostate Cancer Both in Cells and in Mice We have also created targeted contrast agents to against biomarker GRPR that are over-expressed in prostate, colon, breast, and pancreatic cancers by grafting Bom/GRP sequence into CA1.CD2 (CA1.CD2-521-Bom. This protein was also pegylated by PEG40 (CA1.CD2-52I-Bom-P40). NIR dye such as Cy5.5 was also conjugated at the C-terminal Cys (CA1.CD2-52I-Bom-P40-Cy5.5). FIG. 4.9 shows the uptake and internalization of CA1.Bom (CA1.CD2-521-Bom) specifically to GRPR positive cell lines (PC-3 and DU-145 cells) by using confocal fluorescent microscope.

DU-145, PC-3 and H441 cells ($8 \times 10^4$) were seeded in 4-well chambers (BD) at 37° C. overnight. In the second day, fresh medium was changed. Contrast agents were incubated with cells at different time point at 37° C. Subsequently, the cells were washed with PBS for three times and fixed with 3% formaldehyde for 15 minutes. After cells were rinsed in PBS for three times, 0.2% Triton X-100 was added to permeablize cells for 10 minutes. The cells were washed and four drops of Image-IT Fx signal enhancer (Invitrogen, CA) was applied in each sample to block unspecific binding. After three time washes, CD2 antibody was used as primary antibody. Goat anti-mouse IgG conjugated with Alexa Fluor 488 was used as detection antibody (Invitrogen, CA). The fluorescence image was acquired using 488 nm and UV lasers.

FIG. 4.11 shows NIR-fluorescence imaging of nude mice xenografted with DU-145 tumor (positive control left) and H441 tumor (control, right) post injection of CA1.CD2-52Ibom-cy5.5-P40 26 hours via tail vein. 50 uM Cy5-CA1.CD2-52I was injected into mouse tail vein. After 26 hours, mouse was analyzed by Kodak Imaging System. Tissue organs were taken out and analyzed. Tumor intensity was analyzed by Image J. FIG. 4.12 shows NIR imaging (top) and NIR intensity (bottom) of CA1.CD2-52I-Bom- Cy5.5-P40 at different organs of the mice. The developed contrast agent is able to target to the GRPR expressed tumor monitored by NIR fluorescence.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Sequence Listings:

Listed sequences are representative examples from protein families where sequences of the same protein across different species typically share 50-98% sequence homology. As an embodiment, attributes in the cited sequence can be inferred to apply to homologous, related sequences, which would be known to someone familiar with the art.

K Possible PEGylated sites

X Mutation sites, C is added at the C-terminal for specific pegylation or conjugating to fluorescence dye. Specific pegylation can also be at N-terminal These sequences include for different species. A SEQ ID No: ("#") is noted by each sequence below.

```
Rat Calmodulin and its variants (CBP01 and variants)
WT (wild type) (1)
ADQLTEEQIAEFKEAFSLFDKDGDGTITTKELGTVMRSLGQNPTEAELQDMINEVDADGN    60

D93A (2)
ADQLTEEQIAEFKEAFSLFDKDGDGTITTKELGTVMRSLGQNPTEAELQDMINEVDADGN    60

D129A (3)
ADQLTEEQIAEFKEAFSLFDKDGDGTITTKELGTVMRSLGQNPTEAELQDMINEVDADGN    60

D56A (4)
ADQLTEEQIAEFKEAFSLFDKDGDGTITTKELGTVMRSLGQNPTEAELQDMINEVAADGN    60

D20A (5)
ADQLTEEQIAEFKEAFSLFAKDGDGTITTKELGTVMRSLGQNPTEAELQDMINEVDADGN    60

Y99W (6)
ADQLTEEQIAEFKEAFSLFDKDGDGTITTKELGTVMRSLGQNPTEAELQDMINEVDADGN    60

T26W (7)
ADQLTEEQIAEFKEAFSLFDKDGDGWITTKELGTVMRSLGQNPTEAELQDMINEVDADGN    60

N60D-N97D (8)
ADQLTEEQIAEFKEAFSLFDKDGDGTITTKELGTVMRSLGQNPTEAELQDMINEVDADGD    60

Deletion (9)
ADQLTEEQIAEFKEAFSLFDKDGDGTITTKELGTVMRSLGQNPTEAELQDMINEVDADGN    60

D-N60D-N97D (10)
ADQLTEEQIAEFKEAFSLFDKDGDGTITTKELGTVMRSLGQNPTEAELQDMINEVDADGD    60

WT
GTIDFPEFLTMMARKMKDTDSEEEIREAFRVFDIDGNGYISAAELRHVMTNLGEKLTDEE  120

D93A
GTIDFPEFLTMMARKMKDTDSEEEIREAFRVFAIDGNGYISAAELRHVMTNLGEKLTDEE  120

D129A
GTIDFPEFLTMMARKMKDTDSEEEIREAFRVFDIDGNGYISAAELRHVMTNLGEKLTDEE  120

D56A
GTIDFPEFLTMMARKMKDTDSEEEIREAFRVFDIDGNGYISAAELRHVMTNLGEKLTDEE  120

D20A
GTIDFPEFLTMMARKMKDTDSEEEIREAFRVFDIDGNGYISAAELRHVMTNLGEKLTDEE  120

Y99W
GTIDFPEFLTMMARKMKDTDSEEEIREAFRVFDIDGNGWISAAELRHVMTNLGEKLTDEE  120

T26W
GTIDFPEFLTMMARKMKDTDSEEEIREAFRVFDGDNGYISAAELRHVMTNLGEKLTDEE  120

N60D-N97D
GTIDFPEFLTMMARKMKDTDSEEEIREAFRVFDKDGDGYISAAELRHVMTNLGEKLTDEE  120
```

```
Deletion
GTIDFPEFLTMMARK------EEEIREAFRVFDKDGNGYISAAELRHVMTNLGEKLTDEE    115

D-N60D-N97D
GTIDFPEFLTMMARK------EEEIREAFRVFDKDGDGYISAAELRHVMTNLGEKLTDEE    115

WT
VDEMIREADIDGDGQVNYEEFVQMMTAK                                    148

D93A
VDEMIREADIDGDGQVNYEEFVQMMTAK                                    148

D129A
VDEMIREAAIDGDGQVNYEEFVQMMTAK                                    148

D56A
VDEMIREADIDGDGQVNYEEFVQMMTAK                                    148

D20A
VDEMIREADIDGDGQVNYEEFVQMMTAK                                    148

Y99W
VDEMIREADIDGDGQVNYEEFVQMMTAK                                    148

T26W
VDEMIREADIDGDGQVNYEEFVQMMTAK                                    148

N60D-N97D
VDEMIREADIDGDGQVNYEEFVQMMTAK                                    148

Deletion
VDEMIREADIDGDGQVNYEEFVQMMTAK                                    143

D-N60D-N97D
VDEMIREADIDGDGQVNYEEFVQMMTAK                                    143

Rat N-Calmodulin (N-terminal domain of Calmodulin and variants)
N-CaM (11)
ADQLTEEQIAEFKEAFSLFDKDGDGTITTKELGTVMRSLGQNPTEAELQDMINEVDADGN    60

N-N60D (12)
ADQLTEEQIAEFKEAFSLFDKDGDGTITTKELGTVMRSLGQNPTEAELQDMINEVDADGD    60

N-CaM
GTIDFPEFLTMMARK                                                  75

N-N60D
GTIDFPEFLTMMARK                                                  75

Rat C-Calmodulin (N-terminal domain of Calmodulin and variants)
C-CaM (13)
MKDTDSEEEIREAFRVFDIDGNGYISAAELRHVMTNLGEKLTDEEVDEMIREADIDGDGQ    60

C-N97D (14)
MKDTDSEEEIREAFRVFDIDGDGYISAAELRHVMTNLGEKLTDEEVDEMIREADIDGDGQ    60

C-CaM
VNYEEFVQMMTAK                                                    73

C-N97D
VNYEEFVQMMTAK                                                    73

Rat Calmodulin-affibody (15)
ADQLTEEQIAEFKEAFSLFDKDGDGTITTKELGTVMRSLGQNPTEAELQDMINEVDADGD

GTIDFPEFLTMMARKMKDTGGSGGVDNKFNKEMRNAYWEIALLPNLNNQQKRAFIRSLYD

DPSQSANLLAEAKKLNDAQAPKGGSGGDSEEEIREAFRVFDKDGDGYISAAELRHVMTNL

GEKLTDEEVDEMIREADIDGDGQVNYEEFVQMMTAK

Rat CaM-Bombesin (16)
ADQLTEEQIAEFKEAFSLFDKDGDGTITTKELGTVMRSLGQNPTEAELQDMINEVDADGD

GTIDFPEFLTMMARKMKDTGGNQWAVGHLMGGDSEEEIREAFRVFDKDGDGYISAAELRH

VMTNLGEKLTDEEVDEMIREADIDGDGQVNYEEFVQMMTAK
```

```
Calmodulin different species
Human (17)
ADQLTEEQIAEFKEAFSLFDKDGDGTITTKELGTVMRSLGQNPTEAELQDMINEVDADDL   60

Mouse (18)
ADQLTEEQIAEFKEAFSLFDKDGDNTITTKELGTVMRSLGQNPTEAELQDMINEVDAD--   58

Rat (19)
ADQLTEEQIAEFKEAFSLFDKDGDGTITTKELGTVMRSLGQNPTEAELQDMINEVDAD--   58

Rabbit (20)
ADQLTEEQIAEFKEAFSLFDKDGDGTITTKELGTVMRSLGQNPTEAELQDMINEVDAD--   58

Paramecium (21)
AEQLTEEQIAEFKEAFALFDKDGDGTITTKELGTVMRSLGQNPTEAELQDMINEVDAD--   58

Human
PGNGTIDFPEFLTMMARKMKDTDSEEEIREAFRVFDKDGNGYISAAELRHVMTNLGEKLT  120

Mouse
-GNGTIDFPEFLTMMARKMKDTDSEEEIREAFRVFDKDGNGYISAAELRHVMTNLGEKLT  117

Rat
-GNGTIDFPEFLTMMARKMKDTDSEEEIREAFRVFDKDGNGYISAAELRHVMTNLGEKLT  117

Rabbit
-GNGTIDFPEFLTMMARKMKDTDSEEEIREAFRVFDKDGNGYISAAELRHVMTNLGEKLT  117

Paramecium
-GNGTIDFPEFLSLMARKMKEQDSEEELIEAFKVFDRDGNGLISAAELRHVMTNLGEKLT  117

Human
DEEVDEMIREADIDGDGQVNYEEFVQMMTAK                              151

Mouse
DEEVDEMIREADIDGDGQVNYEEFVQMMTAK                              148

Rat
DEEVDEMIREADIDGDGQVNYEEFVQMMTAK                              148

Rabbit
DEEVDEMIREADIDGDGQVNYEEFVQMMTAK                              148

Paramecium
DDEVDEMIREADIDGDGHINYEEFVRMMVSK                              148

Rat CA1-CD2-Affibody
CA1-WT (22)
GSRDSGTVWGALGHGIELNIPNFQMTDDIDEVRWERGSTLVAEFKRKMKPFLKSGAFEID   60

CA1-Z$_{HER2-4}$ (23)
GSRDSGTVWGALGHGIELNIPNFQMTDDIDEVRWERGSTLVAEFKRKMKPFLKSGAFEID   60

CA1-Z$_{HER342}$ (24)
GSRDSGTVWGALGHGIELNIPNFQMTDDIDEVRWERGSTLVAEFKRKMKPFLKSGAFEID   60

CA1-WT
ANGDLDDKNLTRDDSGTYNVTVYSTNGTRILNKALDLRILEGGSGGVDNKFNXEQQNAFY  120

CA1-Z$_{HER2-4}$
ANGDLDIKNLTRDDSGTYNVTVYSTNGTRILNKALDLRILEGGSGGVDNKFNKELRQAYW  120

CA1-Z$_{HER342}$
ANGDLDIKNLTRDDSGTYNVTVYSTNGTRILNXALDLRILEGGSGGVDNKFNKEMRNAYW  120

CA1-WT
EILHLPNLNEEQRNAFIQSLKDDPSQSANLLAEAKKLNDAQAPK                 164

CA1-Z$_{HER2-4}$
EIQALPNLNWTQSRAFIRSLYDDPSQSANLLAEAKKLNDAQAPK                 164

CA1-Z$_{HER342}$
EIALLPNLNNQQXRAFIRSLYDDPSQSANLLAEAKKLNDAQAPK                 164

Rat CA1-CD2-Bombesin (C-terminal) (25)
RDSGTVWGAL GHGIELNIPN FQMTDDIDEV RWERGSTLVA EFKRKMKPFL

KSGAFEIDAN GDLDIKNLTR DDSGTYNVTV YSTNGTRILN KALDLRILEG

GSGGSGNQWA VGHLM
```

```
Rat CA1-CD2-Bombesin (521) (26)
RDSGTVWGAL GHGIELNIPN FQMTDDIDEV RWERGSTLVA EFKRKMKPFL

KSGGSGGGNQ WAVGHLMGGS GGGAFEIDAN GDLDIKNLTR DDSGTYNVTV

YSTNGTRILN KALDLRILE

Rat Parvalbumin
WT (27)
MSMTDLLSAEDIKKXAIGAFTAADSFDHKKFFQMVGLKKKSADDVKKVFHILDKDKSGFIE    60

S56D (28)
MSMTDLLSAEDIKKXAIGAFTAADSFDHKKFFQMVGLKKKSADDVKKVFHILDKDKDGFIE    60

S56D-F103W(29)
MSMTDLLSAEDIKKXAIGAFTAADSFDHKKFFQMVGLKKKSADDVKKVFHILDKDKDGFIE    60

E60D (30)
MSMTDLLSAEDIKKXAIGAFTAADSFDHKKFFQMVGLKKKSADDVKKVFHILDKDKSGFID    60

E60D-F103W (31)
MSMTDLLSAEDIKKXAIGAFTAADSFDHKKFFQMVGLKKKSADDVKKVFHILDKDKSGFID    60

G99D (32)
MSMTDLLSAEDIKKXAIGAFTAADSFDHKKFFQMVGLKKKSADDVKKVFHILDKDKSGFIE    60

G99D-F103W (33)
MSMTDLLSAEDIKKXAIGAFTAADSFDHKKFFQMVGLKKKSADDVKKVFHILDKDKSGFIE    60

D53S-F103W (34)
MSMTDLLSAEDIKKXAIGAFTAADSFDHKKFFQMVGLKKKSADDVKKVFHILSKDKSGFIE    60

D53E-F103W (36)
MSMTDLLSAEDIKKXAIGAFTAADSFDHKKFFQMVGLKKKSADDVKKVFHILEKDKSGFIE    60

F103WC104 (37)
MSMTDLLSAEDIKKXAIGAFTAADSFDHKKFFQMVGLKKKSADDVKKVFHILDKDKSGFIE    60

F103W (38)
MSMTDLLSAEDIKKXAIGAFTAADSFDHKKFFQMVGLKKKSADDVKKVFHILDKDKSGFIE    60

Human (39)
MSMTDLLNAEDIKKXAVGAFSATDSFDHKKFFQMVGLKKKSADDVKKVFHMLDKDKSGFIE    60

WT
EDELGSILKGFSSDARDLSAKETKTLMAAGDKDGDGKIGVEEFSTLVAES-              110

S56D
EDELGSILKGFSSDARDLSAKETKTLMAAGDKDGDGKIGVEEFSTLVAES-              110

S56D-F103W
EDELGSILKGFSSDARDLSAKETKTLMAAGDKDGDGKIGVEEWSTLVAES-              110

E60D
EDELGSILKGFSSDARDLSAKETKTLMAAGDKDGDGKIGVEEFSTLVAES-              110

E60D-F103W
EDELGSILKGFSSDARDLSAKETKTLMAAGDKDGDGKIGVEEWSTLVAES-              110

G99D
EDELGSILKGFSSDARDLSAKETKTLMAAGDKDGDGKIDVEEFSTLVAES-              110

G99D-F103W
EDELGSILKGFSSDARDLSAKETKTLMAAGDKDGDGKIDVEEWSTLVAES-              110

G99D-F103W
EDELGSILKGFSSDARDLSAKETKTLMAAGDKDGDGKIDVEEWSTLVAES-              110

G99D-F103W
EDELGSILKGFSSDARDLSAKETKTLMAAGDKDGDGKIDVEEWSTLVAES-              110

F103WC104
EDELGSILKGFSSDARDLSAKETKTLMAAGDKDGDGKIGVEEWSTLVAESC              111

F103W
EDELGSILKGFSSDARDLSAKETKTLMAAGDKDGDGKIGVEEWSTLVAES-              110

Human
EDELGFILKGFSPDARDLSAKETKMLMAAGDKDGDGKIGVDEFSTLVAES-              110
```

-continued

Rat-Parvalbumin Insertion variants
```
PV_Collagen (39)
MSMTDLLSAEDIXKKAIGAFTAADSFDHKKXFFQMVGLKKKSADDVKKVFHILDKDKDG-     60
FIE PV_Bombsin (40)
MSMTDLLSAEDIKKAIGAFTAADSFDHKKXFFQMVGLKKKSADDVKKVFHILDKDKDGFIE    60

PV_Selectin (41)
MSMTDLLSAEDIKKAIGAFTAADSFDHKKXFFQMVGLKKKSADDVKKVFHILDKDKDGFIE    60

PV_RGD (42)
MSMTDLLSAEDIKKAIGAFTAADSFDHKKFFQMVGLKKKSADDVKKVFHILDKDKDGFIE     60

PV_Cys (43)
MSMTDLLSAEDIKKAIGAFTAADSFDHKKFFQMVGLKKKSADDVKKVFHILDKDKDGFIE     60

PV_AFFIBODY (44)
MSMTDLLSAEDIKKAIGAFTAADSFDHKKFFQMVGLKKKSADDVKKVFHILDKDKDGFIE     60

PV_Collagen
EDELGSILXGFSSDARDLSAKETKTLMAAGDKDGDGKIGVEEWSTLVAESGGGKKWHCYT    120

PV_Bombsin
EDELGSILXGFSSDARDLSAKETKTLMAAGDKDGDGKIGVEEWSTLVAESGGGAQWAVGH    120

PV_Selectin
EDELGSILXGFSSDARDLSAKETKTLMAAGDKDGDGKIGVEEWSTLVAESGGG-KYDGDI    119

PV_RGD
EDELGSILXGFSSDARDLSAKETKTLMAAGDKDGDGKIGVEEWSTLVAESGGGRGDRGDR    120

PV_Cys
EDELGSILXGFSSDARDLSAKETKTLMAAGDKDGDGKIGVEEWSTLVAESC---------   111

PV_AFFIBODY
EDELGSILXGFSSDARDLSAKETKTLMAAGDKDGDGKIGVEEWSTLVAESGGSGGVDNKF    120

PV_Collagen
YFPHRYCVYG-------------------------------------------         130

PV_Bombsin
LM---------------------------------------------------         122

PV_Selectin
TWDQLWDLMX-------------------------------------------         129

PV_RGD
GDRGD------------------------------------------------         125

PV_Cys
-----------------------------------------------------

PV_AFFIBODY
NKEMPNAYWEIALLPNLNNQQKRAPIRSLYDDPSQSANLLAEAXKLNDAQAPK           173

Human-Calbindin D9k
CalbindinD9k (45)
MSTKKSPEELKRIFEKYAAKEGDPDQLSKDELKLLIQAEFPSLLKGPNTLDDLFQELDKN     60

CalbindinD9kF67W (46)
MSTKKSPEELKRIFEKYAAKEGDPDQLSKDELKLLIQAEFPSLLKGPNTLDDLFQELDKN     60

CalbindinD9kP43M (47)
MSTKKSPEELKRIFEKYAAKEGDPDQLSKDELKLLIQAEFPSLLKGMNTLDDLFQELDKN     60

CalbindinD9kCys (48)
MSTKKSPEELRIFEKYAAKEGDPDQLSKDELKLLIQAEFPSLLKGPNTLDDLFQELDKN      60

CalbindinD9k
GDGEVSFEEFQVLVKKISQ-                                            79

CalbindinD9kF67W
GDGEVSFEEWQVLVKKISQ-                                            79

CalbindinD9kP43M
GDGEVSFEEWQVLVKKISQ-                                            79

CalbindinD9kCys
GDGEVSFEEFQVLVKKISQC                                            80
```

-continued

Human-Troponin C (49)
MTDQQAEARSYLSEEMIAEFKAAFDMFDADGGGDISVKELGTVMRMLGQTPTKEELDAIIEEVD

EDGSGTIDFEEFLVMMVRQMKEDAKGXSEEELAECFRIFDRNADGYIDPGELAEIFRASGEHVT

DEEIESLMXDGDKNNDGRIDFDEFLKMMEGVQ

Rat CA1-CD2-Bombesin-RGD (52I)-Cend (50)
RDSGTVWGAL GHGIELNIPN FQMTDDIDEV RWERGSTLVA EFKRKMXPFL

KSGGSGGGNQ WAVGHLMGGS GGGAFEIDAN GDLDIKNLTR DDSGTYNVTV

YSTNGTRILN KALDLRILE-RGD

Rat CA1-CD2-Bombesin-RGD (52I)-Nend (51)
RGDRDSGTVWGAL GHGIELNIPN FQMTDDIDEV RWERGSTLVA EFKRKMKPFL

KSGGSGGGNQ WAVGHLMGGS GGGAFEIDAN GDLDIKNLTR DDSGTYNVTV

YSTNGTRILN KALDLRILE

Rat CA1-CD2-RGD-83I (52)
RDSGTVWGAL GHGIELNIPN FQMTDDIDEV RWERGSTLVA EFKRKMKPFL

KSGAFEIDAN GDLDIKNMLTR DDSGTYNVTV YSTGGSGGRGDGGSGGNGTRILN

KALDLRILEG

Rat CA1-CD2-Bom-52I-RGD-83I (53)
RGDRDSGTVWGAL GHGIELNIPN FQMTDDIDEV RWERGSTLVA EFKRKMXPFL

KSGGSGGGNQ WAVGHLMGGS GGGAFEIDAN GDLDIKNLTR DDSGTYNVTV

YSTGGSGGRGDGGSGGNGTRILN KALDLRILE

---

We claim the following:

1. A contrast agent comprising a modified parvalbumin scaffold polypeptide, wherein one or more amino acids of the scaffold polypeptide form at least one paramagnetic metal ion chelating site, and further comprising a paramagnetic metal ion bound to at least two of the amino acids forming the at least one paramagnetic metal ion chelating site, wherein the modified parvalbumin scaffold polypeptide has at least one amino acid substitution that modifies at least one of the metal selectivity of the binding site, increases binding affinity for the metal, or increases serum stability of the contrast agent, and wherein the at least one amino acid substitution is selected from the group consisting of S56D, E60D, G99D, and F103W, wherein the amino acid positions are numbered according to SEQ ID NO: 38, and wherein the modified parvalbumin scaffold polypeptide having the paramagnetic metal ion bound thereto is detectable by magnetic resonance imaging (MRI).

2. The contrast agent of claim 1, wherein the modified parvalbumin scaffold polypeptide has an amino acid sequence having at least 90% similarity to any of SEQ ID Nos: 28-38.

3. The contrast agent of claim 1, wherein the modified parvalbumin scaffold polypeptide has an amino acid sequence selected from the group consisting of SEQ ID Nos: 28-38.

4. The contrast agent of claim 1, including at least one post-translational modification.

5. The contrast agent of claim 1, further comprising at least one polyethylene glycol (PEG) group or glucan group attached to the modified parvalbumin scaffold polypeptide.

6. The contrast agent of claim 1, wherein at least two metal ion chelating sites are comprised of amino acids of the modified parvalbumin scaffold polypeptide, and wherein each of the metal ion chelating sites has a paramagnetic ion independently bound thereto.

7. The contrast agent of claim 1, further comprising a targeting agent attached to the polypeptide, wherein the targeting agent is a biomarker probe, a precancerous targeting agent, a cancer targeting agent, a tumor targeting agent, a fibrosis targeting agent, or a detectable probe or agent that targets a biomarker, a precancerous cell, a cancer cell, or a tumor.

8. The contrast agent of claim 5, wherein the PEG has a molecular weight of about 1 to 100 kDa.

9. The contrast agent of claim 5, wherein the PEG is attached to the modified parvalbumin scaffold polypeptide via a lysine, a glutamic acid, a aspartic acid, a cysteine, the polypeptide carboxy-terminus, the polypeptide amino-terminus, or a combination thereof.

10. The contrast agent of claim 5, wherein at least one metal ion chelating site is at least substantially embedded within the modified parvalbumin scaffold polypeptide.

11. The contrast agent of claim 5, wherein the paramagnetic metal ion is selected from the group consisting of: Gd(III), Mn(II), Fe(II), Fe(III), Co(II), Co(III), Ni(III), Mo(V), and V(IV).

12. The contrast agent of claim 11, wherein the paramagnetic metal ion is Gd(III).

13. The contrast agent of claim 7, wherein the targeting agent targets to Her-2, EGFR, GRPR, integrin, or collagen.

14. The contrast agent of claim 7, wherein the targeting agent is a detectable Near-IR functional group covalently bound to the modified parvalbumin scaffold polypeptide.

15. A method of imaging a sample comprising:

contacting a sample with a composition comprising a contrast agent comprising a modified parvalbumin scaffold polypeptide, wherein one or more amino acids of the scaffold polypeptide form at least one paramagnetic metal ion chelating site, and further comprising a paramagnetic metal ion bound to at least two of the amino acids forming the at least one paramagnetic metal ion chelating site, wherein the modified parvalbumin scaffold polypeptide has at least one amino acid substitution that modifies at least one of the metal selectivity of the binding site, increases binding affinity for the metal, or increases serum stability of the contrast agent, and wherein the at least one amino acid substitution is selected from the group consisting of S56D, E60D, G99D, and F103W, wherein the amino acid positions are numbered according to SEQ ID NO: 38, and wherein the modified parvalbumin scaffold polypeptide having the paramagnetic metal ion bound thereto is detectable by magnetic resonance imaging (MRI);

introducing the sample contacted with the composition to an imaging system;

detecting a signal generated by or from the contrast agent of the introduced sample; and generating an image of the sample from the signal.

16. The method of claim 15, wherein the modified parvalbumin scaffold polypeptide comprises an amino acid sequence selected from the group consisting of SEQ ID Nos: 28-38.

* * * * *

SEQUENCE LISTING

<160> NUMBER OF SEQ ID NOS: 53

<210> SEQ ID NO 1
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 1

```
Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Ile Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145
```

```
<210> SEQ ID NO 2
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 2

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Ala Ile Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
            115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 3
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 3

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Ile Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
            115                 120                 125

Ala Ile Asp Gly Asp Gly Gln Val Asn Tyr Glu Glu Phe Val Gln Met
    130                 135                 140

Met Thr Ala Lys
```

<210> SEQ ID NO 4
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 4

```
Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Ala Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Ile Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145
```

<210> SEQ ID NO 5
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 5

```
Ala Asp Gln Leu Thr Glu Glu Gln Ile Ala Glu Phe Lys Glu Ala Phe
1               5                   10                  15

Ser Leu Phe Ala Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Ile Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140
```

Met Thr Ala Lys
145

<210> SEQ ID NO 6
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 6

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Ile Asp Gly
                85                  90                  95

Asn Gly Trp Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 7
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 7

Ala Asp Gln Leu Thr Glu Glu Gln Ile Ala Glu Phe Lys Glu Ala Phe
1               5                   10                  15

Ser Leu Phe Asp Lys Asp Gly Asp Gly Trp Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Ile Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 8
<211> LENGTH: 148
<212> TYPE: PRT
<213> ORGANISM: Artificial Sequence
<220> FEATURE:
<223> OTHER INFORMATION: Chemically Synthesized Calmodulin Protein

<400> SEQUENCE: 8

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asp Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asp Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 9
<211> LENGTH: 142
<212> TYPE: PRT
<213> ORGANISM: Artificial Sequence
<220> FEATURE:
<223> OTHER INFORMATION: Chemically Synthesized Calmodulin Protein

<400> SEQUENCE: 9

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Glu Glu Glu Ile Arg
65                  70                  75                  80

Glu Ala Phe Arg Val Phe Asp Lys Asp Gly Asn Gly Tyr Ile Ser Ala
            85                  90                  95

Ala Glu Leu Arg His Val Met Thr Asn Leu Gly Glu Lys Leu Thr Asp
            100                 105                 110

Glu Glu Val Asp Glu Met Ile Arg Glu Ala Asp Ile Asp Gly Asp Gly
        115                 120                 125

Gln Val Asn Tyr Glu Glu Phe Val Gln Met Met Thr Ala Lys

-continued

```
            130                 135                 140

<210> SEQ ID NO 10
<211> LENGTH: 142
<212> TYPE: PRT
<213> ORGANISM: Artificial Sequence
<220> FEATURE:
<223> OTHER INFORMATION: Chemically Synthesized Calmodulin Protein

<400> SEQUENCE: 10

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asp Gly Thr Ile Asp
    50                  55                  60

Phe Pro Glu Phe Leu Thr Met Met Ala Arg Lys Glu Glu Glu Ile Arg
65                  70                  75                  80

Glu Ala Phe Arg Val Phe Asp Lys Asp Gly Asp Gly Tyr Ile Ser Ala
                85                  90                  95

Ala Glu Leu Arg His Val Met Thr Asn Leu Gly Glu Lys Leu Thr Asp
            100                 105                 110

Glu Glu Val Asp Glu Met Ile Arg Glu Ala Asp Ile Asp Gly Asp Gly
        115                 120                 125

Gln Val Asn Tyr Glu Glu Phe Val Gln Met Met Thr Ala Lys
    130                 135                 140

<210> SEQ ID NO 11
<211> LENGTH: 74
<212> TYPE: PRT
<213> ORGANISM: Artificial Sequence
<220> FEATURE:
<223> OTHER INFORMATION: Chemically Synthesized Calmodulin Protein

<400> SEQUENCE: 11

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Gly Thr Ile Asp Phe
    50                  55                  60

Pro Glu Phe Leu Thr Met Met Ala Arg Lys
65                  70

<210> SEQ ID NO 12
<211> LENGTH: 75
<212> TYPE: PRT
<213> ORGANISM: Artificial Sequence
<220> FEATURE:
<223> OTHER INFORMATION: Chemically Synthesized Calmodulin Protein

<400> SEQUENCE: 12

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30
```

Gly Thr Val Met Arg Ser Leu Gly Gln Asn Pro Thr Glu Ala Glu Leu
            35                  40                  45

Gln Asp Met Ile Asn Glu Val Asp Ala Asp Gly Asp Gly Thr Ile Asp
        50                  55                  60

Phe Pro Glu Phe Leu Thr Met Met Ala Arg Lys
65                  70                  75

<210> SEQ ID NO 13
<211> LENGTH: 73
<212> TYPE: PRT
<213> ORGANISM: Artificial Sequence
<220> FEATURE:
<223> OTHER INFORMATION: Chemically Synthesized Calmodulin Protein

<400> SEQUENCE: 13

Met Lys Asp Thr Asp Ser Glu Glu Glu Ile Arg Glu Ala Phe Arg Val
1               5                   10                  15

Phe Asp Ile Asp Gly Asn Gly Tyr Ile Ser Ala Ala Glu Leu Arg His
            20                  25                  30

Val Met Thr Asn Leu Gly Glu Lys Leu Thr Asp Glu Glu Val Asp Glu
        35                  40                  45

Met Ile Arg Glu Ala Asp Ile Asp Gly Asp Gly Gln Val Asn Tyr Glu
    50                  55                  60

Glu Phe Val Gln Met Met Thr Ala Lys
65                  70

<210> SEQ ID NO 14
<211> LENGTH: 73
<212> TYPE: PRT
<213> ORGANISM: Artificial Sequence
<220> FEATURE:
<223> OTHER INFORMATION: Chemically Synthesized Calmodulin Protein

<400> SEQUENCE: 14

Met Lys Asp Thr Asp Ser Glu Glu Glu Ile Arg Glu Ala Phe Arg Val
1               5                   10                  15

Phe Asp Ile Asp Gly Asp Gly Tyr Ile Ser Ala Ala Glu Leu Arg His
            20                  25                  30

Val Met Thr Asn Leu Gly Glu Lys Leu Thr Asp Glu Glu Val Asp Glu
        35                  40                  45

Met Ile Arg Glu Ala Asp Ile Asp Gly Asp Gly Gln Val Asn Tyr Glu
    50                  55                  60

Glu Phe Val Gln Met Met Thr Ala Lys
65                  70

<210> SEQ ID NO 15
<211> LENGTH: 216
<212> TYPE: PRT
<213> ORGANISM: Artificial Sequence
<220> FEATURE:
<223> OTHER INFORMATION: Chemically Synthesized CaM-affi Protein

<400> SEQUENCE: 15

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

```
Gln Asp Met Ile Asn Glu Val Asp Ala Asp Gly Asp Gly Thr Ile Asp
 50                  55                  60
Phe Pro Glu Phe Leu Thr Met Met Ala Arg Lys Met Lys Asp Thr Gly
 65                  70                  75                  80
Gly Ser Gly Gly Val Asp Asn Lys Phe Asn Lys Glu Met Arg Asn Ala
                 85                  90                  95
Tyr Trp Glu Ile Ala Leu Leu Pro Asn Leu Asn Asn Gln Gln Lys Arg
            100                 105                 110
Ala Phe Ile Arg Ser Leu Tyr Asp Asp Pro Ser Gln Ser Ala Asn Leu
        115                 120                 125
Leu Ala Glu Ala Lys Lys Leu Asn Asp Ala Gln Ala Pro Lys Gly Gly
130                 135                 140
Ser Gly Gly Asp Ser Glu Glu Ile Arg Glu Ala Phe Arg Val Phe
145                 150                 155                 160
Asp Lys Asp Gly Asp Gly Tyr Ile Ser Ala Ala Glu Leu Arg His Val
                165                 170                 175
Met Thr Asn Leu Gly Glu Lys Leu Thr Asp Glu Glu Val Asp Glu Met
            180                 185                 190
Ile Arg Glu Ala Asp Ile Asp Gly Asp Gly Gln Val Asn Tyr Glu Glu
        195                 200                 205
Phe Val Gln Met Met Thr Ala Lys
210                 215

<210> SEQ ID NO 16
<211> LENGTH: 161
<212> TYPE: PRT
<213> ORGANISM: Artificial Sequence
<220> FEATURE:
<223> OTHER INFORMATION: Chemically Synthesized CaM-Bom Protein

<400> S

```
<213> ORGANISM: Homo sapiens
<220> FEATURE:
<223> OTHER INFORMATION: Calmodulin Protein

<400> SEQUENCE: 17

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Leu Pro Gly Asn Gly
    50                  55                  60

Thr Ile Asp Phe Pro Glu Phe Leu Thr Met Met Ala Arg Lys Met Lys
65              70                  75                  80

Asp Thr Asp Ser Glu Glu Ile Arg Glu Ala Phe Arg Val Phe Asp
                85                  90                  95

Lys Asp Gly Asn Gly Tyr Ile Ser Ala Ala Glu Leu Arg His Val Met
            100                 105                 110

Thr Asn Leu Gly Glu Lys Leu Thr Asp Glu Glu Val Asp Glu Met Ile
        115                 120                 125

Arg Glu Ala Asp Ile Asp Gly Asp Gly Gln Val Asn Tyr Glu Glu Phe
    130                 135                 140

Val Gln Met Met Thr Ala Lys
145                 150

<210> SEQ ID NO 18
<211> LENGTH: 148
<212> TYPE: PRT
<213> ORGANISM: Mus
<220> FEATURE:
<223> OTHER INFORMATION: Calmodulin Protein

<400> SEQUENCE: 18

Ala Asp Gln Leu Thr Glu Glu Gln Ile Ala Glu Phe Lys Glu Ala Phe
1               5                   10                  15

Ser Leu Phe Asp Lys Asp Gly Asp Asn Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65              70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 19
<211> LENGTH: 148
```

```
<212> TYPE: PRT
<213> ORGANISM: Rattus
<220> FEATURE:
<223> OTHER INFORMATION: Calmodulin Protein

<400> SEQUENCE: 19

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 20
<211> LENGTH: 148
<212> TYPE: PRT
<213> ORGANISM: Oryctolagus cuniculus
<220> FEATURE:
<223> OTHER INFORMATION: Calmodulin Protein

<400> SEQUENCE: 20

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 21
```

```
<211> LENGTH: 148
<212> TYPE: PRT
<213> ORGANISM: Paramecium
<220> FEATURE:
<223> OTHER INFORMATION: Calmodulin Protein

<400> SEQUENCE: 21
```

Ala Glu Gln Leu Thr Glu Glu Gln Ile Ala Glu Phe Lys Glu Ala Phe
1               5                   10                  15

Ala Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
50                  55                  60

Phe Pro Glu Phe Leu Ser Leu Met Ala Arg Lys Met Lys Glu Gln Asp
65                  70                  75                  80

Ser Glu Glu Glu Leu Ile Glu Ala Phe Lys Val Phe Asp Arg Asp Gly
                85                  90                  95

Asn Gly Leu Ile Ser Ala Ala Glu Leu Arg His Val Met Thr Asn Leu
            100                 105                 110

Gly Glu Lys Leu Thr Asp Asp Glu Val Asp Glu Met Ile Arg Glu Ala
        115                 120                 125

Asp Ile Asp Gly Asp Gly His Ile Asn Tyr Glu Glu Phe Val Arg Met
130                 135                 140

Met Val Ser Lys
145

```
<210> SEQ ID NO 22
<211> LENGTH: 164
<212> TYPE: PRT
<213> ORGANISM: Artificial Sequence
<220> FEATURE:
<223> OTHER INFORMATION: Chemically Synthesized CA1-Affibody Protein

<400> SEQUENCE: 22
```

Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
            20                  25                  30

Arg Trp Glu Arg Gly Ser Thr Leu Val Ala Glu Phe Lys Arg Lys Met
        35                  40                  45

Lys Pro Phe Leu Lys Ser Gly Ala Phe Glu Ile Asp Ala Asn Gly Asp
50                  55                  60

Leu Asp Ile Lys Asn Leu Thr Arg Asp Asp Ser Gly Thr Tyr Asn Val
65                  70                  75                  80

Thr Val Tyr Ser Thr Asn Gly Thr Arg Ile Leu Asn Lys Ala Leu Asp
            85                  90                  95

Leu Arg Ile Leu Glu Gly Gly Ser Gly Gly Val Asp Asn Lys Phe Asn
        100                 105                 110

Lys Glu Gln Gln Asn Ala Phe Tyr Glu Ile Leu His Leu Pro Asn Leu
    115                 120                 125

Asn Glu Glu Gln Arg Asn Ala Phe Ile Gln Ser Leu Lys Asp Asp Pro
            130                 135                 140

Ser Gln Ser Ala Asn Leu Leu Ala Glu Ala Lys Lys Leu Asn Asp Ala
145                 150                 155                 160

Gln Ala Pro Lys

```
<210> SEQ ID NO 23
<211> LENGTH: 164
<212> TYPE: PRT
<213> ORGANISM: Artificial Sequence
<220> FEATURE:
<223> OTHER INFORMATION: Chemically Synthesized CA1-Affibody Protein

<400> SEQUENCE: 23

Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
                20                  25                  30

Arg Trp Glu Arg Gly Ser Thr Leu Val Ala Glu Phe Lys Arg Lys Met
            35                  40                  45

Lys Pro Phe Leu Lys Ser Gly Ala Phe Glu Ile Asp Ala Asn Gly Asp
        50                  55                  60

Leu Asp Ile Lys Asn Leu Thr Arg Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu Gly Gly Ser Gly Val Asp Asn Lys Phe Asn
                100                 105                 110

Lys Glu Leu Arg Gln Ala Tyr Trp Glu Ile Gln Ala Leu Pro Asn Leu
                115                 120                 125

Asn Trp Thr Gln Ser Arg Ala Phe Ile Arg Ser Leu Tyr Asp Asp Pro
        130                 135                 140

Ser Gln Ser Ala Asn Leu Leu Ala Glu Ala Lys Lys Leu Asn Asp Ala
145                 150                 155                 160

Gln Ala Pro Lys

<210> SEQ ID NO 24
<211> LENGTH: 164
<212> TYPE: PRT
<213> ORGANISM: Artificial Sequence
<220> FEATURE:
<223> OTHER INFORMATION: Chemically Synthesized CA1-Affibody Protein

<400> SEQUENCE: 24

Gly Ser Arg Asp Ser Gly Thr Val Trp Gly Ala Leu Gly His Gly Ile
1               5                   10                  15

Glu Leu Asn Ile Pro Asn Phe Gln Met Thr Asp Asp Ile Asp Glu Val
                20                  25                  30

Arg Trp Glu Arg Gly Ser Thr Leu Val Ala Glu Phe Lys Arg Lys Met
            35                  40                  45

Lys Pro Phe Leu Lys Ser Gly Ala Phe Glu Ile Asp Ala Asn Gly Asp
        50                  55                  60

Leu Asp Ile Lys Asn Leu Thr Arg Asp Ser Gly Thr Tyr Asn Val
65                  70                  75                  80

Thr Val Tyr Ser Thr Asn Gly Thr Arg Ile Leu Asn Lys Ala Leu Asp
                85                  90                  95

Leu Arg Ile Leu Glu Gly Gly Ser Gly Val Asp Asn Lys Phe Asn
                100                 105                 110

Lys Glu Met Arg Asn Ala Tyr Trp Glu Ile Ala Leu Leu Pro Asn Leu
                115                 120                 125

Asn Asn Gln Gln Lys Arg Ala Phe Ile Arg Ser Leu Tyr Asp Asp Pro
        130                 135                 140
```

Ser Gln Ser Ala Asn Leu Leu Ala Glu Ala Lys Lys Leu Asn Asp Ala
145                 150                 155                 160

Gln Ala Pro Lys

<210> SEQ ID NO 25
<211> LENGTH: 115
<212> TYPE: PRT
<213> ORGANISM: Artificial Sequence
<220> FEATURE:
<223> OTHER INFORMATION: Chemically Synthesized CA1-Bom Protein

<400> SEQUENCE: 25

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Ser Gly Asn Gln Trp Ala Val Gly
            100                 105                 110

His Leu Met
        115

<210> SEQ ID NO 26
<211> LENGTH: 119
<212> TYPE: PRT
<213> ORGANISM: Artificial Sequence
<220> FEATURE:
<223> OTHER INFORMATION: Chemically Synthesized CA1-Bom Protein

<400> SEQUENCE: 26

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Gly Asn Gln Trp Ala Val Gly
    50                  55                  60

His Leu Met Gly Gly Ser Gly Gly Gly Ala Phe Glu Ile Asp Ala Asn
65                  70                  75                  80

Gly Asp Leu Asp Ile Lys Asn Leu Thr Arg Asp Asp Ser Gly Thr Tyr
                85                  90                  95

Asn Val Thr Val Tyr Ser Thr Asn Gly Thr Arg Ile Leu Asn Lys Ala
            100                 105                 110

Leu Asp Leu Arg Ile Leu Glu
        115
```

<210> SEQ ID NO 27
<211> LENGTH: 110
<212> TYPE: PRT
<213> ORGANISM: Artificial Sequence

```
<220> FEATURE:
<223> OTHER INFORMATION: Chemically Synthesized Rat Parvalbumin Protein

<400> SEQUENCE: 27

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Phe Ser Thr Leu Val Ala Glu Ser
            100                 105                 110

<210> SEQ ID NO 28
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 28

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Phe Ser Thr Leu Val Ala Glu Ser
            100                 105                 110

<210> SEQ ID NO 29
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 29

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60
```

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
            85                  90                  95

Lys Ile Gly Val Glu Glu Trp Ser Thr Leu Val Ala Glu Ser
        100                 105                 110

<210> SEQ ID NO 30
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 30

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Asp Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
            85                  90                  95

Lys Ile Gly Val Glu Glu Phe Ser Thr Leu Val Ala Glu Ser
        100                 105                 110

<210> SEQ ID NO 31
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 31

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Asp Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
            85                  90                  95

Lys Ile Gly Val Glu Glu Trp Ser Thr Leu Val Ala Glu Ser
        100                 105                 110

<210> SEQ ID NO 32
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 32

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Asp Val Glu Glu Phe Ser Thr Leu Val Ala Glu Ser
            100                 105                 110

<210> SEQ ID NO 33
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 33

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Asp Val Glu Glu Trp Ser Thr Leu Val Ala Glu Ser
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 34

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Ser Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

```
Lys Glu Thr Lys Thr Leu Met Ala Ala Gly Asp Lys Asp Gly Asp Gly
                85                  90                  95

Lys Ile Asp Val Glu Glu Trp Ser Thr Leu Val Ala Glu Ser
            100                 105                 110

<210> SEQ ID NO 35
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 35

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Glu Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Asp Val Glu Glu Trp Ser Thr Leu Val Ala Glu Ser
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 36

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Ser Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Cys
            100                 105                 110

<210> SEQ ID NO 37
<211> LENGTH: 110
<212> TYPE: PRT
<213> ORGANISM: Artificial Sequence
<220> FEATURE:
<223> OTHER INFORMATION: Chemically Synthesized Rat Parvalbumin Protein

<400> SEQUENCE: 37

Met Ser Met Thr Asp Leu Leu Ser Ala Glu Asp Ile Lys Lys Ala Ile
```

```
                1               5                    10                   15
Gly Ala Phe Thr Ala Ala Asp Ser Phe Asp His Lys Lys Phe Phe Gln
                20                   25                   30

Met Val Gly Leu Lys Lys Lys Ser Ala Asp Asp Val Lys Lys Val Phe
                35                   40                   45

His Ile Leu Asp Lys Asp Lys Ser Gly Phe Ile Glu Glu Asp Glu Leu
    50                   55                   60

Gly Ser Ile Leu Lys Gly Phe Ser Ser Asp Ala Arg Asp Leu Ser Ala
65                  70                   75                   80

Lys Glu Thr Lys Thr Leu Met Ala Ala Gly Asp Lys Asp Gly Asp Gly
                85                   90                   95

Lys Ile Gly Val Glu Glu Trp Ser Thr Leu Val Ala Glu Ser
                100                  105                  110
```

<210> SEQ ID NO 38
<211> LENGTH: 110
<212> TYPE: PRT
<213> ORGANISM: Homo sapiens
<220> FEATURE:
<223> OTHER INFORMATION: Parvalbumin Protein

<400> SEQUENCE: 38

```
Met Ser Met Thr Asp Leu Leu Asn Ala Glu Asp Ile Lys Lys Ala Val
1               5                    10                   15

Gly Ala Phe Ser Ala Thr Asp Ser Phe Asp His Lys Lys Phe Phe Gln
                20                   25                   30

Met Val Gly Leu Lys Lys Lys Ser Ala Asp Asp Val Lys Lys Val Phe
                35                   40                   45

His Met Leu Asp Lys Asp Lys Ser Gly Phe Ile Glu Glu Asp Glu Leu
    50                   55                   60

Gly Phe Ile Leu Lys Gly Phe Ser Pro Asp Ala Arg Asp Leu Ser Ala
65                  70                   75                   80

Lys Glu Thr Lys Met Leu Met Ala Ala Gly Asp Lys Asp Gly Asp Gly
                85                   90                   95

Lys Ile Gly Val Asp Glu Phe Ser Thr Leu Val Ala Glu Ser
                100                  105                  110
```

<210> SEQ ID NO 39
<211> LENGTH: 130
<212> TYPE: PRT
<213> ORGANISM: Artificial Sequence
<220> FEATURE:
<223> OTHER INFORMATION: Chemically Synthesized Parvalbumin Protein

<400> SEQUENCE: 39

```
Met Ser Met Thr Asp Leu Leu Ser Ala Gl

```
Lys Ile Gly Val Glu Glu Trp Ser Thr Leu Val Ala Glu Ser Gly Gly
            100                 105                 110

Gly Lys Lys Trp His Cys Tyr Thr Tyr Phe Pro His His Tyr Cys Val
        115                 120                 125

Tyr Gly
    130

<210> SEQ ID NO 40
<211> LENGTH: 122
<212> TYPE: PRT
<213> ORGANISM: Artificial Sequence
<220> FEATURE:
<223> OTHER INFORMATION: Chemically Synthesized Parvalbumin Protein

<400> SEQUENCE: 40

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
            100                 105                 110

Gly Ala Gln Trp Ala Val Gly His Leu Met
        115                 120

<210> SEQ ID NO 41
<211> LENGTH: 129
<212> TYPE: PRT
<213> ORGANISM: Artificial Sequence
<220> FEATURE:
<223> OTHER INFORMATION: Chemically Synthesized Parvalbumin Protein

<400> SEQUENCE: 41

Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
            100                 105                 110

Gly Lys Tyr Asp Gly Asp Ile Thr Trp Asp Gln Leu Trp Asp Leu Met
        115                 120                 125

Lys
```

<210> SEQ ID NO 42
<211> LENGTH: 125
<212> TYPE: PRT
<213> ORGANISM: Artificial Sequence
<220> FEATURE:
<223> OTHER INFORMATION: Chemically Synthesized Parvalbumin Protein

<400> SEQUENCE: 42

```
Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
            100                 105                 110

Gly Arg Gly Asp Arg Gly Asp Arg Gly Asp Arg Gly Asp
        115                 120                 125
```

<210> SEQ ID NO 43
<211> LENGTH: 111
<212> TYPE: PRT
<213> ORGANISM: Artificial Sequence
<220> FEATURE:
<223> OTHER INFORMATION: Chemically Synthesized Parvalbumin Protein

<400> SEQUENCE: 43

```
Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
            20                  25                  30

Met Val Gly Leu Lys Lys Lys Ser Ala Asp Asp Val Lys Lys Val Phe
        35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Cys
            100                 105                 110
```

<210> SEQ ID NO 44
<211> LENGTH: 173
<212> TYPE: PRT
<213> ORGANISM: Artificial Sequence
<220> FEATURE:
<223> OTHER INFORMATION: Chemically Synthesized Parvalbumin Protein

<400> SEQUENCE: 44

```
Met Ser Met Thr Asp Leu Leu Ser Ala Glu Asp Ile Lys Lys Ala Ile
1               5                   10                  15

Gly Ala Phe Thr Ala Ala Asp Ser Phe Asp His Lys Lys Phe Phe Gln
```

```
                20                  25                  30
Met Val Gly Leu Lys Lys Ser Ala Asp Val Lys Lys Val Phe
                35                  40                  45

His Ile Leu Asp Lys Asp Lys Asp Gly Phe Ile Glu Glu Asp Glu Leu
    50                  55                  60

Gly Ser Ile Leu Lys Gly Phe Ser Ser Asp Ala Arg Asp Leu Ser Ala
65                  70                  75                  80

Lys Glu Thr Lys Thr Leu Met Ala Ala Gly Asp Lys Asp Gly Asp Gly
                85                  90                  95

Lys Ile Gly Val Glu Glu Trp Ser Thr Leu Val Ala Glu Ser Gly Gly
                100                 105                 110

Ser Gly Gly Val Asp Asn Lys Phe Asn Lys Glu Met Arg Asn Ala Tyr
                115                 120                 125

Trp Glu Ile Ala Leu Leu Pro Asn Leu Asn Asn Gln Gln Lys Arg Ala
            130                 135                 140

Phe Ile Arg Ser Leu Tyr Asp Asp Pro Ser Gln Ser Ala Asn Leu Leu
145                 150                 155                 160

Ala Glu Ala Lys Lys Leu Asn Asp Ala Gln Ala Pro Lys
                165                 170
```

```
<210> SEQ ID NO 45
<211> LENGTH: 79
<212> TYPE: PRT
<213> ORGANISM: Artificial Sequence
<220> FEATURE:
<223> OTHER INFORMATION: Chemically Synthesized Calbindin Protein

<400> SEQUENCE: 45

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Ser Leu Leu Lys Gly Pro Asn
            35                  40                  45

Thr Leu Asp Asp Leu Phe Gln Glu Leu Asp Lys Asn Gly Asp Gly Glu
        50                  55                  60

Val Ser Phe Glu Glu Phe Gln Val Leu Val Lys Lys Ile Ser Gln
65                  70                  75
```

```
<210> SEQ ID NO 46
<211> LENGTH: 79
<212> TYPE: PRT
<213> ORGANISM: Artificial Sequence
<220> FEATURE:
<223> OTHER INFORMATION: Chemically Synthesized Calbindin Protein

<400> SEQUENCE: 46

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Ser Leu Leu Lys Gly Pro Asn
            35                  40                  45

Thr Leu Asp Asp Leu Phe Gln Glu Leu Asp Lys Asn Gly Asp Gly Glu
        50                  55                  60

Val Ser Phe Glu Glu Trp Gln Val Leu Val Lys Lys Ile Ser Gln
65                  70                  75
```

<210> SEQ ID NO 47
<211> LENGTH: 79
<212> TYPE: PRT
<213> ORGANISM: Artificial Sequence
<220> FEATURE:
<223> OTHER INFORMATION: Chemically Synthesized Calbindin Protein

<400> SEQUENCE: 47

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Ser Leu Leu Lys Gly Met Asn
            35                  40                  45

Thr Leu Asp Asp Leu Phe Gln Glu Leu Asp Lys Asn Gly Asp Gly Glu
        50                  55                  60

Val Ser Phe Glu Glu Trp Gln Val Leu Val Lys Lys Ile Ser Gln
65                  70                  75

<210> SEQ ID NO 48
<211> LENGTH: 80
<212> TYPE: PRT
<213> ORGANISM: Artificial Sequence
<220> FEATURE:
<223> OTHER INFORMATION: Chemically Synthesized Calbindin Protein

<400> SEQUENCE: 48

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Ser Leu Leu Lys Gly Pro Asn
            35                  40                  45

Thr Leu Asp Asp Leu Phe Gln Glu Leu Asp Lys Asn Gly Asp Gly Glu
        50                  55                  60

Val Ser Phe Glu Glu Phe Gln Val Leu Val Lys Lys Ile Ser Gln Cys
65                  70                  75                  80

<210> SEQ ID NO 49
<211> LENGTH: 160
<212> TYPE: PRT
<213> ORGANISM: Artificial Sequence
<220> FEATURE:
<223> OTHER INFORMATION: Chemically Synthesized Troponin Protein

<400> SEQUENCE: 49

Met Thr Asp Gln Gln Ala Glu Ala Arg Ser Tyr Leu Ser Glu Glu Met
1               5                   10                  15

Ile Ala Glu Phe Lys Ala Ala Phe Asp Met Phe Asp Ala Asp Gly Gly
                20                  25                  30

Gly Asp Ile Ser Val Lys Glu Leu Gly Thr Val Met Arg Met Leu Gly
            35                  40                  45

Gln Thr Pro Thr Lys Glu Glu Leu Asp Ala Ile Ile Glu Glu Val Asp
        50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
                85                  90                  95

Ala Glu Cys Phe Arg Ile Phe Asp Arg Asn Ala Asp Gly Tyr Ile Asp

```
                100             105                 110
Pro Gly Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
    130                 135                 140

Gly Arg Ile Asp Phe Asp Glu Phe Leu Lys Met Met Glu Gly Val Gln
145                 150                 155                 160
```

<210> SEQ ID NO 50
<211> LENGTH: 122
<212> TYPE: PRT
<213> ORGANISM: Artificial Sequence
<220> FEATURE:
<223> OTHER INFORMATION: Chemically Synthesized Rat CA1-CD2-Bombesin-RGD
    (52I)-Cend

<400> SEQUENCE: 50

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ser Gly Gly Asn Gln Trp Ala Val Gly
    50                  55                  60

His Leu Met Gly Gly Ser Gly Gly Gly Ala Phe Glu Ile Asp Ala Asn
65                  70                  75                  80

Gly Asp Leu Asp Ile Lys Asn Leu Thr Arg Asp Ser Gly Thr Tyr
            85                  90                  95

Asn Val Thr Val Tyr Ser Thr Asn Gly Thr Arg Ile Leu Asn Lys Ala
            100                 105                 110

Leu Asp Leu Arg Ile Leu Glu Arg Gly Asp
        115                 120
```

<210> SEQ ID NO 51
<211> LENGTH: 122
<212> TYPE: PRT
<213> ORGANISM: Artificial Sequence
<220> FEATURE:
<223> OTHER INFORMATION: Chemically Synthesized Rat CA1-CD2-Bombesin-RGD
    (52I)-Nend

<400> SEQUENCE: 51

```
Arg Gly Asp Arg Asp Ser Gly Thr Val Trp Gly Ala Leu Gly His Gly
1               5                   10                  15

Ile Glu Leu Asn Ile Pro Asn Phe Gln Met Thr Asp Asp Ile Asp Glu
            20                  25                  30

Val Arg Trp Glu Arg Gly Ser Thr Leu Val Ala Glu Phe Lys Arg Lys
        35                  40                  45

Met Lys Pro Phe Leu Lys Ser Gly Ser Gly Gly Asn Gln Trp
    50                  55                  60

Ala Val Gly His Leu Met Gly Gly Ser Gly Gly Gly Ala Phe Glu Ile
65                  70                  75                  80

Asp Ala Asn Gly Asp Leu Asp Ile Lys Asn Leu Thr Arg Asp Ser
            85                  90                  95

Gly Thr Tyr Asn Val Thr Val Tyr Ser Thr Asn Gly Thr Arg Ile Leu
            100                 105                 110

Asn Lys Ala Leu Asp Leu Arg Ile Leu Glu
```

-continued

```
              115                 120

<210> SEQ ID NO 52
<211> LENGTH: 113
<212> TYPE: PRT
<213> ORGANISM: Artificial Sequence
<220> FEATURE:
<223> OTHER INFORMATION: Chemically Synthesized Rat CA1-CD2-RGD-83I

<400> SEQUENCE: 52

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Gly Gly Ser Gly Gly Arg Gly Asp Gly Gly Ser Gly Gly
                85                  90                  95

Asn Gly Thr Arg Ile Leu Asn Lys Ala Leu Asp Leu Arg Ile Leu Glu
            100                 105                 110

Gly

<210> SEQ ID NO 53
<211> LENGTH: 135
<212> TYPE: PRT
<213> ORGANISM: Artificial Sequence
<220> FEATURE:
<223> OTHER INFORMATION: Chemically Synthesized Rat
      CA1-CD2-Bom-52I-RGD-83I

<400> SEQUENCE: 53

Arg Gly Asp Arg Asp Ser Gly Thr Val Trp Gly Ala Leu Gly His Gly
1               5                   10                  15

Ile Glu Leu Asn Ile Pro Asn Phe Gln Met Thr Asp Asp Ile Asp Glu
            20                  25                  30

Val Arg Trp Glu Arg Gly Ser Thr Leu Val Ala Glu Phe Lys Arg Lys
        35                  40                  45

Met Lys Pro Phe Leu Lys Ser Gly Ser Gly Gly Gly Asn Gln Trp
    50                  55                  60

Ala Val Gly His Leu Met Gly Gly Ser Gly Gly Ala Phe Glu Ile
65                  70                  75                  80

Asp Ala Asn Gly Asp Leu Asp Ile Lys Asn Leu Thr Arg Asp Asp Ser
                85                  90                  95

Gly Thr Tyr Asn Val Thr Val Tyr Ser Thr Gly Gly Ser Gly Gly Arg
            100                 105                 110

Gly Asp Gly Gly Ser Gly Gly Asn Gly Thr Arg Ile Leu Asn Lys Ala
        115                 120                 125

Leu Asp Leu Arg Ile Leu Glu
    130                 135
```